United States Patent
Feig et al.

(10) Patent No.: US 10,124,153 B2
(45) Date of Patent: Nov. 13, 2018

(54) BALLOON CATHETER AND METHODS OF USE THEREOF

(71) Applicant: AngioSlide Ltd., Natania (IL)

(72) Inventors: Roy Feig, Jerusalem (IL); Gal Meister, Even-Yehuda (IL); Alex Barash, Zoran (IL); Gil Bernstein, Kiryat-Ono (IL)

(73) Assignee: AngioSlide Ltd., Natania (IL)

( * ) Notice: Subject to any disclaimer, the term of this patent is extended or adjusted under 35 U.S.C. 154(b) by 558 days.

(21) Appl. No.: 14/730,265

(22) Filed: Jun. 4, 2015

(65) Prior Publication Data

US 2015/0306361 A1    Oct. 29, 2015

Related U.S. Application Data

(63) Continuation of application No. PCT/IL2013/000089, filed on Dec. 4, 2013.
(Continued)

(51) Int. Cl.
*A61M 25/10* (2013.01)
*A61M 25/00* (2006.01)
(Continued)

(52) U.S. Cl.
CPC ......... *A61M 25/104* (2013.01); *A61B 17/221* (2013.01); *A61B 17/22032* (2013.01);
(Continued)

(58) Field of Classification Search
CPC ............ A61B 17/22032; A61B 17/221; A61B 2017/22035; A61B 2017/22051; A61B 2017/22052; A61B 2017/22054; A61B 2017/22065; A61B 2017/22079; A61B 2017/2215; A61F 2/958; A61M 1/0009; A61M 1/0011; A61M 1/0039;
(Continued)

(56) References Cited

U.S. PATENT DOCUMENTS

| 4,004,588 A | 1/1977 | Alexander |
| 4,243,040 A | 1/1981 | Beecher |

(Continued)

FOREIGN PATENT DOCUMENTS

| CA | 2183214 | 2/1998 |
| CN | 1322145 | 11/2001 |

(Continued)

OTHER PUBLICATIONS

Official Action dated Jul. 28, 2016 From the US Patent and Trademark Office Re. U.S. Appl. No. 13/522,717.
(Continued)

*Primary Examiner* — Nathan R Price
*Assistant Examiner* — Anh Bui

(57) ABSTRACT

A balloon catheter including a shaft and an inflatable balloon attached to the shaft, the catheter includes an open sleeve having a proximal end sealingly attached to the catheter shaft and an open distal end. The sleeve surrounds at least part of the balloon. The sleeve and the balloon are arranged such that inflating the balloon expands the sleeve into an expanded state and deflating the balloon when the sleeve is in the expanded state forms an open cavity between the sleeve and the deflated balloon and creates suction to capture and retain debris within the cavity.

43 Claims, 21 Drawing Sheets

Related U.S. Application Data

(60) Provisional application No. 61/732,944, filed on Dec. 4, 2012.

(51) Int. Cl.
    *A61B 17/221* (2006.01)
    *A61M 1/00* (2006.01)
    *A61F 2/958* (2013.01)
    *A61B 17/22* (2006.01)
    *A61M 25/01* (2006.01)

(52) U.S. Cl.
CPC ............ *A61F 2/958* (2013.01); *A61M 1/0009* (2013.01); *A61M 1/0011* (2013.01); *A61M 1/0039* (2013.01); *A61M 1/0045* (2014.02); *A61M 1/0066* (2013.01); *A61M 1/0072* (2014.02); *A61M 25/0074* (2013.01); *A61M 25/0082* (2013.01); *A61M 25/1006* (2013.01); *A61M 25/1011* (2013.01); *A61B 17/22031* (2013.01); *A61B 2017/2215* (2013.01); *A61B 2017/22035* (2013.01); *A61B 2017/22038* (2013.01); *A61B 2017/22051* (2013.01); *A61B 2017/22052* (2013.01); *A61B 2017/22054* (2013.01); *A61B 2017/22061* (2013.01); *A61B 2017/22065* (2013.01); *A61B 2017/22079* (2013.01); *A61F 2002/9583* (2013.01); *A61M 2025/0004* (2013.01); *A61M 2025/0024* (2013.01); *A61M 2025/0039* (2013.01); *A61M 2025/0183* (2013.01); *A61M 2025/105* (2013.01); *A61M 2025/109* (2013.01); *A61M 2025/1013* (2013.01); *A61M 2025/1015* (2013.01); *A61M 2025/1052* (2013.01); *A61M 2025/1081* (2013.01); *A61M 2025/1086* (2013.01); *A61M 2025/1093* (2013.01); *A61M 2202/0007* (2013.01); *A61M 2202/0014* (2013.01); *A61M 2205/32* (2013.01)

(58) Field of Classification Search
CPC .............. A61M 1/0045; A61M 1/0066; A61M 1/0072; A61M 2025/0004; A61M 2025/0024; A61M 2025/0025; A61M 2025/0039; A61M 2025/0183; A61M 2025/1013; A61M 2025/1015; A61M 2025/1052; A61M 2025/1081; A61M 2025/1086; A61M 2025/109; A61M 2025/1093; A61M 2202/0014; A61M 2202/0028; A61M 2202/0042; A61M 2202/005; A61M 25/0074; A61M 25/0082; A61M 25/1006; A61M 25/1011
See application file for complete search history.

(56) References Cited

U.S. PATENT DOCUMENTS

| | | | |
|---|---|---|---|
| 4,271,839 A | 6/1981 | Fogarty et al. | |
| 4,469,100 A | 9/1984 | Hardwick | |
| 4,597,389 A | 7/1986 | Ibrahim et al. | |
| 4,611,594 A | 9/1986 | Grayhack et al. | |
| 4,748,982 A | 6/1988 | Horzewski et al. | |
| 4,762,129 A | 8/1988 | Bonzel | |
| 4,820,270 A | 4/1989 | Hardcastle et al. | |
| 4,846,174 A | 7/1989 | Willard et al. | |
| 4,946,440 A | 8/1990 | Hall | |
| 4,955,895 A | 9/1990 | Sugiyama et al. | |
| 4,968,300 A | 11/1990 | Moutafis et al. | |
| 5,019,041 A | 5/1991 | Robinson et al. | |
| 5,074,845 A | 12/1991 | Miraki et al. | |
| 5,092,839 A | 3/1992 | Kipperman | |
| 5,109,830 A | 5/1992 | Cho | |
| 5,254,091 A | 10/1993 | Aliahmad et al. | |
| 5,307,814 A | 5/1994 | Kressel et al. | |
| RE34,633 E | 6/1994 | Sos et al. | |
| 5,338,298 A | 8/1994 | McIntyre | |
| 5,421,826 A | 6/1995 | Crocker et al. | |
| 5,437,638 A | 8/1995 | Bowman | |
| 5,445,646 A | 8/1995 | Euteneuer et al. | |
| 5,470,314 A | 11/1995 | Walinsky | |
| 5,534,007 A | 7/1996 | St. Germain et al. | |
| 5,571,086 A * | 11/1996 | Kaplan | A61B 8/12 604/96.01 |
| 5,630,822 A | 5/1997 | Hermann et al. | |
| 5,785,675 A | 7/1998 | Drasler et al. | |
| 5,865,801 A | 2/1999 | Houser | |
| 5,868,767 A | 2/1999 | Farley et al. | |
| 5,941,895 A | 8/1999 | Myler et al. | |
| 5,968,012 A | 10/1999 | Ren et al. | |
| 6,004,341 A | 12/1999 | Zhu et al. | |
| 6,022,359 A | 2/2000 | Frantzen | |
| 6,039,721 A | 3/2000 | Johnson et al. | |
| 6,063,057 A | 5/2000 | Choh | |
| 6,129,706 A | 10/2000 | Janacek | |
| 6,152,947 A | 11/2000 | Ambrisco et al. | |
| 6,159,230 A | 12/2000 | Samuels | |
| 6,179,827 B1 | 1/2001 | Davis et al. | |
| 6,280,412 B1 | 8/2001 | Pedersen, Jr. et al. | |
| 6,383,195 B1 | 5/2002 | Richard | |
| 6,695,810 B2 | 2/2004 | Peacock, III et al. | |
| 7,172,576 B2 | 2/2007 | Sawa et al. | |
| 7,201,770 B2 | 4/2007 | Johnson et al. | |
| 7,563,270 B2 | 7/2009 | Gumm | |
| 7,591,831 B2 | 9/2009 | Parsonage et al. | |
| 7,824,345 B2 | 11/2010 | Euteneuer et al. | |
| 7,824,370 B2 | 11/2010 | Hirszowicz et al. | |
| 8,556,851 B2 | 10/2013 | Hirszowicz et al. | |
| 2002/0082639 A1 | 6/2002 | Broome et al. | |
| 2002/0091398 A1 | 7/2002 | Galdonik et al. | |
| 2002/0121472 A1 | 9/2002 | Garner et al. | |
| 2002/0177870 A1 | 11/2002 | Sepetka et al. | |
| 2003/0028211 A1 | 2/2003 | Crocker et al. | |
| 2003/0055483 A1 | 3/2003 | Gumm | |
| 2003/0093107 A1 | 5/2003 | Parsonage et al. | |
| 2003/0105508 A1 | 6/2003 | Johnson et al. | |
| 2003/0130672 A1 * | 7/2003 | DoBrava | A61B 17/22 606/159 |
| 2003/0176884 A1 | 9/2003 | Berrada et al. | |
| 2003/0176910 A1 | 9/2003 | Vrba et al. | |
| 2003/0208223 A1 | 11/2003 | Kleiner | |
| 2004/0049223 A1 | 3/2004 | Nishtala et al. | |
| 2004/0054362 A1 | 3/2004 | Lopath et al. | |
| 2004/0073243 A1 | 4/2004 | Sepetka et al. | |
| 2004/0236275 A1 | 11/2004 | Pruitt et al. | |
| 2004/0236367 A1 | 11/2004 | Brown et al. | |
| 2005/0004553 A1 | 1/2005 | Douk | |
| 2005/0085826 A1 | 4/2005 | Nair et al. | |
| 2005/0101986 A1 | 5/2005 | Daniel et al. | |
| 2005/0102019 A1 | 5/2005 | Yadin | |
| 2005/0137501 A1 | 6/2005 | Euteneuer et al. | |
| 2005/0137607 A1 | 6/2005 | Assell et al. | |
| 2005/0154414 A1 | 7/2005 | Perreault et al. | |
| 2005/0187570 A1 | 8/2005 | Nguyen et al. | |
| 2005/0209629 A1 | 9/2005 | Kerr et al. | |
| 2005/0261705 A1 | 11/2005 | Gist | |
| 2005/0288700 A1 | 12/2005 | Chermoni | |
| 2006/0015134 A1 | 1/2006 | Trinidad | |
| 2006/0025720 A1 | 2/2006 | Sawa et al. | |
| 2006/0129107 A1 | 6/2006 | McArthur et al. | |
| 2006/0129710 A1 | 6/2006 | O'Connor et al. | |
| 2007/0032787 A1 * | 2/2007 | Hassett | A61B 18/1492 606/41 |
| 2007/0083158 A1 | 4/2007 | Hirszowicz et al. | |
| 2007/0088380 A1 | 4/2007 | Hirszowicz et al. | |
| 2007/0255305 A1 | 11/2007 | McMichael et al. | |
| 2008/0051706 A1 | 2/2008 | Hirszowicz et al. | |
| 2009/0112239 A1 | 4/2009 | To | |
| 2009/0171278 A1 | 7/2009 | Hirszowicz et al. | |
| 2009/0204069 A1 | 8/2009 | Hirszowicz et al. | |
| 2009/0247945 A1 | 10/2009 | Levit et al. | |
| 2009/0270902 A1 | 10/2009 | Assell et al. | |

(56) References Cited

U.S. PATENT DOCUMENTS

| | | | |
|---|---|---|---|
| 2010/0010303 A1 | 1/2010 | Bakos | |
| 2010/0016792 A1 | 1/2010 | Hirszowicz | |
| 2010/0022970 A1* | 1/2010 | Hirszowicz | A61B 17/22032 604/268 |
| 2010/0069900 A1 | 3/2010 | Shirley et al. | |
| 2011/0040365 A1 | 2/2011 | Hirszowicz et al. | |
| 2011/0275990 A1 | 11/2011 | Besser et al. | |
| 2012/0143054 A1 | 6/2012 | Eaton et al. | |
| 2012/0302996 A1 | 11/2012 | Barash et al. | |
| 2013/0006291 A1 | 1/2013 | Harari et al. | |
| 2013/0060234 A1 | 3/2013 | Besser et al. | |
| 2015/0126966 A1 | 5/2015 | Hirszowicz et al. | |
| 2017/0246432 A1* | 8/2017 | Baumbach | A61M 25/104 |

FOREIGN PATENT DOCUMENTS

| | | |
|---|---|---|
| CN | 101583318 | 11/2009 |
| CN | 101972510 | 2/2011 |
| CN | 102131471 | 7/2011 |
| EP | 0200668 | 12/1986 |
| EP | 0359489 | 3/1990 |
| EP | 0366478 | 5/1990 |
| EP | 0380873 | 8/1990 |
| EP | 0399712 | 11/1990 |
| EP | 0987045 | 3/2000 |
| EP | 1062966 | 12/2000 |
| EP | 1120129 | 8/2001 |
| EP | 1124504 | 8/2001 |
| EP | 1333778 | 8/2003 |
| EP | 1753348 | 2/2007 |
| GB | 2054385 | 2/1981 |
| IL | 178738 | 2/2007 |
| JP | 54-066582 | 5/1979 |
| JP | 59-502134 | 12/1984 |
| JP | 61-293474 | 12/1986 |
| JP | 02-119875 | 5/1990 |
| JP | 07-136283 | 5/1995 |
| JP | 2000-005189 | 1/2000 |
| JP | 2002-520099 | 7/2002 |
| JP | 2003-126263 | 5/2003 |
| JP | 2004-329485 | 11/2004 |
| JP | 2005-514979 | 5/2005 |
| WO | WO 84/01513 | 4/1984 |
| WO | WO 1995/017223 | 6/1995 |
| WO | WO 98/29026 | 7/1998 |
| WO | WO 00/02613 | 1/2000 |
| WO | WO 00/27309 | 5/2000 |
| WO | WO 00/38776 | 7/2000 |
| WO | WO 02/38084 | 5/2002 |
| WO | WO 02/055146 | 7/2002 |
| WO | WO 2004/014240 | 2/2004 |
| WO | WO 2004/017865 | 3/2004 |
| WO | WO 2004/028611 | 4/2004 |
| WO | WO 2004/082462 | 9/2004 |
| WO | WO 2004/098681 | 11/2004 |
| WO | WO 2005/000130 | 1/2005 |
| WO | WO 2005/030308 | 4/2005 |
| WO | WO 2005/041788 | 5/2005 |
| WO | WO 2005/102184 | 11/2005 |
| WO | WO 2005/112783 | 12/2005 |
| WO | WO 2007/004221 | 1/2007 |
| WO | WO 2007/042935 | 4/2007 |
| WO | WO 2007/042936 | 4/2007 |
| WO | WO 2007/132464 | 11/2007 |
| WO | WO 2008/004238 | 1/2008 |
| WO | WO 2008/004239 | 1/2008 |
| WO | WO 2009/053839 | 4/2009 |
| WO | WO 2010/001404 | 1/2010 |
| WO | WO 2010/001405 | 1/2010 |
| WO | WO 2010/079494 | 7/2010 |
| WO | WO 2011/036667 | 3/2011 |
| WO | WO 2011/080731 | 7/2011 |
| WO | WO 2011/080732 | 7/2011 |
| WO | WO 2011/089599 | 7/2011 |
| WO | WO 2014/087395 | 6/2014 |
| WO | WO 2016/199117 | 12/2016 |
| WO | WO 2018/033920 | 2/2018 |

OTHER PUBLICATIONS

Restriction Official Action dated Aug. 2, 2016 From the US Patent and Trademark Office Re. U.S. Appl. No. 13/520,345.
Supplementary European Search Report dated Jul. 1, 2016 From the European Patent Office Re. Application No. 13861353.4.
Official Action dated Jan. 25, 2016 From the US Patent and Trademark Office Re. U.S. Appl. No. 14/012,624.
Notification of Office Action dated Aug. 25, 2017 From the State Intellectual Property Office of the People's Republic of China Re. Application No. 201380071889.6 and Its Translation Into English. (7 Pages).
Notice of Reason for Rejection dated Aug. 8, 2017 From the Japan Patent Office Re. Application No. 2015-546149 and Its Machine Translation Into English. (9 Pages).
Communication Pursuant to Article 94(3) EPC dated Feb. 3, 2017 From the European Patent Office Re. Application No. 13861353.4. (7 Pages).
Office Action and Search Report dated Jan. 4, 2017 From the state Intellectual Property Office of the People's Republic of China Re. Application No. 201380071889.6 and Its Translation Into English. (12 Pages).
Official Action dated Dec. 19, 2016 From the US Patent and Trademark Office Re. U.S. Appl. No. 14/551,866. (41 pages).
Official Action dated Nov. 10, 2016 From the US Patent and Trademark Office Re. U.S. Appl. No. 13/522,717, (14 pages).
International Search Report and the Written Opinion dated Oct. 13, 2015 From the International Searching Authority Re. Application No. PCT/IL2015/050582.
Notice of Allowance dated Jun. 7, 2013 From the US Patent and Trademark Office Re. U.S. Appl. No. 11/477,812.
Notice of Allowance dated Jun. 25, 2010 From the US Patent and Trademark Office Re. U.S. Appl. No. 11/587,179.
Official Action dated Jul. 6, 2012 From the US Patent and Trademark Office Re. U.S. Appl. No. 11/477,812.
Official Action dated Feb. 23, 2011 From the US Patent and Trademark Office Re. U.S. Appl. No. 11/477,812.
Official Action dated Nov. 28, 2011 From the US Patent and Trademark Office Re. U.S. Appl. No. 11/477,812.
Restriction Official Action dated Sep. 13, 2010 From the US Patent and Trademark Office Re. U.S. Appl. No. 11/477,812.
Restriction Official Action dated Sep. 23, 2016 From the US Patent and Trademark Office Re. U.S. Appl. No. 14/551,866.
Examination Report dated Dec. 31, 2012 From the Government of India, Patent Office, Intellectual Property Building Re. Application No. 3402/KOLNP/2006.
Official Action dated Oct. 16, 2015 From the US Patent and Trademark Office Re. U.S. Appl. No. 13/522,717.
Supplementary European Search Report and the European Search Opinion dated Jul. 18, 2011 From the European Patent Office Re. Application No. 09773060.0.
Supplementary Partial European Search Report and the European Search Opinion dated Oct. 19, 2009 From the European Patent Office Re. Application No. 07766874.7.
Examination Report Under Sections 12 & 13 of the Patents Act, 1970 and the Patents Rules, 2003 dated May 10, 2016 From the Government of India, Patent Office, Intellectual Property Building Re. Application No. 439/KOLNP/2008.
Communication Pursuant to Article 94(3) and Rule 71(1) EPC dated Jan. 28, 2010 From the European Patent Office Re. Application No. 07766874.7.
Communication Pursuant to Article 94(3) EPC dated Apr. 4, 2012 From the European Patent Office Re. Application No. 10170623.2.
Communication Pursuant to Article 94(3) EPC dated Mar. 10, 2011 From the European Patent Office Re. Application No. 07766875.4.
Communication Pursuant to Article 94(3) EPC dated Feb. 23, 2010 From the European Patent Office Re. Application No. 07766875.4.

(56) References Cited

OTHER PUBLICATIONS

Communication Pursuant to Article 94(3) EPC dated Jan. 28, 2010 From the European Patent Office Re. Application No. 07766874.7.
Communication Pursuant to Article 94(3) EPC dated Dec. 29, 2008 From the European Patent Office Re. Application No. 05735055.5.
Communication Pursuant to Article 94(3) EPC dated May 29, 2008 From the European Patent Office Re. Application No. 06766111.6.
Communication Pursuant to Article 94(3) EPC dated Aug. 30, 2011 From the European Patent Office Re. Application No. 10170623.2.
Communication Pursuant to Article 96(2) EPC dated Nov. 5, 2007 From the European Patent Office Re. Application No. 05735055.5.
Communication Pursuant to Rules 161(2) and 162 EPC dated May 3, 2012 From the European Patent Office Re. Application No. 10818501.8.
Communication Pursuant to Rules 161(2) and 162 EPC dated Feb. 14, 2011 From the European Patent Office Re. Application No. 09773059.2.
Communication Pursuant to Rules 161(2) and 162 EPC dated Feb. 14, 2011 From the European Patent Office Re. Application No. 09773060.0.
Communication Pursuant to Rules 161(2) and 162 EPC dated Jul. 15, 2015 From the European Patent Office Re. Application No. 13861353.4.
Decision of Patent dated Mar. 6, 2012 From the Japanese Patent Office Re. Application No. 2007-509059 and Its Translation Into English.
Decision to Grant a European Patent Pursuant to Article 97(1) EPC dated Aug. 12, 2010 From the European Patent Office Re. Application No. 10170623.2.
Decision to Grant a European Patent Pursuant to Article 97(1) EPC dated Aug. 17, 2012 From the European Patent Office Re. Application No. 10169255.6.
Decision to Grant a European Patent Pursuant to Article 97(1) EPC dated Jul. 19, 2010 From the European Patent Office Re. Application No. 05735055.5.
European Search Report and the European Search Opinion dated Nov. 15, 2010 From the European Patent Office Re. Application No. 10169255.6.
European Search Report and the European Search Opinion dated Nov. 26, 2010 From the European Patent Office Re. Application No. 10170623.2.
Examiner's Report dated Feb. 2, 2011 From the Australian Government, IP Australia Re. Application No. 2006264397.
Final Rejection dated Aug. 30, 2011 From the Japanese Patent Office Re. Application No. 2007-509059 and Its Translation Into English.
International Preliminary Report on Patentability dated Jul. 4, 2012 From the International Bureau of WIPO Re. Application No. PCT/IL2010/000002.
International Preliminary Report on Patentability dated Jan. 5, 2011 From the International Bureau of WIPO Re. Application No. PCT/IL2009/000667.
International Preliminary Report on Patentability dated Jan. 5, 2011 From the International Bureau of WIPO Re. Application No. PCT/IL2009/000668.
International Preliminary Report on Patentability dated Apr. 7, 2007 From the International Bureau of WIPO Re. Application No. PCT/IL2007/000845.
International Preliminary Report on Patentability dated Apr. 7, 2009 From the International Bureau of WIPO Re. Application No. PCT/IL2007/000844.
International Preliminary Report on Patentability dated Jan. 9, 2008 From the International Bureau of WIPO Re. Application No. PCT/IL2006/000770.
International Preliminary Report on Patentability dated Jun. 9, 2015 From the International Bureau of WIPO Re. Application No. PCT/IL2013/000089.
International Preliminary Report on Patentability dated Mar. 10, 2009 From the International Bureau of WIPO Re. Application No. PCT/IB2006/002955.
International Preliminary Report on Patentability dated Jul. 12, 2011 From the International Bureau of WIPO Re. Application No. PCT/IL2009/000667.
International Preliminary Report on Patentability dated Jul. 24, 2012 From the International Bureau of WIPO Re. Application No. PCT/IL2011/000060.
International Preliminary Report on Patentability dated Oct. 25, 2006 From the International Bureau of WIPO Re. Application No. PCT/IL2005/000420.
International Preliminary Report on Patentability dated Mar. 27, 2012 From the International Bureau of WIPO Re. Application No. PCT/IL2010/000797.
International Search Report and the Written Opinion dated Jun. 1, 2010 From the International Searching Authority Re. Application No. PCT/IL2010/000025.
International Search Report and the Written Opinion dated Nov. 3, 2006 From the International Searching Authority Re. Application No. PCT/IL2006/000770.
International Search Report and the Written Opinion dated May 7, 2010 From the International Searching Authority Re. Application No. PCT/IL2010/000001.
International Search Report and the Written Opinion dated Aug. 11, 2008 From the International Searching Authority Re. Application No. PCT/IL2007/000844.
International Search Report and the Written Opinion dated Aug. 11, 2008 From the International Searching Authority Re. Application No. PCT/IL2007/000845.
International Search Report and the Written Opinion dated May 12, 2010 From the International Searching Authority Re. Application No. PCT/IL2010/000002.
International Search Report and the Written Opinion dated Feb. 23, 2011 From the International Searching Authority Re. Application No. PCT/IL2010/000797.
International Search Report and the Written Opinion dated May 23, 2011 From the International Searching Authority Re. Application No. PCT/IL2011/000060.
International Search Report and the Written Opinion dated Mar. 26, 2014 From the International Searching Authority Re. Application No. PCT/IL2013/000089.
International Search Report and the Written Opinion dated Oct. 28, 2009 From the International Searching Authority Re. Application No. PCT/IL2009/000667.
International Search Report and the Written Opinion dated Oct. 28, 2009 From the International Searching Authority Re. Application No. PCT/IL2009/000668.
International Search Report and the Written Opinion dated Jul. 29, 2005 From the International Searching Authority Re. Application No. PCT/IL2005/000420.
International Search Report and the Written Opinion dated Oct. 29, 2008 From the International Searching Authority Re. Application No. PCT/IB2006/002955.
Invitation Pursuant to Article 94(3) and Rule 71(1) EPC dated Dec. 19, 2013 From the European Patent Office Re. Application No. 10170623.2.
Notice of Refusal dated May 19, 2014 From the Israel Patent Office Re. Application No. 211022.
Notice of the Reason for Rejection dated May 13, 2013 From the Korean Intellectual Property Office Re. Application No. 10-2008-7010935.
Notification of Grounds for Rejection dated Aug. 16, 2011 From the Japanese Patent Office Re. Application No. 2008-519139 and Its Translation Into English.
Notification of Grounds for Rejection dated Oct. 25, 2011 From the Japanese Patent Office Re. Application No. 2008-535127 and Its Translation Into English.
Notification of Office Action dated Oct. 24, 2012 From the State Intellectual Property Office of the People's Republic of China Re. Application No. 200980132738.0.
Notification of the Decision to Grant a Patent Right for Patent for Invention dated Mar. 6, 2013 From the Patent Office of the People's Republic of China Re. Application No. 201010224944.9 and Its Translation Into English.

(56) References Cited

OTHER PUBLICATIONS

Notification of the Decision to Grant a Patent Right for Patent for Invention dated Apr. 20, 2010 From the Patent Office of the People's Republic of China Re. Application No. 200580020733.0 and Its Translation Into English.
Office Action and Search Report dated Apr. 2, 2013 From the State Intellectual Property Office of the People's Republic of China Re. Application No. 201210018835.0 and Its Translation Into English.
Office Action and Search Report dated Aug. 4, 2014 From the State Intellectual Property Office of the People's Republic of China Re. Application No. 201310193577.4 and Its Translation Into English.
Office Action and Search Report dated Aug. 31, 2012 From the State Intellectual Property Office of the People's Republic of China Re. Application No. 201010224944.9 and Its Translation Into English.
Office Action dated Sep. 2, 2014 From the State Intellectual Property Office of the People's Republic of China Re. Application No. 201210018835.0 and Its Translation Into English.
Office Action dated Mar. 5, 2012 From the Israel Patent Office Re. Application No. 178738.
Office Action dated Mar. 5, 2012 From the Israel Patent Office Re. Application No. 211022.
Office Action dated Jun. 6, 2012 From the Israel Patent Office Re. Application No. 211023.
Office Action dated Mar. 6, 2012 From the State Intellectual Property Office of the People's Republic of China Re. Application No. 200680032507.9 and Its Translation Into English.
Office Action dated Oct. 8, 2012 From the State Intellectual Property Office of the People's Republic of China Re. Application No. 200680047235.X and Its Translation Into English.
Office Action dated Nov. 9, 2009 From the Israel Patent Office Re. Application No. 178738.
Office Action dated Aug. 12, 2011 From the State Intellectual Property Office of the People's Republic of China Re. Application No. 200680032507.9 and Its Translation Into English.
Office Action dated Jan. 12, 2012 From the State Intellectual Property Office of the People's Republic of China Re. Application No. 201010224944.9 and Its Translation Into English.
Office Action dated Jun. 12, 2009 From the State Intellectual Property Office of the People's Republic of China Re. Application No. 200580020733.0 and Its Translation Into English.
Office Action dated Apr. 13, 2015 From the State Intellectual Property Office of the People's Republic of China Re. Application No. 201310193577.4 and Its Translation Into English.
Office Action dated Mar. 17, 2011 From the Israel Patent Office Re. Application No. 178738.
Office Action dated Jun. 23, 2011 From the State Intellectual Property Office of the People's Republic of China Re. Application No. 201010224944.9 and Its Translation Into English.
Office Action dated Oct. 23, 2009 From the State Intellectual Property Office of the People's Republic of China Re. Application No. 200680032507.9 and Its Translation Into English.
Office Action dated Dec. 24, 2013 From the State Intellectual Property Office of the People's Republic of China Re. Application No. 201210018835.0 and Its Translation Into English.
Office Action dated Oct. 25, 2011 From the State Intellectual Property Office of the People's Republic of China Re. Application No. 200680047235.X and Its Translation Into English.
Official Action dated Dec. 5, 2011 From the US Patent and Trademark Office Re. U.S. Appl. No. 12/901,535.
Official Action dated Dec. 8, 2009 From the US Patent and Trademark Office Re. U.S. Appl. No. 11/587,179.
Official Action dated May 12, 2015 From the US Patent and Trademark Office Re. U.S. Appl. No. 13/522,717.
Official Action dated Aug. 18, 2010 From the US Patent and Trademark Office Re. U.S. Appl. No. 12/083,436.
Official Action dated Jul. 19, 2012 From the US Patent and Trademark Office Re. U.S. Appl. No. 12/083,436.
Official Action dated Apr. 20, 2015 From the US Patent and Trademark Office Re. U.S. Appl. No. 13/497,055.
Official Action dated May 20, 2011 From the US Patent and Trademark Office Re. U.S. Appl. No. 12/083,436.
Official Action dated Dec. 21, 2012 From the US Patent and Trademark Office Re. U.S. Appl. No. 13/001,433.
Official Action dated Sep. 26, 2014 From the US Patent and Trademark Office Re. U.S. Appl. No. 13/497,055.
Requisition by the Examiner dated Feb. 7, 2015 From the Canadian Intellectual Property Office Re. Application No. 2,563,657.
Requisition by the Examiner dated Mar. 19, 2013 From the Canadian Intellectual Property Office Re. Application No. 2,613,713.
Restriction Official Action dated May 13, 2009 From the US Patent and Trademark Office Re. U.S. Appl. No. 11/587,179.
Restriction Official Action dated Mar. 17, 2013 From the US Patent and Trademark Office Re. U.S. Appl. No. 13/522,717.
Restriction Official Action dated Jan. 20, 2011 From the US Patent and Trademark Office Re. U.S. Appl. No. 12/306,934.
Restriction Official Action dated Jan. 21, 2011 From the US Patent and Trademark Office Re. U.S. Appl. No. 12/306,933.
Restriction Official Action dated Oct. 25, 2012 From the US Patent and Trademark Office Re. U.S. Appl. No. 13/001,433.
Statement of Opinion dated Sep. 10, 2013 From the Korean Intellectual Property Office Re. Application No. 10-2008-7001219 and Its Translation Into English.
Supplementary European Search Report and the European Search Opinion dated Nov. 8, 2013 From the European Patent Office Re. Application No. 06809092.7.
Supplementary European Search Report and the European Search Opinion dated Sep. 16, 2011 From the European Patent Office Re. Application No. 09773059.2.
Supplementary Partial European Search Report and the European Search Opinion dated Nov. 19, 2009 From the European Patent Office Re. Application No. 07766875.4.
Translation of Notice of Reasons for Rejection dated Dec. 14, 2010 From the Japanese Patent Office Re. Application No. 2007-509059.
Translation of Office Action dated Sep. 19, 2010 From the State Intellectual Property Office of the People's Republic of China Re. Application No. 200680032507.9.
Translation of Office Action dated Jan. 21, 2013 From the State Intellectual Property Office of the People's Republic of China Re. Application No. 200680032507.9.
Translation of Rejection Decision dated Aug. 31, 2012 From the State Intellectual Property Office of the People's Republic of China Re. Application No. 200680032507.9.
International Search Report and the Written Opinion dated Nov. 30, 2017 From the International Searching Authority Re. Application No. PCT/IL2017/050911. (12 Pages).
Notification of Office Action dated Feb. 5, 2018 From the State Intellectual Property Office of the People's Republic of China Re. Application No. 201380071889.6 and Its Translation Into English. (8 Pages).
Notice of Reason for Rejection dated Mar. 13, 2018 From the Japan Patent Office Re. Application No. 2015-546149 and Its Machine Translation Into English. (2 Pages).

* cited by examiner

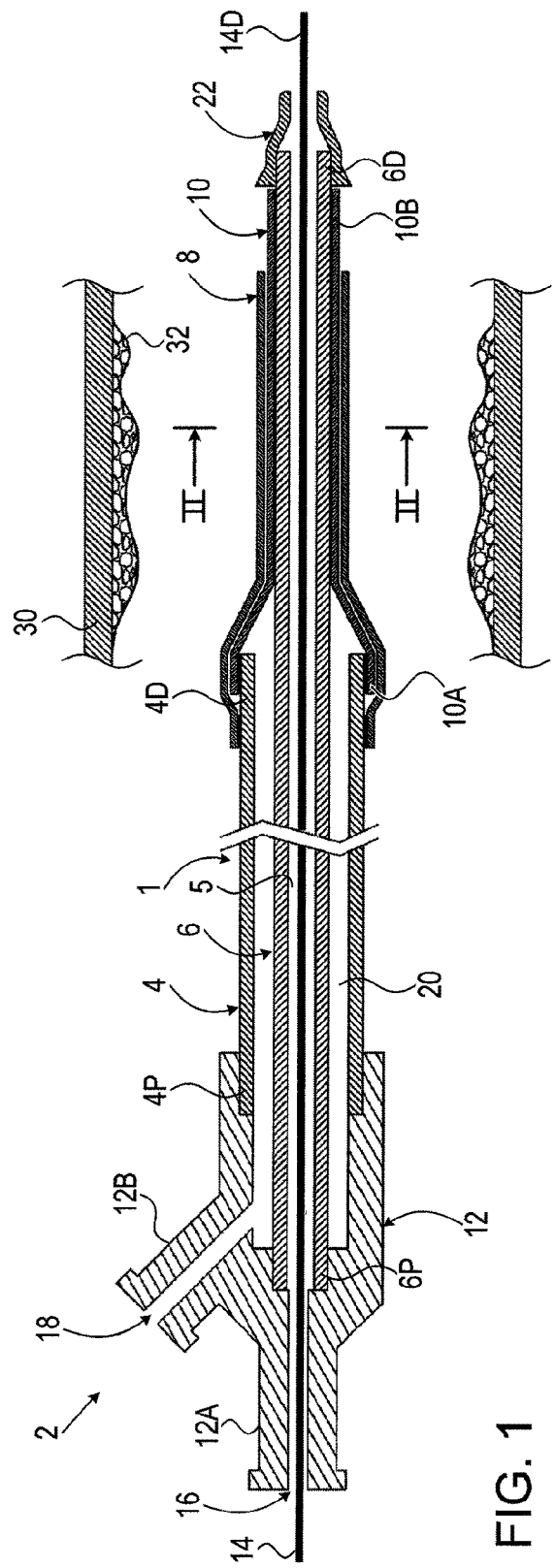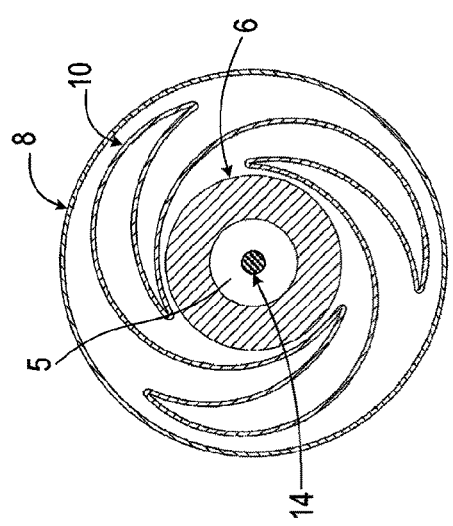
FIG. 1
FIG. 2

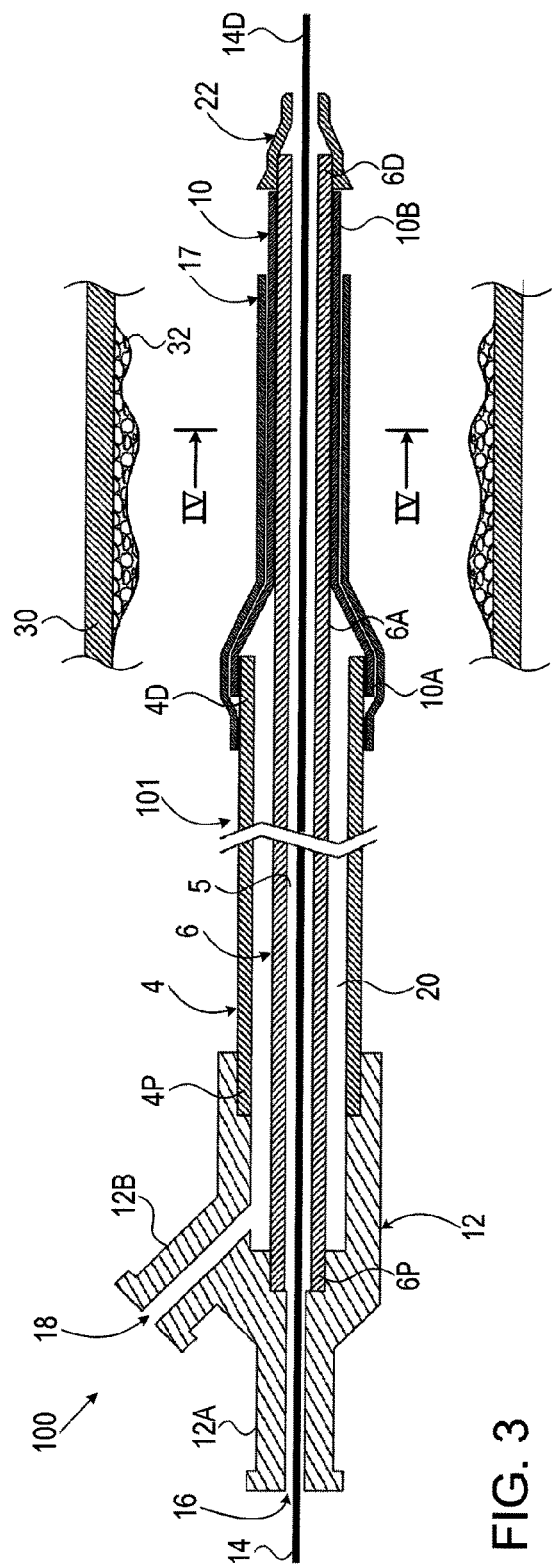
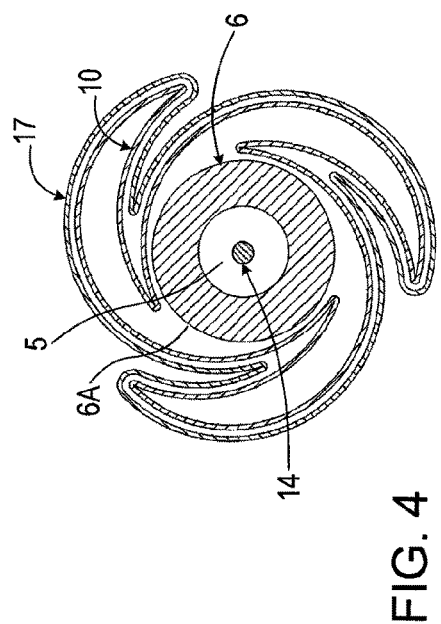
FIG. 3
FIG. 4

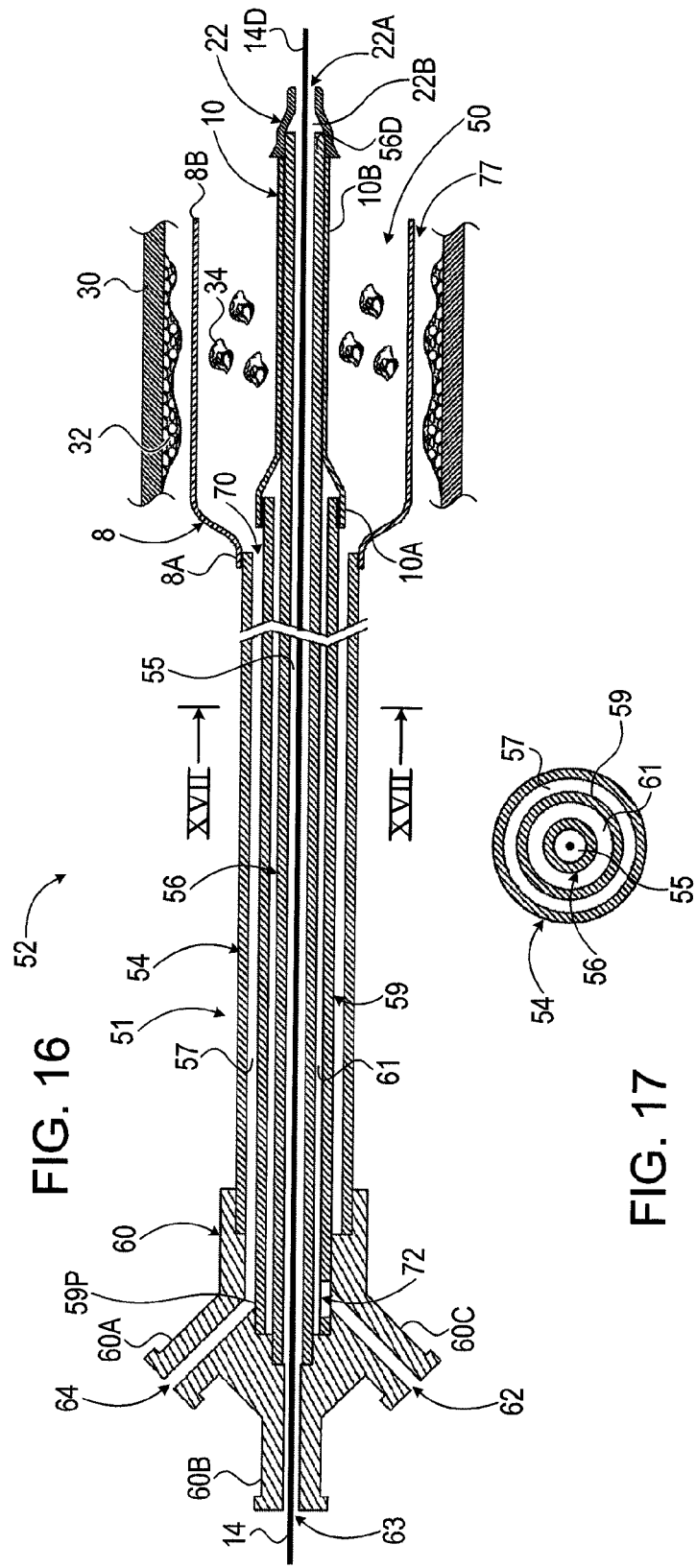

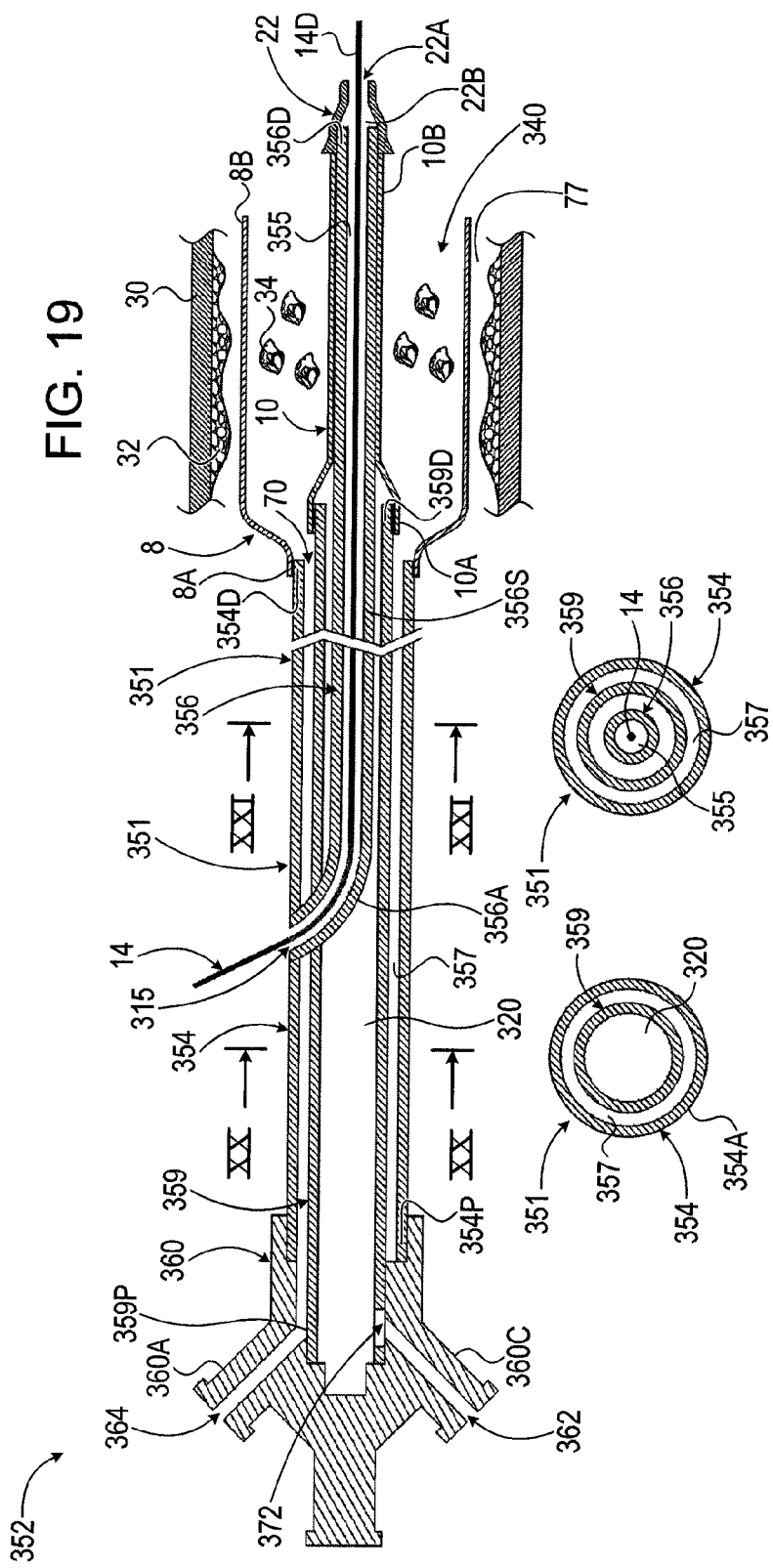

BALLOON CATHETER AND METHODS OF USE THEREOF

CROSS-REFERENCE TO RELATED APPLICATIONS

This application is a continuation of International Application No. PCT/IL2013/000089, which has an international filing date of Dec. 4, 2013, and which claims the benefit of U.S. Provisional Patent Application No. 61/732,944, filed on Dec. 4, 2012, the disclosure of which is incorporated herein by reference.

FIELD OF THE INVENTION

This invention relates in general to the field of medical catheters having inflatable balloons and more particularly to catheters having a balloon with an open sleeve.

BACKGROUND OF THE INVENTION

Catheters are used in various interventional procedures for delivering therapeutic means to a treated site (e.g., body organ or passageway such as blood vessels). In many cases, a catheter with a small distal inflatable balloon is guided to the treated site. Once the balloon is in place it is inflated by the operator for affixing it in place, for expanding a blocked vessel, for placing treatment means (e.g., stent) and/or for delivering surgical tools (e.g. knives, drills etc.) to a desired site. In addition, catheter systems have also been designed and used for retrieval of objects such as stents from body passageways.

Rapid-exchange catheters have been developed for intravascular use and are routinely used for angioplastic treatment of stenosed vessels in patients.

Rapid exchange ("monorail" or RE) catheters typically comprise a relatively short guide wire lumen provided in a distal section thereof, and a proximal guide wire exit port located between the catheter's distal and proximal ends. This arrangement allows exchange of the catheter over a relatively short guide wire, in a manner which is simple to perform and which can be carried out by a single operator. Rapid exchange catheters have been extensively described in the art, for example, in U.S. Pat. Nos. 4,762,129, 4,748,982 and EP0380873.

Rapid exchange catheters are commonly used in Percutaneous Transluminal Coronary Angioplasty (PTCA) procedures, in which obstructed blood vessels are typically dilated by a distal balloon mounted on the catheter's distal end. A stent is often placed at the vessel's dilation zone to prevent reoccurrences of obstruction therein. The dilation balloon is typically inflated via an inflation lumen which extends longitudinally inside the catheter's shaft between the dilation balloon and the catheter's proximal end.

Published International Application Nos. WO 2005/102184 discloses a catheter having a rollable expandable element. Published International applications, WO 2007/004221, WO 2007/042935, WO 2008/004238 and WO 2008/004239, all five published international applications are incorporated herein by reference in their entirety for all purposes, disclose various types of catheters and catheter systems having intussuscepting balloon-like inflatable members which may be used, inter alia, to treat plaque by balloon inflation while efficiently and safely collecting plaque debris and other particulate matter from the lumen of pathologically-involved blood vessels and to remove such particles and particulate matter from the blood vessel.

WO 2008/004238 discloses several types of rapid exchange catheters having an intussuscepting balloon-like inflatable member which may be used for treating plaque in stenosed vessels and for collecting and for removing from the body plaque debris and other particulate matter resulting from the distention of the vessel wall and the compaction of plaque during the inflating of the balloon within the blood vessel.

While the various types of rapid exchange catheters with intussuscepting balloons disclosed in WO 2008/004238 may be efficiently and safely used for treating patients, their construction is based on the use of a segmented tubular inner conduit having several segments. Some segments of the inner conduit are slidably disposed within other segments of the inner conduit in order to enable the distal part of the inner conduit to move proximally during the intussuscepting of the balloon. In order to keep the segmented inner conduit sealed, WO 2008/004238 discloses the use of sealing gaskets designed to withstand the inflation pressure of the balloons. While sealing gaskets are well known in the art their use may pose several technical difficulties, due mainly to the fact that the implementation of sealing gaskets may require expensive and time consuming construction techniques as well as the use of time consuming and expensive testing and quality control procedures. This is especially challenging when the diameters of inner conduit and of the necessary gaskets are relatively small.

While the cavity forming intussuscepting balloons are quite efficient for trapping debris and/or particulate matter or secretions from the treated site, the construction of a movable inner conduit that slides within an outer conduit and the operation of mechanisms to move the inner conduit as combined with an intussuscepting balloon are fairly complex and require expertise to construct and to operate. In particular rapid exchange (monorail) catheters with intussuscepting balloons are not simple to construct.

International published applications WO 08/004238 and WO 08/004239 disclosed a sleeve collecting device having a tube with a sleeve suitable for passage of a debris collecting catheter therethrough. However, such sleeve devices are separate from the debris collecting catheter, require the handling and operating of two separate devices (a sleeve collecting device and a separate debris collecting catheter which is separate from the sleeve device that are longitudinally or axially freely movable relative to each other). The debris collecting catheter is based on an intussuscepting balloon which is first inserted through the lumen of the sleeve device and then operated at the treatment site and only after the capturing of the debris by the catheter the catheter is withdrawn proximally to enter the sleeve of the separate sleeve device.

U.S. Pat. No. 5,092,839 to Kipperman discloses a system including an angioplastic balloon catheter which is movably disposed within a hollow thrombectomy catheter. The thrombectomy catheter has a distal end which may be expanded by inflating the balloon catheter. However, the balloon catheter is axially (longitudinally) movable with respect to the thrombectomy catheter and the system requires moving the balloon catheter distally outside of the thrombectomy catheter in order to perform angioplasty on the lesion followed by proximal movement of the balloon catheter into the thrombectomy catheter in order to collect debris.

There is therefore a need for simple and efficient catheters capable of collecting debris and particulate matter and/or secretions at a treatment site in a body cavity.

BRIEF DESCRIPTION OF THE DRAWINGS

The invention is herein described, by way of example only, with reference to the accompanying drawings, in which like components are designated by like reference numerals, wherein:

FIG. 1 is a schematic cross-sectional diagram illustrating an over the wire balloon catheter having a balloon and a sleeve, in accordance with an embodiment of the catheter of the present application;

FIG. 2 is a schematic cross-section of the catheter of FIG. 1 taken along the lines II-II;

FIG. 3 is a schematic cross-sectional diagram illustrating an over the wire balloon catheter having a balloon and a sleeve, in accordance with another embodiment of the catheter of the present application;

FIG. 4 is a schematic cross-section of the catheter of FIG. 3 taken along the lines IV-IV;

FIG. 16 is a schematic cross-sectional diagram illustrating a multi-conduit, multi-lumen balloon catheter having three conduits and three hollow passages, in accordance with an additional embodiment of the catheter of the present application;

FIG. 17 is a schematic cross-section of the catheter of FIG. 16 taken along the lines XVII-XVII;

FIG. 19 is a cross-sectional diagram illustrating a rapid exchange multi-lumen catheter having a three conduit shaft, a sleeve and a balloon with three hollow passages formed within the catheter shaft, in accordance with another embodiment of the catheter of the present application;

FIG. 20 is a schematic cross-section of the catheter of FIG. 19 taken along the lines XX-XX;

FIG. 21 is a schematic cross-section of the catheter of FIG. 19 taken along the lines XXI-XXI;

SUMMARY OF THE INVENTION

Figure 5:
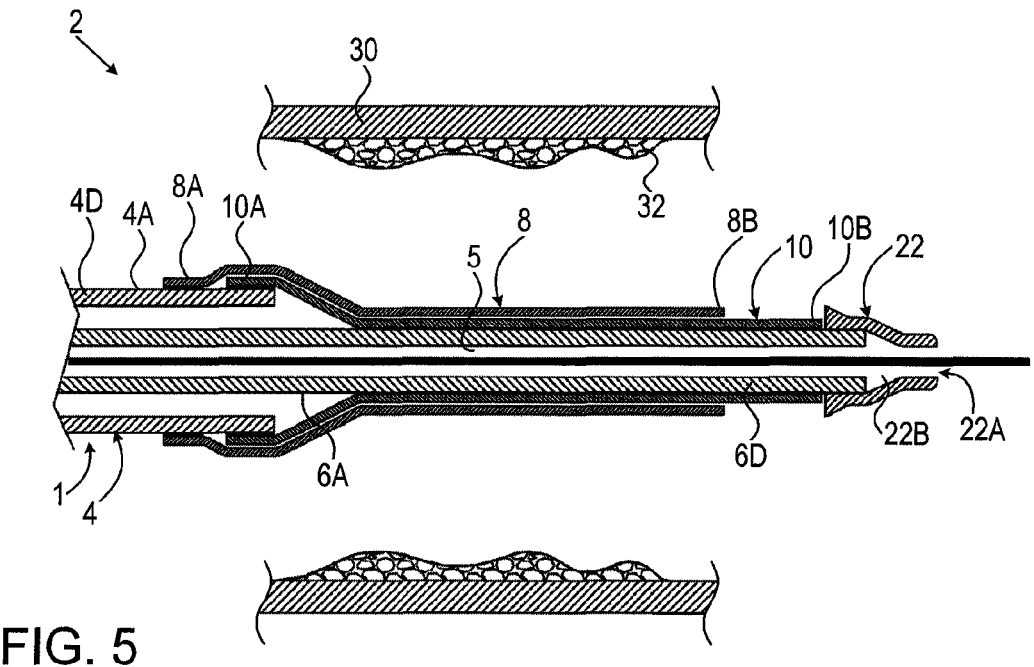
FIGS. 5-7 are schematic cross-sectional diagrams of part of the catheter of FIG. 1 illustrated at three different stages of operating the catheter.

There is therefore provided, in accordance with an embodiment of the catheters of the present application, a balloon catheter including a catheter shaft, an inflatable balloon attached to the catheter shaft and an open sleeve having a proximal end sealingly attached to the catheter shaft and an open distal end, the sleeve surrounds at least part of the balloon. The sleeve and the balloon are arranged such that inflating the balloon expands the sleeve into an expanded state and deflating the balloon when the sleeve is in the expanded state forms an open cavity between the sleeve and the deflated balloon and creates suction to capture and retain debris within the cavity.

Furthermore, in accordance with an embodiment of the catheters of the present applications, the cavity is selected from an annular cavity and a non-regular annular cavity.

Furthermore, in accordance with an embodiment of the catheters of the present application, the catheter also includes a deployable stent disposed on the sleeve.

Furthermore, in accordance with an embodiment of the catheters of the present application, the catheter is an over the wire catheter, and the catheter shaft includes a hollow outer conduit having a distal end, a proximal end and a lumen. The catheter shaft also includes a hollow inner conduit, suitable for passage over a guide wire. The inner conduit has a distal part, a proximal part and a lumen. The inner conduit is disposed within the lumen of the outer conduit and positioned such that the distal end of the distal part of the inner conduit extends beyond the distal end of the outer conduit at all times during the operation of the catheter within the body. The proximal end of the balloon is sealingly attached to the distal end of the outer conduit and the distal end of the balloon is sealingly attached to the distal end of the inner conduit. The proximal end of the sleeve is sealingly attached to the distal end of the outer conduit of the catheter shaft. The catheter includes a fluid port fluidically communicating with the lumen of the outer conduit for introducing and withdrawing an inflation fluid into the inflatable balloon, and a guide-wire port disposed at the distal end of the catheter. The guide-wire port has an opening suitable for inserting a guide into the lumen of the inner conduit.

Furthermore, in accordance with an embodiment of the catheters of the present application, the catheter is a rapid exchange catheter and the catheter shaft includes a hollow outer conduit having a distal end, a proximal end and a lumen. The catheter shaft also includes a hollow inner conduit, suitable for passage over a guide wire. The inner conduit has an angled proximal part that is fixedly attached to the wall of the outer conduit and sealingly pierces the wall of the outer conduit to form an opening in the outer conduit for inserting a guide-wire therethrough. The inner conduit also has a straight distal part and a lumen. The inner conduit is disposed within the lumen of the outer conduit and positioned such that the distal end of the distal part of the inner conduit extends beyond the distal end of the outer conduit. The inflatable balloon has a proximal end and a distal end. The proximal end of the balloon is sealingly attached to the distal end of the outer conduit and the distal end of the balloon is sealingly attached to the distal end of the inner conduit. The proximal end of the sleeve is sealingly attached to the distal end of the outer conduit. The catheter includes a fluid port in fluidic communication with the lumen of the outer conduit for introducing and withdrawing an inflation fluid into the inflatable balloon.

Furthermore, in accordance with an embodiment of the catheters of the present application, the catheter shaft includes at least three fluidically separate hollow passages therein. The hollow passages include a first hollow passage for inserting a guide wire therethrough, a second hollow passage for inserting inflation fluid into the balloon and for withdrawing inflation fluid from the balloon, and a third hollow passage fluidically connected to the cavity between the balloon and the sleeve. Suction from an external suction source may be applied to the cavity through the third hollow passage to assist the capturing and retaining of the debris within the cavity or within the third hollow passage.

Furthermore, in accordance with an embodiment of the catheters of the present application, the catheter shaft includes a first conduit, a second conduit and a third conduit. The first conduit is disposed within the second conduit such that the distal end of the third conduit extends distally beyond the distal end of the second conduit. The first hollow passage is the lumen of the first conduit. The second conduit is disposed within the lumen of the third conduit such that the annular space defined between the outer side of the second conduit and the inner side of the third conduit is the third hollow passage. The proximal end of the sleeve is sealingly attached to the third conduit. The proximal end of the balloon is sealingly attached to the distal end of the second conduit. The distal end of the balloon is sealingly attached to the distal end of the first conduit that protrudes beyond the distal end of the second conduit.

Furthermore, in accordance with an embodiment of the catheters of the present application, the proximal end of the catheter includes a fluid port fluidically communicating with the third passage for applying suction to the third passage and for injecting a contrast enhancing fluid therethrough into the body cavity. The proximal end of the catheter also includes an inflation port fluidically communicating with the second passage for inflating and deflating the balloon and a guide wire port for inserting a guide wire into the first hollow passage.

Furthermore, in accordance with an embodiment of the catheters of the present application, the catheter shaft includes an inner conduit, an intermediate conduit and an outer conduit. The inner conduit is disposed within the intermediate conduit and the intermediate conduit is disposed within the outer conduit such that the distal end of the inner conduit extends distally beyond the distal end of the intermediate conduit. The inner conduit has a straight distal part that protrudes distally beyond the distal end of the intermediate conduit and an angled proximal part that sealingly pierces through the wall of the intermediate conduit and also sealingly pierces through the wall of the outer conduit to form an opening in the outer conduit for inserting a guide-wire therethrough. The first hollow passage is the lumen of the inner conduit. The second hollow passage is the space between the inner conduit and the intermediate conduit. The intermediate conduit is disposed within the lumen of the outer conduit such that the space defined between the intermediate conduit and the outer conduit is the third hollow passage. The proximal end of the sleeve is sealingly attached to the distal end of the outer conduit. The proximal end of the balloon is sealingly attached to the distal end of the intermediate conduit and the distal end of the balloon is sealingly attached to the distal end of the inner conduit that protrudes beyond the distal end of the intermediate conduit.

Furthermore, in accordance with an embodiment of the catheters of the present application, the proximal end of catheter includes a fluid port fluidically communicating with the third passage for applying suction to the third passage and for injecting a contrast enhancing fluid therethrough into the body cavity. The proximal end of the catheter also includes an inflation port fluidically communicating with the second passage for inflating and deflating the balloon. The opening in the wall of the outer conduit accessing the lumen of the inner conduit is disposed between the proximal end and the distal end of the wall of the outer conduit.

Furthermore, in accordance with an embodiment of the catheters of the present application, the sleeve is selected from the group consisting of, a sleeve having a distal end that extends distally beyond the distal end of the balloon when the balloon is in the deflated state, a sleeve having a distal end that extends distally along the catheter shaft to the same longitudinal position of the distal end of the balloon when the balloon is in the deflated state, and a sleeve having a distal end such that the distal end of the balloon extends distally beyond the distal end of the sleeve when the balloon is in the deflated state.

Furthermore, in accordance with an embodiment of the catheters of the present applications, the sleeve is selected from the group consisting of, a sleeve having a distal end that extends distally beyond the distal end of the balloon when the balloon is in the inflated state, a sleeve having a distal end that extends distally to the same longitudinal position of the distal end of the balloon when the balloon is in the inflated state, and a sleeve having a distal end such that the distal end of the balloon extends distally beyond the distal end of the sleeve when the balloon is in the inflated state.

Furthermore, in accordance with an embodiment of the catheters of the present application, the catheter also includes a sleeve supporting member disposed between the balloon and the sleeve to support the sleeve in the expanded state after the balloon is deflated.

Furthermore, in accordance with an embodiment of the catheters of the present application, the sleeve supporting member is selected from a sleeve supporting member having a distal end co-extending to the same distance of the distal end of the sleeve when the sleeve is in the expanded state, a sleeve supporting member having a distal end such that the distal end of the sleeve extends distally beyond the distal end of the sleeve supporting member when the sleeve is in the expanded state, and a sleeve supporting member having a distal end such that the distal end of the sleeve supporting member extends distally beyond the distal end of the sleeve when the sleeve is in the expanded state.

Furthermore, in accordance with an embodiment of the catheters of the present application, the sleeve supporting member is selected from an expandable elastic member, a compressed elastic member, an expandable spring-like member, a compressed spring-like member, a coiled member, a compressed elastic coiled member, and a helically coiled member.

Furthermore, in accordance with an embodiment of the catheters of the present application, the sleeve is a perforated sleeve having perforations therein and the catheter also includes a substance disposed between the sleeve and the balloon such that upon inflating the balloon, at least a portion of the substance is extruded through the perforation and is applied to the wall of a body cavity within which the catheter is disposed.

Furthermore, in accordance with an embodiment of the catheters of the present application, the perforations have opening dimensions in the range between 0.001-0.5 millimeter.

Furthermore, in accordance with an embodiment of the catheters of the present applications, the perforations are selected from perforations having circular cross sections and perforations having non-circular cross sections.

Furthermore, in accordance with an embodiment of the catheters of the present application, the substance includes one or more materials selected from, a therapeutic substance, a diagnostic substance, a drug, a therapeutic composition, a medicament, a diagnostic composition, a physiologically active agent, a biochemically active agent, one or more living cells, DNA, RNA, a nucleic acid, a vector for delivering genetic material to cells in the treated site, an anti-inflammatory agent, an anti-restenosis agent, a cell proliferation inhibitory agent, a smooth muscle proliferation inhibiting agent, paclitaxel, rapamycin, everolimus, a vasoactive agent, a vaso dilating agent, a vaso constricting agent, an antibiotic agent, an anti-coagulative agent, a platelet aggregation inhibiting agent, an anti-fibrosis agent, a pharmaceutically acceptable vehicle, a lipid based vehicle, and any combinations thereof.

Furthermore, in accordance with an embodiment of the catheters of the present application, the perforated sleeve includes a material having a sponge-like structure with open cavities allowing extrusion of the substance to the outer surface of the sleeve when the balloon is inflated.

Furthermore, in accordance with an embodiment of the catheters of the present application, the catheter also includes a soft tip attached to the catheter shaft at its distal end.

Furthermore, in accordance with an embodiment of the catheters of the present application, the soft tip includes a retaining member for securing the distal end of one or more of the balloon and the sleeve during insertion of the catheter into a body cavity and during moving the distal end of the catheter towards the treatment site in the cavity.

Furthermore, in accordance with an embodiment of the catheters of the present application, prior to inflating the balloon the sleeve has a circular cross-section and the balloon is folded around a portion of the catheter shaft prior to inflating the balloon.

Furthermore, in accordance with an embodiment of the catheters of the present application, both the sleeve and the balloon are folded around a portion of the catheter shaft prior to inflating the balloon to reduce the crossing profile of the catheter.

Furthermore, in accordance with an embodiment of the catheters of the present application, the balloon is folded around a portion of the catheter shaft prior to inflating the balloon, and wherein the sleeve is folded over the balloon to reduce the crossing profile of the catheter.

Furthermore, in accordance with an embodiment of the catheters of the present application, the sleeve comprises a material selected from a compliant material, a semi-compliant material, a non-compliant material, a stretchable material, a non-stretchable material, an annealed stretchable material, a pre-stretched non-stretchable material that has undergone molecular orienting by biaxial orienting processes, and any combinations thereof.

Furthermore, in accordance with an embodiment of the catheters of the present application, the sleeve includes a material selected from a polymer based material, Nylon® Nylon 12®, PET, a polyamide PA12, Grilamid® L25, Grilamid® L55, PA11, Polyether block amides PEBAX® 7233, PEBAX®7033, PEBAX® 6333), Grilflex® ELG 6260, Polyester, polyethylene, polyurethane, and any combinations thereof.

Furthermore, in accordance with an embodiment of the catheters of the present application, the catheter also includes one or more devices selected from the group consisting of, one or more radio-opaque markers attached to the catheter shaft and one or more position detection assisting devices attached to one or more parts of the catheter for enabling a three dimensional catheter positioning system to determine the position of at least part of the catheter in a reference frame defined in three dimensional space.

Furthermore, in accordance with an embodiment of the catheters of the present application, the balloon is selected from the group consisting of a cylindrical balloon having conical or tapering ends, a stepped balloon having two or more cylindrical portions having different diameters of at least some of the cylindrical portions, a balloon having a conical or truncated conical longitudinal cross-sectional shape, a balloon having a tapering longitudinal cross-sectional shape, a balloon having a non-linearly varying longitudinal cross sectional shape, a balloon having at least one corrugated portion, a balloon having a uniform wall thickness, and a balloon having a non-uniform wall thickness.

There is also provided, in accordance with an embodiment of the methods of the present application, a method for treating a body cavity. The method includes the steps of inserting the catheter into the body cavity, positioning the sleeve at a treatment site of the cavity, inflating the balloon to expand the sleeve to an expanded state, and deflating the balloon to form an open cavity between the expanded sleeve and the balloon, such that the deflating generates suction that captures and retains debris and/or particulate matter within the cavity.

Furthermore, in accordance with an embodiment of the method of the present application, the step of inserting comprises inserting the catheter into the body cavity over a guide wire passing through a hollow passage formed within the catheter shaft.

Furthermore, in accordance with an embodiment of the method of the present application, the body cavity is a blood vessel.

Furthermore, in accordance with an embodiment of the method of the present application, the step of inflating the balloon also opens an occlusion in the blood vessel.

Furthermore, in accordance with an embodiment of the method of the present application, the catheter also includes a sleeve supporting member disposed between the balloon and the sleeve and the step of inflating the balloon also includes a step selected from expanding the sleeve supporting member by the balloon to an expanded state for supporting the expanded state of the sleeve, and allowing the sleeve supporting member to expand from an initially compressed state to an expanded state for supporting the expanded state of the sleeve.

Furthermore, in accordance with an embodiment of the method of the present application, the sleeve is a perforated sleeve and the catheter also includes a substance disposed between the balloon and the perforated sleeve. The step of inflating the balloon also includes the step of applying the substance to a site in the body cavity by extruding the substance through perforations in the perforated sleeve to apply a portion of the substance to part of the body cavity.

Furthermore, in accordance with an embodiment of the method of the present application, the catheter also includes a stent disposed on the outer surface of the sleeve and the step of inflating the balloon also includes the step of expanding the stent to deploy the stent in the treated body cavity.

Furthermore, in accordance with an embodiment of the method of the present application, the catheter shaft includes a hollow passage fluidically connected to the cavity formed between the balloon and the sleeve and the method also includes the step of applying suction to the cavity from an external suction source through the hollow passage to assist the capturing and the retaining of debris within the cavity of the catheter.

Furthermore, in accordance with an embodiment of the method of the present application, the step of applying suction also comprises the step of capturing and retaining at least some of the debris within the hollow passage connected to the cavity.

Furthermore, in accordance with an embodiment of the method of the present application, the catheter shaft comprises at least three fluidically separate hollow passages therein. The first hollow passage has a first opening disposed on the catheter shaft for inserting a guide wire there through and a second opening disposed at the distal end of the catheter shaft for allowing the guide wire to exit through the second opening. The catheter shaft includes a second hollow passage for inserting and withdrawing inflation fluid into and from the balloon, respectively, and a third hollow passage fluidically connected to the cavity between the balloon and the sleeve through the third hollow passage. The method also includes the step of applying suction from an external suction source to the cavity through the third hollow passage, to assist the capturing and the retaining of the debris within the cavity or within the third hollow passage.

Furthermore, in accordance with an embodiment of the method of the present application, the method also includes the step of inserting through a hollow passage of the shaft a device selected from a diagnostic device for performing a diagnostic procedure within the body cavity and a therapeutic device for performing a therapeutic procedure in the body cavity.

Furthermore, in accordance with an embodiment of the method of the present application, the device is inserted into the catheter through a hollow passage used for inserting a guide wire into the catheter and wherein the method also includes the step of withdrawing a guide wire from the hollow passage prior to inserting the device.

Furthermore, in accordance with an embodiment of the method of the present application, the method also includes the step of injecting a contrast enhancing agent through a hollow passage in the catheter shaft.

Finally, in accordance with an embodiment of the method of the present application, the step of inflating the balloon includes a step selected from the steps of, opening the sleeve by the balloon, unfolding the sleeve by the balloon, expanding the sleeve by the balloon, stretching the sleeve by the balloon, and any combinations thereof.

DETAILED DESCRIPTION OF THE INVENTION

The device is herein described, by way of example only, with reference to the accompanying drawings. With specific reference now to the drawings in detail, it is stressed that the particulars shown are by way of example and for purposes of illustrative discussion of the preferred embodiments of the exemplary systems only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner—including any combination of features—any combination of features may be included in any embodiment and/or omitted from any embodiments.

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

Figure 10:
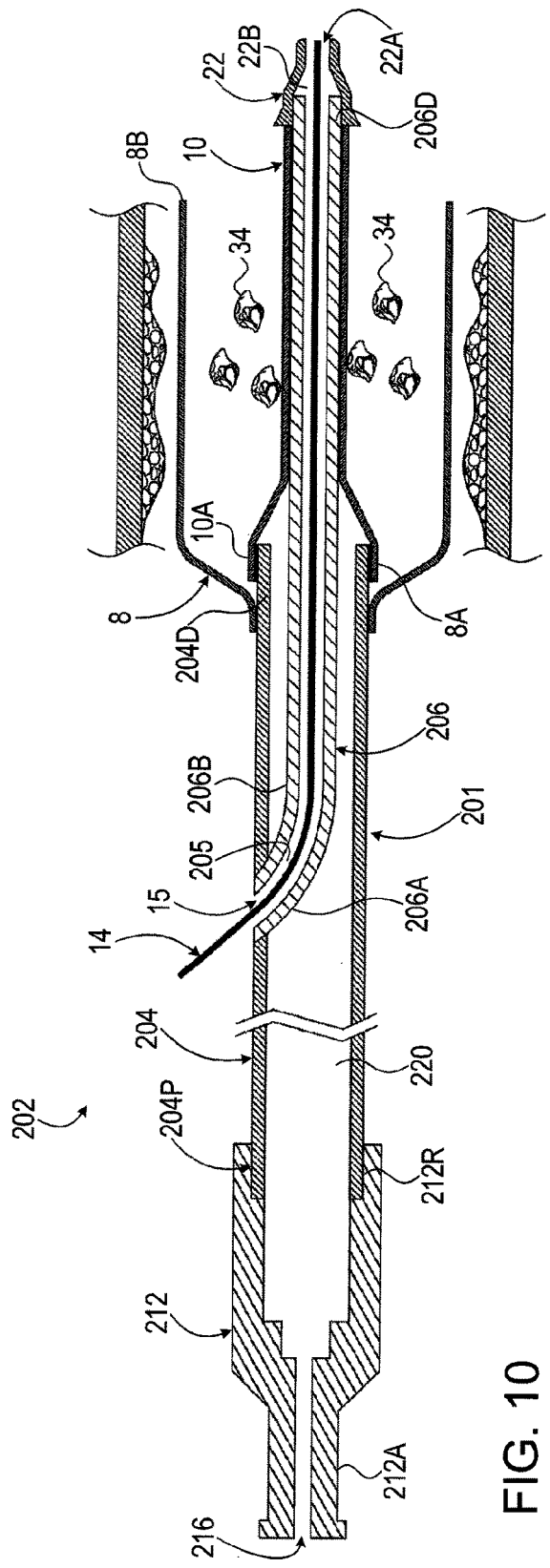
FIG. 10 is a schematic cross-sectional diagram illustrating a rapid exchange balloon catheter having a fixed non-movable angled inner conduit, a balloon and a sleeve, shown during a step in which the balloon is in a deflated state after being in an inflated state, in accordance with an embodiment of the rapid exchange catheters of the present application.

Some embodiments relate to a 'diameter' of an object or conduit—for example, a 'diameter' of a lumen of an outer conduit (for example, the diameter of the lumen 220 of the outer conduit 204 of FIG. 10). It is noted that for conduits having a circular cross-section, the term 'diameter' means the diameter of the circular lumen. However, for lumens or conduits having a non-circular cross-section, a 'diameter' is defined as the square root of the cross sectional area of the lumen or conduit.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to. The term "or" is used herein to mean, and is used interchangeably with, the term "and/or," unless context clearly indicates otherwise. The term "such as" is used herein to mean, and is used interchangeably with, the phrase "such as but not limited to".

The present device has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

In the following description and in the claims of the present application, the terms "distal" and "proximal" are defined as follows: the catheter side or catheter end which is inserted into the body first is referred to as the distal side or distal end and the other (trailing) side or end of the catheters is referred to as the proximal side. For example, in the balloon catheter 2 of FIG. 1, the connecting member 12 is attached to the proximal end of the catheter 2 and the balloon 10 is disposed at the distal side of the catheter 2.

In the following description and claims of the present application the terms "conduit" and "tube" may be interchangeably used to define an elongated hollow member having either a circular cross-section or a non-circular cross-section. While preferably, the conduits disclosed and illustrated herein have a circular cross-section, this is by no means obligatory for practicing the invention and the terms "conduit" and "tube" also include elongated hollow members having non-circular cross-sections, including, but not limited to, elongated hollow members having an ellipsoidal cross-section, a polygonal cross-section and an irregular cross-section.

Similarly, the term 'annular space' is used in the present application to describe a space defined by two hollow conduits such that a first (inner) conduit has a smaller diameter than the second (outer) conduit and the first conduit is disposed within the lumen of the second conduit. The term 'annular space' is defined as the space between the inner surface of the lumen of the second (larger diameter) conduit and the outer surface of the first (inner) conduit. As the present application contemplates and disclosed the use of conduits having a circular cross section as well as conduits having a non-circular cross-section (such as, but not limited to, ellipsoidal cross sections, irregular cross-sections and polygonal cross sections), all possible combinations and permutations of such cross-sections of the inner and outer conduits may be implemented in the catheters of the present application. For example, the term 'annular space" may apply to the space as defined hereinabove for a case in which both inner and outer conduit have a circular cross-section, for a case in which both the inner and outer conduit have a non-circular cross-section, and for a case in which one of the conduits has a circular cross-section while the other conduit has a non-circular cross-section. Similarly the space (cavity) formed between the sleeve and the balloon of the catheters disclosed hereinafter after deflating of the inflated balloon is generally termed an "annular space" or an "annular cavity" which term is also meant to include all types of cavities defined between the sleeve and the deflated balloon including spaces and cavities with a cross sections that are not perfectly annular due to the deflated balloon being crumpled and/or due to the cross section of the sleeve deviating from a circular shape.

The term "hollow passage" is used to refer to any type of open passage formed within the shaft of any of the catheters including any lumen or part of a lumen formed in a conduit that is part of the catheter's shaft, any space or passage formed between any two coaxially arranged conduits or tubes included in the catheter's shaft and any other open or hollow passage (having any type of cross sectional shape) that passes within the catheter's shaft or within a part of the catheter shaft.

The term "debris" as used throughout the specification and claims of the present application includes any type of particulate or non particulate material or object, including but not limited to, liquid secretions, gel-like material, solid and semi-solid particulate matter of any composition which may be present within the treated bodily cavity or blood vessel. Such debris may result from the treatment delivered by the catheter (including, for example, particles, liquid and/or semi-solid and/or gel-like secretions dislodged and released from an atheromatous plaque or from any other lesion and/or from the wall of the treated blood vessel during angioplastic procedures, or any other medical therapeutic or diagnostic procedures known in the art and performed in a blood vessel). The term "debris" also describes any object or substance which may be present in a body cavity or in the vasculature before insertion of a catheter to the body, such as, for example, a blood clot in the vasculature or a calculus (ureteral stone) in a urether and the like, and any other type of matter or substance or foreign object which is in need of removal from a bodily cavity or from the vasculature. Finally, the term "debris" may also include any type of secretion and/or object which needs to be collected and/or retrieved out of a body cavity for diagnostic and/or other purposes (for example, an ovum, or a secretion disposed within a duct and the like).

Reference is now made to FIGS. 1-2. FIG. 1 is a schematic cross-sectional diagram illustrating an over the wire balloon catheter having a balloon and a sleeve, in accordance with an embodiment of the catheters of the present application. FIG. 2 is a schematic cross-section of the catheter of FIG. 1 taken along the lines II-II (the guide wire 14 is not shown in FIG. 2).

FIG. 3 is a schematic cross-sectional diagram illustrating an over the wire balloon catheter having a balloon and a sleeve, in accordance with another embodiment of the catheters of the present application. FIG. 4 is schematic cross-section of the catheter of FIG. 3 taken along the lines IV-IV (the guide wire 14 is not shown in FIG. 4).

In the catheter 2 embodiment illustrated in FIGS. 1 and 2, the balloon 10 is in a folded configuration and is wrapped or folded around the inner conduit 6 of the catheter 2 and the sleeve 8 is not folded and is preferably (but not obligatorily) an open tubular portion having a circular cross-sectional shape which is disposed over the folded (wrapped) balloon 10.

In the catheter illustrated in FIGS. 3 and 4, the catheter 100 includes a catheter shaft 101 which includes the inner conduit 6 and the outer conduit 4. The catheter 100 also includes the balloon 10, a sleeve 17 and the connecting member 12. The balloon 10 is in a folded configuration and is wrapped or folded around the inner conduit 6 of the catheter 100. However, in contrast to the sleeve 8 of the catheter 2 which is not folded and has a cylindrical shape, the sleeve 17 of the catheter 100 is preferably (but not obligatorily) a tubular or cylindrical sleeve which is folded or wrapped over the folded (wrapped) balloon 10, such that both the balloon 10 and the sleeve 17 are folded and wrapped over the inner conduit 6 of the catheter 100 as best seen in FIG. 4. It is noted that in the cross-sectional view of FIG. 4, the folding of the balloon 10 and the sleeve 17 is illustrated in a relatively loose folding for the sake of clarity of illustration and that in the actual folded state thereof prior to insertion of the catheter 100 into the body, the folding or radial wrapping of the balloon 10 and the sleeve 17 around the outer surface 6A of the inner conduit 6 may be much tighter and less loose than the wrapping illustrated in FIG. 4 for illustrative purposes.

It is noted that, the two balloon and sleeve configurations described above (folded balloon with non-folded sleeve and folded balloon with folded sleeve) may be interchangeably used in all of the catheters of the present application, including all the over the wire (OVT) catheters described herein as well as all the rapid exchange (RE) catheters and all the multi-conduit and/or multi-lumen catheters disclosed in the present application.

Figure 6:
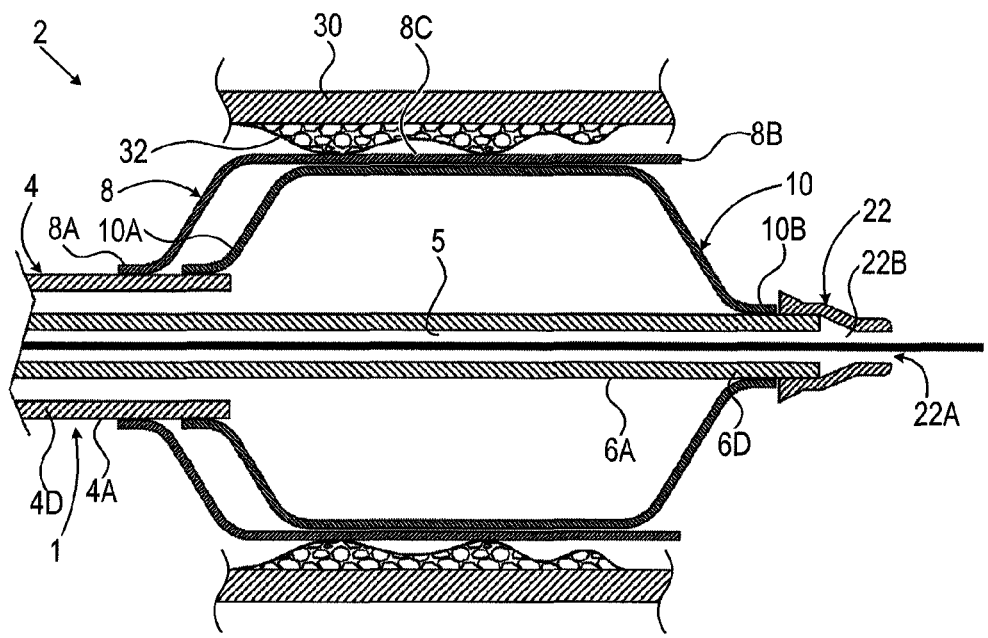
Figure 7:
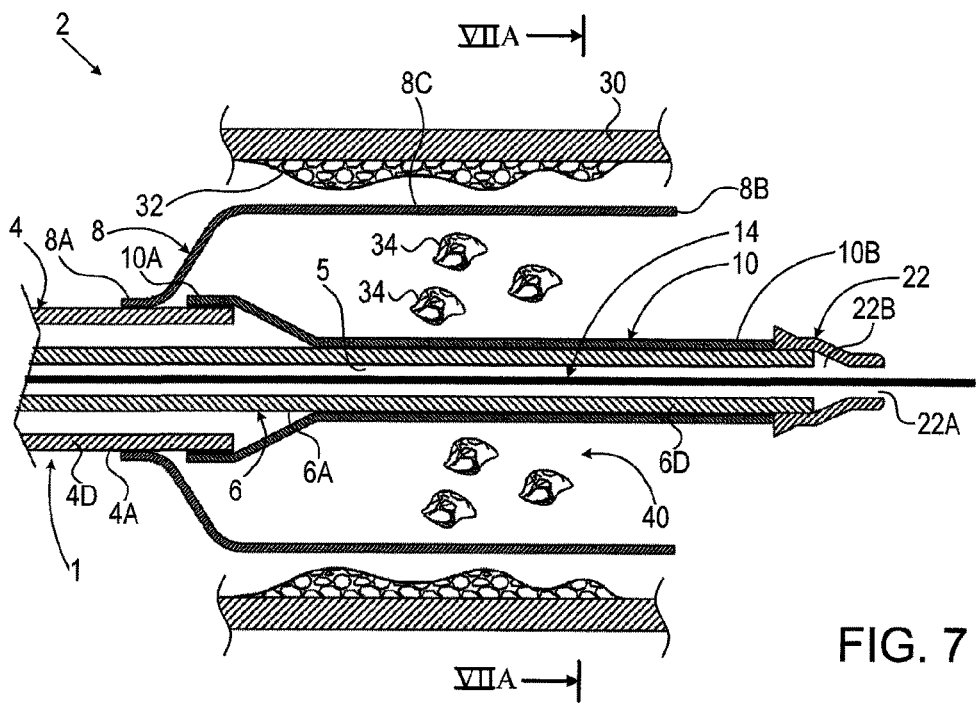

FIGS. 5-7 are schematic cross-sectional diagrams of part of the catheter 2 of FIG. 1 illustrated during three different stages of operating the catheter. FIG. 7 A is a schematic cross-section of the catheter of FIG. 7 taken along the lines VIIA-VIIA.

Turning to FIGS. 1 and 2, the catheter 2 includes a catheter shaft 1, an inflatable balloon 10, a sleeve 8 and a connector member 12. The shaft 1 includes an outer conduit 6 and an inner conduit 6 disposed within the outer conduit 4. The outer conduit 4 is preferably (but not obligatorily) a tubular conduit. The outer conduit 4 has a distal end 4D and a proximal end 4P. The inner conduit 6 is disposed within the lumen of the outer conduit 4. The inner conduit 6 is also preferably (but not obligatorily) a tubular conduit having an outer diameter smaller than the diameter of the lumen of the outer conduit 4. The inner conduit 6 has a distal end 6D and a proximal end 6P. The distal end 6D of the inner conduit 6 extends (protrudes) beyond the distal end 4D of the outer conduit 4. The inner conduit 6 and the outer conduit 4 may be made from flexible materials, such as but not limited to, Nylon®, Pebax®, polyurethane, Polyethyleneterephtalate (PET), stainless steel and the like. The proximal end 6P of the inner conduit 6 and the proximal end 4P of the outer conduit 4 are sealingly attached to the connector member 12 as illustrated in FIG. 1. The attachment of the proximal ends 6P and 4P to the connector member 12 may be done by bonding, thermal bonding, gluing or by any other attaching method known in the art. The connector member 12 may be made from any suitable material, including but not limited to, a polymer, a metal or an alloy and the like (such as, but not limited to, PEBAX, Stainless steel or any other suitable engineering plastic or polymer based structural material).

The connector member 12 has two hollow passages therein. A first hollow passage 16 opens into the lumen of the inner conduit 6 and allows the insertion of a guide wire 14 into and through the lumen of the inner conduit 6 through a guide wire insertion port 12A of the connector member 12, as is known in the art of over the wire (OVT) catheters. The end 14D of the guide wire 14 may protrude beyond the distal end 6D of the inner conduit 6 and the guide wire 14 may be used to guide the insertion of the catheter 2 into a body passage (such as, but not limited to, a blood vessel) as is known in the art. A second hollow passage 18 is formed within a fluid port 12B of the connector member 12 which allows the introduction of an inflation fluid into the annular space 20 formed between the inner surface of the outer conduit 4 and the outer surface of the inner conduit 6.

Because of the fixed attachment of both the inner conduit 6 and the outer conduit 4 to the connector member 12, the inner conduit 6 is static and cannot be axially moved with respect to the outer conduit 4. However, due to the flexibility of the inner conduit 6 and the outer conduit 4, the shaft 1 of the catheter 2 may be flexed and bent sideways such that it is capable of being pushed along the guide wire 14 within tortuous or bending bodily passages (such as, but not limited to, blood vessels).

The inflatable balloon 10 is covered (or partially covered, depending on the particular embodiment of the catheter) with the sleeve 8. The balloon 10 is, preferably (but not obligatorily) a non-compliant or semi-compliant balloon which may be made from a suitable polymer based material, such as, but not limited to, Nylon® (preferably Nylon 12®), PET, polyamide (PA) such as PA12 (for example Grilamid® L25, L55 and the like), PA11, Polyether block amides (PEBA, such as for example, ® 7233, 7033, 6333), various types of Grilflex® (such as, for example, ELG 6260), and the like. Nevertheless, is accordance with certain embodiments of the catheters disclosed herein, the inflatable balloon used may be made of a highly compliant material such as, for example, rubber, Latex and the like (as will be further discussed in more detail hereinafter. However, any other suitable biocompatible material known in the art and suitable for fabrication of catheter balloons may be used in implementing the balloons of the present application.

The balloon 10 is typically capable of withstanding inflation pressures within the range of 4-25 atmospheres. However, the balloon 10 may be implemented to withstand inflation pressures lower than 4 atmospheres or higher than 25 atmospheres, depending, inter alia on the balloon dimensions, balloon wall thickness, the material from which the balloon is made and the specific application for which the catheter is designed.

Typical dimensions of the balloon 10 may be a balloon diameter in the range of 2-8 millimeters, a balloon length in the range of 8-300 millimeters and a balloon wall thickness in the range of 0.01-0.1 millimeters. However, these ranges are by no means obligatory or limiting and other higher or lower values of the balloon length, balloon diameter and balloon wall thickness outside the typical ranges indicated above may be also used, depending, inter alia, on the specific application for which the catheter is designed.

The sleeve 8 is, preferably (but not obligatorily) a non-compliant or semi-compliant sleeve which may be made from a suitable polymer based material, such as, but not limited to, Nylon® (preferably Nylon 12®), PET, polyamide (PA) such as PA12 (for example Grilamid® L25, L55 and the like), PA11, Polyether block amides (PEBA, such as for example, PEBAX® 7233, 7033, 6333), various types of Grilfiex® (such as, for example, ELG 6260), Polyester and the like including combinations of the above indicated materials. However, any other suitable biocompatible material known in the art and suitable for fabrication of sleeves may be used in implementing the balloons of the present application.

Typically, common engineering terms as known in the art of balloon catheters are defined as follows:

"Load"—is defined as the force or pressure acting on a component (such as a balloon, a conduit or a sleeve.

"Stretchable"—is used to define a component or structure or material that changes its shape or dimensions permanently after application of load (such as increase of diameter) by at least 10% of its original size and is deformed plastically under a working load.

"Non-stretchable"—is used to define a component or structure or material that does not permanently change its shape or dimensions after application of load by more than 10% of its original size or dimension.

"Compliant"—is used to define a component or structure or material that reversibly changes shape or dimension after application of load (such as an increase of diameter, and/or length, and the like) by at least 15% of its original size or dimension and is deformed super-elastically (in a rubber-like manner under a working load).

"Semi-Compliant"—is used to define a component or structure or material that reversibly changes its shape or dimension after application of load (such as increase of diameter) in the range of 2%-15% of its original size or dimension and is deformed elastically under a working load).

"Non-Compliant"—is used to defined a component or structure or material that reversibly changes its shape or dimension after application of load (such as increase of diameter or length, and the like) by 0%-2% of its original size or dimension and is either not deformed or is deformed elastically under a working load, within the above indicated range.

It is noted that in the above definitions, It is assumed that no breakage or tearing of the material, component or structure occurs during the application of the load.

TABLE 1 below lists some of the materials suitable for use in making the balloons and/or sleeves of the catheters of the present application and classifies such materials with regard to their mechanical properties as related to the above term definitions.

TABLE 1

| Material FAMILY | Material grade | S | NS | C | SC | NC |
|---|---|---|---|---|---|---|
| Polyamide (PA) (Any Grade) non-Oriented | | Yes | No | no | No | No |
| PA 12 oriented | Grilamid ® L25 | no | Yes | No | Yes | No |
| | Grilamid ® L55 | No | Yes | No | Yes | No |
| PA 11 oriented | Rilsan B Esno | No | Yes | No | Yes | No |
| Polyether block amides (PEBA) | PEBAX 7233 non oriented | Yes | No | No | No | No |
| | PEBAX 7233 oriented | No | Yes | No | Yes | No |
| | PEBAX 7033 non oriented | Yes | No | No | No | No |
| | PEBAX 7033 oriented | No | Yes | No | Yes | No |
| | PEBAX 6333 | SW About 12-16% | No | No | Yes | No |
| | PEBAX 5533 ** | SW about 20-30% | No | SW About 20-30% | No | No |
| | Grilflex ® ELG 6260 | SW about 12-16% | No | No | Yes | No |
| PET PET/Polystyrene) oriented | Mylar ® | No | No | No | No | Yes |
| Polyethylene (PE) non-oriented | HD/LD/LLD | Yes | No | No | Yes * | No |

* there will be noticeable elastic shrinkage after plastic deformation.
** PEBAX 5533 is a material with mechanical properties similar (but not identical) to a hard but non-vulcanized rubber.
In TABLE 1 above, the following shorthand denotations are used to represent the following mechanical properties: S—represents "Stretchable"; NS—represents "Non-Stretchable"; C—represents "Compliant"; SC—represents "Semi-Compliant"; NC—represents "Non-Compliant"; SW—represents "Somewhat".

The sleeve 8 is capable of withstanding the forces exerted by the balloon when the balloon 10 is inflated to its nominal inflated diameter. The sleeve 8 may also increase the internal pressure the balloon 10 can withstand by supporting (or reinforcing) the balloon 10 when the balloon 10 is inflated, by suitably selecting, among others, the wall thickness of the sleeve, and the mechanical properties of the material(s) from which the sleeve is made.

Typical dimensions of the sleeve 8 may be a sleeve diameter in the range of 2-15 millimeters, a sleeve length in the range of 8-300 millimeters and a sleeve wall thickness in the range of 0.01-0.1 millimeters. However, these ranges are by no means obligatory or limiting and other higher or lower values of the sleeve length, sleeve diameter and sleeve wall thickness outside the typical ranges indicated above may be also used, depending, inter alia, on the specific application for which the catheter is designed. For example, if the catheter is used for treating peripheral veins, the diameter of the sleeve in the fully opened state and the diameter of the balloon at the nominal inflation pressure may be even larger than 15 millimeters (if treating large peripheral veins or the vena cava)

Turning to FIGS. 5-7, the balloon 10 has a proximal end 10A and a distal end 10B. The proximal end 10A of the balloon 10 is sealingly attached to the outer surface 4A of the distal end 4D of the outer conduit 4 and the distal end 10B of the balloon 10 is sealingly attached to the outer surface 6A of the inner conduit 6. The sleeve 8 has a proximal end 8A and a distal end 8B. The proximal end 8A of the sleeve 8 is sealingly attached to the outer surface 4A of the distal end 4D of the outer conduit 4. The distal end 8B of the sleeve 8 is not connected to the surface 6A of the inner shaft and is free to move radially away from the inner conduit 6 upon inflation of the balloon 10. The attachment of the balloon's distal end 10B to the inner conduit 6 and the attachment of both the balloon's proximal end 10A and the sleeve's proximal end 8A to the outer conduit 4 may be done by bonding, thermal bonding, ultrasonic bonding, gluing using any suitable adhesive or glue or by any other attaching methods known in the art.

The configuration of the balloon 10 with the sleeve 8 of the catheter 2 is best seen in FIG. 5. The configuration of the balloon 10 and the sleeve 17 of the catheter 2 are best seen in FIGS. 3 and 4 In this initial state (folded state or wrapped state) the balloon 10 is folded (as shown in FIG. 2) such that the folded balloon 10 and the non-folded sleeve 8 surrounding the balloon 10 have a low crossing profile which may assist the crossing of an atheroma or other lesion or constriction or obstruction of the body passage or blood vessel to be treated. Similarly, in the catheter 100 (FIG. 3), the balloon 10 and the sleeve 17 are both folded and wrapped around the surface 6A of the inner conduit 6 of the shaft 101 of catheter 100, resulting in a low crossing profile which may assist the crossing of an atheroma or other lesion or constriction or obstruction of the body passage or blood vessel to be treated.

The lower crossing profile achieved by the two different folding configurations illustrated in FIGS. 2 and 4 improves the passability and pushability of the distal end of the catheters 2 and 100, respectively, into and/or through a constricted region or atheroma or plaque in an atheromatous blood vessel.

As illustrated in FIG. 5, in the folded (or wrapped) configuration (prior to inflation of the balloon), the balloon 10 is disposed adjacent to the outer surface of the inner conduit 6 and the proximal part 10A of the balloon 10 is sealingly attached to the distal end 4D of the outer conduit 4. The sleeve 8 is disposed over part of or most of the balloon 10 covering most of the length from proximal end 10A of the balloon 10 up to the distal end 10B of the balloon 10.

Figure 14:
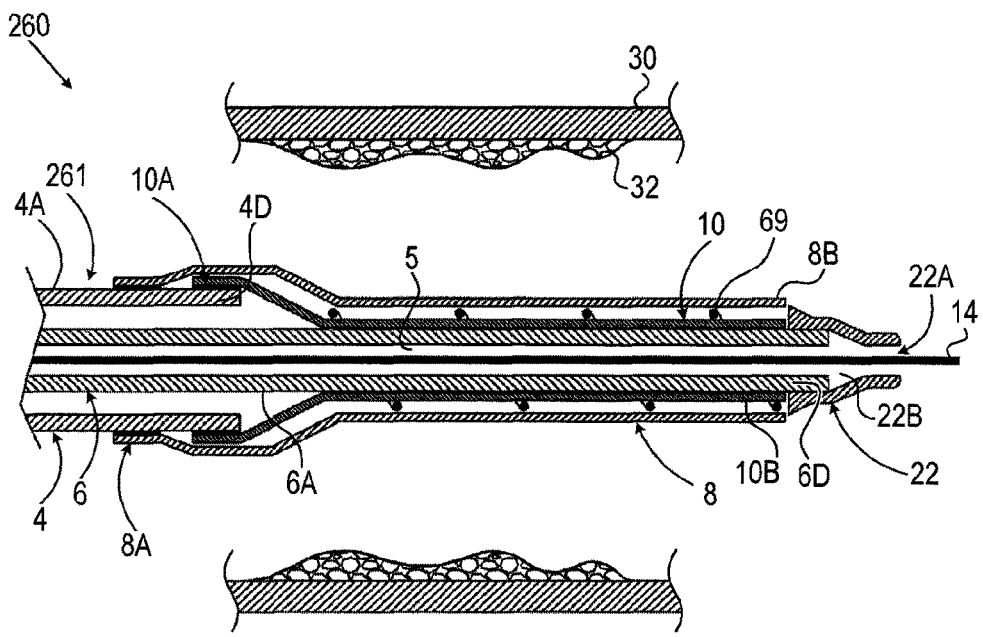
FIG. 14-15 are schematic cross-sectional diagrams of part of a catheter with a balloon and a sleeve having an expandable sleeve supporting member disposed over the balloon and under the sleeve, illustrated at two different steps of operating the catheter, in accordance with another embodiment of the catheters of the present application.
Figure 22:
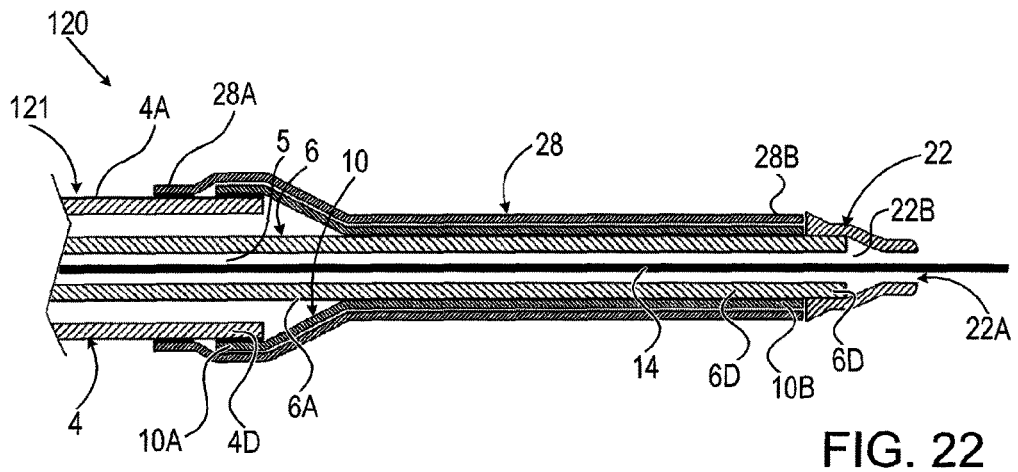
FIG. 22 is a cross-sectional diagram illustrating, part of a catheter including a double conduit shaft, a balloon and a sleeve having a distal end that extends distally along the catheter shaft to the same longitudinal position of the distal end of the balloon when the balloon is in the deflated state, in accordance with another embodiment of the catheter of the present application.

Alternatively, in accordance with another embodiment of the catheter, the entire length of the balloon 10 may be covered by and disposed within the sleeve 8 (see FIGS. 14 and 22). In accordance with yet another embodiment of the catheter, the distal end of the sleeve may extend distally beyond the distal end of the balloon (see, for example FIGS. 23-24).

The proximal end 8A of the sleeve 8 is sealingly attached to the distal end 4D of the outer conduit 4 (as illustrated in FIGS. 5-7). Alternatively, in accordance with another embodiment of the catheter, the proximal end 10A of the balloon 10 is sealingly attached to the distal end 4D of the outer conduit 4 and the proximal end 8A of the sleeve 8 is sealingly attached to the proximal end 10A of the balloon 10 (as best seen in the catheter 500 of FIG. 36).

The distal end 8B of the sleeve 8 is located at some distance proximal to the distal end 10B of the balloon 10 (along the outer conduit 4). The sleeve 8 can be placed over the balloon 10 in two different configurations at the initial state (prior to inflation of the balloon), described at FIG. 2-3. FIG. 2 is a cross-section of the catheter of FIG. 1 taken along the lines II-II. The balloon 10 is folded (wrapped) over the inner conduit 6 and the sleeve 8 is a tubular sleeve having an initial diameter that is slightly larger than the maximal radial dimension of the folded balloon 10 such that the sleeve 8 fits over the folded balloon 10 which is wrapped around the outer surface of the inner conduit 6. During use of the catheter 2, in an inflation step, (illustrated in FIG. 6), the balloon 10 is inflated (by introducing an inflation fluid through the passage 18 of the fluid port 12B of FIG. 1) and the sleeve 8 is expanded by the inflated balloon 10.

Typically, in the catheter 2, before inflation of the balloon 10, the initial (non-expanded) diameter of the sleeve 8 is smaller than the nominal diameter of the fully inflated balloon 10, the balloon 10 while being inflated exerts a force on the sleeve 8 and pushes on the sleeve 8, causing the sleeve 8 to stretch and expand and increases the diameter of the sleeve 8. In the catheter 2, the sleeve 8 may be made from a stretchable compliant material(s) to enable the inflation of the balloon 10 to stretch and expand the sleeve 8 from the initial non-expanded state (as seen in FIGS. 1-2) to an expanded state in which the sleeve 8 has a diameter which is larger than the diameter of the sleeve 8 in the non expanded (or pre-expanded). The expanded state of the sleeve 8 is best seen in FIG. 6.

Returning to FIG. 3, an alternative configuration of the sleeve of the catheter is illustrated in the cross-sectional diagrams of FIGS. 3 and 4. In the catheter 100, the balloon 10 is folded over the inner conduit 6 and the sleeve 17 is folded over the balloon 10. In a balloon inflating step, the balloon 10 is inflated to the expanded state and pushes the sleeve 17 radially outside which causes the folded sleeve 17 to unfold and expand to an opened expanded state. It is noted that in the embodiment including a folded openable sleeve 8 which is folded over the folded balloon 10 there are two different alternative configurations. In the first implementation, the internal diameter of the fully unfolded (fully opened) sleeve 17 is equal to or slightly greater than the nominal (inflated) outer diameter of the balloon 10. In this implementation, when the balloon 10 is inflated using the nominal inflation pressure, the balloon 10 opens the sleeve 17 without substantially stretching the sleeve 17. In this embodiment, the sleeve 17 may be made from non-compliant, non-stretchable material(s), such that the internal diameter of the fully unfolded sleeve 17 is sufficiently large to accommodate the fully nominally inflated outer diameter of the balloon 10.

In the second implementation, the diameter of the fully unfolded sleeve 17 is substantially smaller than the diameter of the balloon 10 when the balloon 10 is inflated with the nominal inflation pressure. In this implementation, when the balloon 10 is inflated using the nominal inflation pressure, the expanding balloon 10 first unfolds and expands and pushes open the folded sleeve 17 and then stretches and expands the sleeve 17 to reach an inner sleeve diameter which is greater than the unfolded but non-stretched diameter of the sleeve 17. In this second implementation, the sleeve 17 first unfolds without stretching until the outer diameter of the inflated balloon 10 becomes equal to the inner diameter of the unfolded but not yet stretched sleeve 17. Any further increase of the outer diameter of the balloon 10 due to further inflation of the balloon 10 will begin to stretch the sleeve further until the balloon reaches its nominal inflation pressure and stops expanding. In the second implementation the sleeve 17 is made from a material which may be stretched and expanded to a diameter which is significantly larger than the initial diameter of the sleeve 17 in its unfolded (but non-stretched) state. In such an implementation the sleeve may be made from suitably semi-compliant and/or partially-stretchable material(s) such as, for example, any of the material with the required properties as indicated in TABLE 1 hereinabove.

In some of the embodiments of the catheters, the sleeves 8 or 17, and or any of the other sleeves disclosed hereinafter may be made from materials which while being stretchable to a certain extent, may reach a state (a certain limiting or threshold diameter) where they may not be stretchable any more or may exhibit a strong resistance to further stretching (by requiring a much stronger force to stretch them any further than the threshold diameter). This property may be particularly useful in catheters in which the balloon 10 is made from a highly compliant material such as Latex® and the like because the stretched sleeve may control the shape and/or the diameter of the inflated balloon, which may otherwise (without the presence of the sleeve) tend to undesirably inflate to a more rounded shape or even explode due to accidental application of pressure higher than the maximal permitted inflation pressure. In such a case, the sleeve may also operate as an additional safety mechanism operating to prevent or reduce over-inflation or even bursting of the balloon Optionally, (but not obligatorily), the catheter 2 includes a soft tip 22, which is attached to the distal end 6D of the inner conduit 6. The soft tip may be shaped as a hollow conical or frusto-conical tip but other shapes such as, but not limited to a hollow rounded open cap (not shown) may also be used if desired. The soft tip 22 may be made from a soft pliable material, such as but not limited to PEBAX 5533, PEBAX 6333, or similarly soft TPU, such as polyurethane. Preferably, but not obligatorily, the material of the soft tip 22 (or the soft tip 27 disclosed hereinafter) may include a radio-opaque filler, such as but not limited to, barium sulphate (BaSO$_4$) or the like. Such radio-opaque filler including soft tip may be used as a radio-opaque marker indicating the approximate position of the distal balloon end when viewed using angiographic methods to position the catheter.

The soft tip 22 may be glued or bonded or otherwise fixedly or detachably attached to the distal end 6D of the inner conduit 6 (such as, but not limited to, by gluing, bonding, thermal bonding, or by mounting without bonding and the like), such that the guide wire 14 may pass through the hollow passage 22B formed within the soft tip 22 and exit from an orifice 22A at the distal end of the soft tip 22.

The soft tip 22 facilitates passage of the catheter through bending or tortuous bodily passages or blood vessels, without damaging or injuring the walls of the bodily passage or of the blood vessel. However, the soft tip 22 is optional and the catheters disclosed in the present application may be constructed and used without such a soft tip.

In operation, the operator of the catheters 2 and 100 may insert the guide wire 14, through a suitable cannula or other suitable insertion port in the body into the vasculature as is known in the art. The operator may advance the distal end of the guide wire 14 within the blood vessel until the region to be treated is reached. The catheter 2 or 100 may then be pushed and passed into the blood vessel over the guide wire 14. At this stage, the balloon 10 is in an initial state (prior to inflation of the balloon) configuration as shown in FIGS. 1-4, which has a small crossing profile. When the distal end of the catheter 2 or 100 reaches the region to be treated, the balloon 10 is properly positioned within the atheroma or constriction to be treated, as is illustrated in detail in FIGS. 1 and 5.

The operator may then inflate the balloon 10 by introducing a suitable inflation fluid (not shown) under pressure into the balloon 10 by using a suitable indeflator (not shown) or an inflation fluid filled syringe (not shown), which may be coupled or connected to the fluid port 12B of the connecting member 12. The inflation fluid pressure may vary depending on the dimensions, wall thickness and material of the balloon 10 and the sleeve 8. Typically, inflation pressure may be in the range of 4-25 atmospheres, but the balloon inflation pressure may be different (lower or higher) than the above indicated value range, depending, inter alia, on the application and on the balloon type and dimensions. The injection of the inflation fluid into the passage 18 of the fluid port 12B inflates and expands the balloon 10 into an expanded state, which results in expansion of the sleeve 8, as is shown in detail in FIG. 6. The portion 8C of the outer surface of the sleeve 8 is pushed against the vessel wall 30 and may compress and/or open the atheroma (or plaque, or other obstruction) 32 to increase the open cross-sectional area of the inner lumen of the blood vessel. Optionally (but not obligatorily), at this stage, a stent (not shown in FIGS. 5-7) disposed over the sleeve 8 may be opened by the expansion of the balloon 10 and the sleeve 8 and deployed onto the vessel wall 30 as is known in the art, any type of suitable balloon deployable stent may be used in such an optional stent deployment step, as is well known in the art of balloon deployable stents. A specific embodiment illustrating the steps of deploying a stent in a blood vessel is disclosed in detail and illustrated in FIGS. 28-30 hereinafter.

It is noted that in the state of the catheter illustrated in FIG. 6, the distal end 10B of the balloon 10 extends distally beyond the distal end 8B of the sleeve 8 when the balloon 10 is in the inflated state. However, this is not obligatory to the operation of the catheter and other embodiments of the catheter may be constructed in which the relationship between the distal end of the balloon and the distal end of the sleeve, when the balloon is in the inflated may be different than the relationship illustrated in FIG. 6 (see for example the arrangement of the sleeve and the balloon of catheters 140 and 150, of FIGS. 24 and 25, respectively).

Figure 7A:
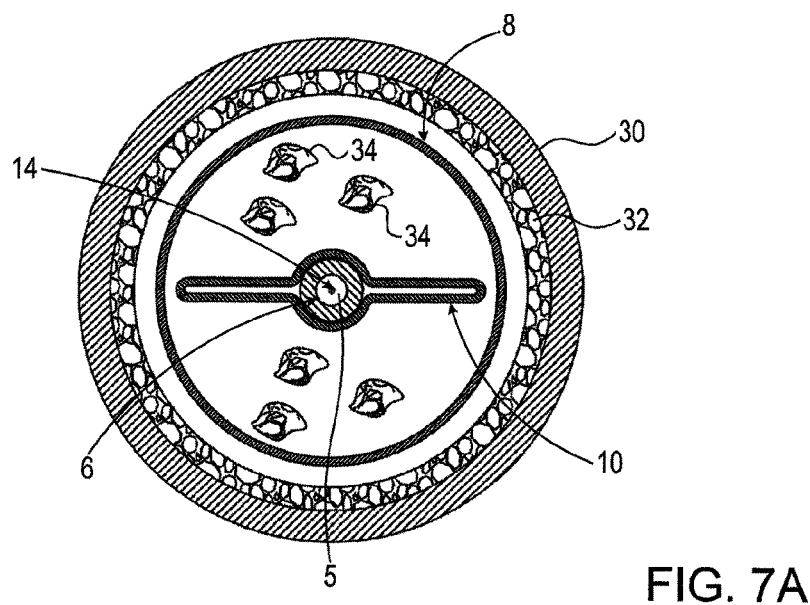
FIG. 7A is a schematic cross-section of the catheter of FIG. 7 taken along the lines VIIA-VIIA.

After treatment of the lesion or constriction in the vessel, the balloon 10 is deflated by reducing the pressure in the catheter 2 or 100 through the passage 18 of the fluid port 12B, such as, for example, by suitably opening a stopcock or valve (not shown) connected to the fluid port 12B or by suitably depressurizing the indeflator or syringe connected to the Fluid port 12B and being used for inflation, as is known in the art. Deflating the balloon 10 results in the formation of an annular open cavity 40 between the balloon 10 and the sleeve 8, (as best seen in FIGS. 7 and 7A). The cavity 40 is defined between the inner surface of the wall of the sleeve 8 and the outer surface of the balloon 10. As seen best in FIG. 7, the distal part of the cavity 40 is open to the inner lumen of the blood vessel.

Reference is now made to FIG. 7A, which is a schematic cross-section of the catheter of FIG. 7 and the blood vessel 30 taken along the lines VIIA-VIIA, illustrating the configuration of the balloon 10 and the sleeve 8 after the step of deflating the balloon 10. The formation of the open cavity 40 following the deflation of the balloon 10 generates suction which results in drawing of blood and debris 34 such as plaque debris from the lumen of the blood vessel into the cavity 40. This is advantageous as it reduces the amount of such debris 34 that may enter the blood stream. The suction developed during the formation of the cavity 40 results in the debris 34 being trapped within the cavity 40. The trapped debris 34 may subsequently be removed from the body together with the catheter 2 or 100. Thus, the risk of patient embolism is advantageously significantly reduced. It is noted that in the schematic diagram of FIG. 7A, the shape of the deflated and flattened balloon 10 is illustrated only schematically (for the sake of clarity of illustration). It will be appreciated by those skilled in the art that the actual way of the deflated balloon may have a different deflated shape than the schematic shape shown in FIG. 7A and may actually exhibit a non-symmetrical and/or non-uniform flattening profile and may as well include kinking and crumpling of the balloon wall as is well known in the art.

After the balloon 10 is deflated, the catheter 2 or 100 may be withdrawn from the vasculature by pulling it proximally until it exits the vasculature through the insertion port together with any debris 34 trapped within the cavity 40.

Figure 8:
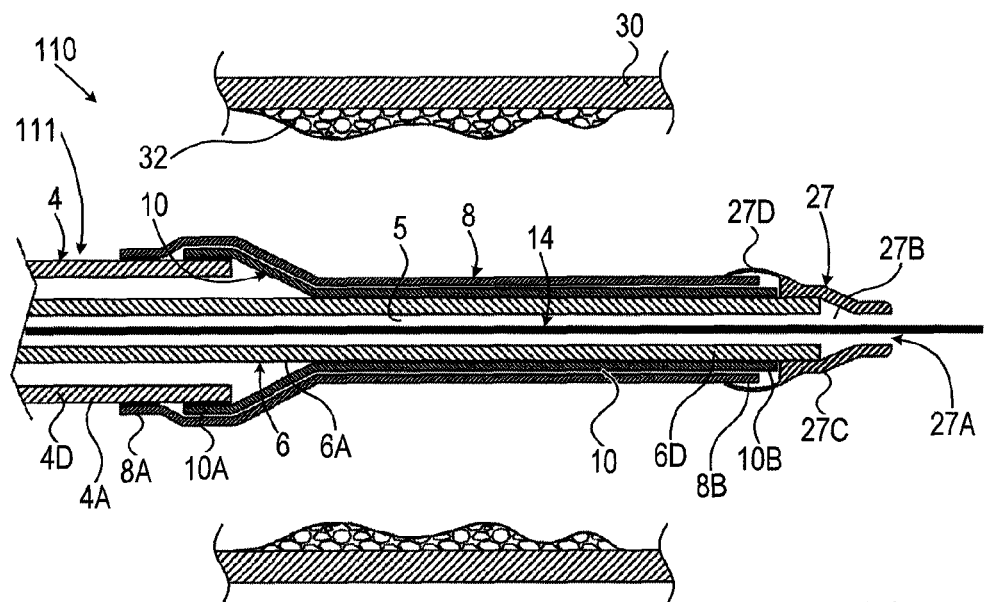
FIGS. 8 and 9 are schematic cross-sectional diagrams of part of a catheter with a balloon and a sleeve, the catheter having a soft tip with a cup-like portion for surrounding a distal part of the balloon and sleeve illustrated at two different steps of operating the catheter.
Figure 9:
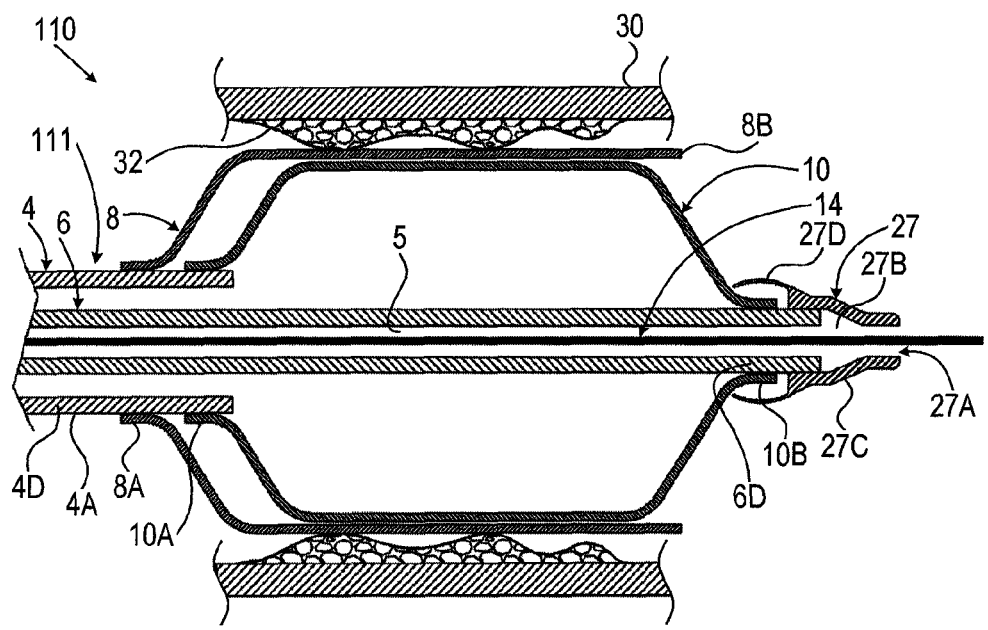

Reference is now made to FIGS. 8 and 9. FIG. 8 is a schematic cross-sectional diagram illustrating part of an embodiment of a catheter having a soft tip with a proximal sleeve retaining member useful in securing the distal end of the sleeve in the initial state (prior to inflation of the balloon) configuration. FIG. 9 is a schematic cross-sectional diagram illustrating part of the catheter of FIG. 8 after the balloon has been inflated.

In the embodiment of the catheter illustrated in FIGS. 8-9, the catheter 110 may be similar in structure to the catheter 2 of FIG. 1, except that the catheter 110 includes a soft tip 27 instead of the soft tip 22 of the catheter 2. The soft tip 27 is attached to the distal end of the inner conduit 6D of the catheter 110. The soft tip 27 has a hollow passage 27B passing therethrough and opening at an orifice 27A to allow passage of the guide wire 14 (or a medical or diagnostic device) therethrough. As described in detail for the soft tip 22 of catheter 100 hereinabove, the soft tip 27 has a conical (or tapering or rounded) distal part 27C and has a retaining member 27D. Preferably (but not obligatorily), the retaining member 27D is shaped as a cup-like portion of the soft tip 27 which has thin walls which may be thinner than the wall of the distal part 27C. Turning to FIG. 8, when the balloon 10 and the sleeve 8 are in the initial non-inflated state (prior to using the catheter), the retaining member 27D is disposed over the distal part 8B of the sleeve 8 such that the thin walls of the retaining member 27D surround the distal part 8B of the sleeve 8, and secures the distal sleeve part 8B such that it cannot open in a radial direction and is securely held by the retaining member 27D adjacent to the outer surface of the distal part 10B of the balloon 10. The retaining member may hold either the sleeve 8 and/or the balloon 10 and may also be useful to prevent accidental unfurling away of the folded balloon 10 from the inner shaft 6 (see FIGS. 2 and 4) and/or the radial unfurling of the folded sleeve 8 away from the balloon 10 around which the sleeve is folded (as shown in FIG. 4). It is noted that the lengthy and the diameter and shape of the retaining member 27 may be varied, depending, inter alia, on the length of the sleeve, the length of the folded balloon, and the diameter of the folded balloon and/or folded sleeve in the folded configuration.

This arrangement also prevents accidental movements or dislodging of the sleeve 8 and reduces the probability that the sleeve part 8B will become prematurely snagged or expanded laterally before or during the inserting of the catheter into the body as well as when the catheter is being moved within the vasculature or bodily passage. The use of the soft tip 27 makes it easier to insert the balloon 10 and the sleeve 8 into the vasculature and to pass the balloon 10 and the sleeve 8 within the vasculature in the proper tightly wrapped (folded) shape having a low crossing profile until the catheter's distal end reaches the site to be treated and the balloon 10 is properly positioned in the region to be treated.

Turning to FIG. 9, when the catheter 110 has been properly navigated into the region to be treated (such as, for example, an atheromatous arterial region or arterial constriction) and the balloon 10 is properly positioned, the balloon 10 is inflated as disclosed hereinabove with respect to the catheter 2 illustrated in FIG. 6. When the balloon 10 is inflated, the distal part 8B of the sleeve 8 pushes aside (in the lateral direction) the thin walls of the proximal portion of the sleeve retaining member 27D of the soft tip 27, the distal sleeve portion 8B is released from the sleeve retaining member 27D and the balloon 10 expands to its inflated state, as best seen in FIG. 9.

It is noted that the two different types of the soft tips 22 and 27 may be optionally and interchangeably used in any of the catheters described in the present application to achieve the advantages disclosed hereinabove. However, any of the catheters of the present application may also be constructed and operated without a soft tip.

It is noted that the catheters disclosed in the present application (including but not limited to the catheters 2, 52, 100, 110, 120, 130, 140, 150, 160, 170 202, 230, 250, 260, 270, 280, 352, 400 and 500) have the advantage of having no axially moving parts in the catheter shaft and are therefore easy to construct and inexpensive and simple in use. Nevertheless, additional catheter configurations may be implemented which may add additional functionality to the inner conduit of the catheter.

Reference is now made to FIG. 10 which is a schematic cross-sectional diagram illustrating a rapid exchange balloon catheter having a fixed non-movable angled inner conduit an inflatable balloon and a sleeve, shown during a step in which the balloon is in a deflated state after being in an inflated state, in accordance with an embodiment of the rapid exchange catheters of the present application.

The rapid exchange catheter 202 includes a shaft 201 including an outer conduit 204 and an angled inner conduit 206 disposed within the outer conduit 204. The catheter 202 also includes a balloon 10 attached to the distal portion of the shaft 201, a sleeve 8 attached to the distal portion of the shaft 201 and a hollow connector member 212 attached to the proximal portion of the shaft 201. The proximal part of the connector 212 includes a fluid port 212A having a hollow passage 216 passing therethrough. The inner conduit 206 has an outer diameter which is smaller than the diameter of the lumen 220 of the outer conduit 204. The proximal end 204P of the outer conduit 204 is firmly and sealingly attached to a recess 212R formed in the distal portion of the connector member 212, by suitably sealingly attaching by bonding or gluing or welding or ultrasonically welding, or the like, of the proximal part 204P within the recess 212R.

The balloon 10 has a proximal end 10A sealingly attached to the outer surface of the distal end 204D of the outer conduit 204 by bonding or gluing or the like, using any of the attaching or bonding or gluing or welding methods described in detail hereinabove. The balloon 10 has a distal end 10B sealingly attached to the outer surface of the distal end 206D of the inner conduit 206 by bonding or gluing or the like, using any of the attaching or bonding or gluing or welding methods described in detail hereinabove. The balloon 10 is thus fluidically in communication with the fluid port 212A through the lumen 220 of the outer conduit 204.

Inflation fluid (not shown) may be introduced into the lumen 220 and therefrom into the lumen of the balloon 10 through the passage 216 formed in a fluid port 212A, as disclosed in detail hereinabove by using an indeflator (not Shown) or a syringe (not shown) filled with inflation fluid connected to the fluid port 212A.

The inner conduit 206 has a straight portion 206B and an angled portion 206A which is inclined at an angle to the straight portion 206B. The angled portion 206A pierces the wall of the outer conduit 204 and is sealingly attached to the wall of the outer conduit 204 such as to prevent leakage of any inflation fluid introduced into the lumen 220 through the opening 216 of the fluid port 212A. A hollow soft tip 22 may (optionally, but not obligatorily) be attached to the distal end 206D of the inner conduit 206 (as disclosed in detail with respect to the soft tip 22 of FIG. 1).

An opening 15 is disposed in the wall of the outer conduit 204 at the proximal end of the angled portion 206A of the inner conduit 206. The opening 15 allows the insertion of a guide wire 14 into the lumen 205 of the inner conduit 206. The guide wire 14 may be pushed through the lumen 205 until it exits from an opening 22A at the distal end of the soft tip 22. The balloon 10 and the sleeve 8 may be arranged in the wrapped (folded) configurations similar to the initial configuration of the balloon 10 and the sleeve 8 of catheter 2 of FIGS. 1-2. Alternatively, the arrangement of the balloon 10 and the sleeve 8 may be identical to the arrangement of the balloon 10 and the sleeve 17 of the catheter 100 of FIGS. 3-4.

The various steps of operating the rapid exchange catheter 202 are similar to the steps of operating the over the wire (OVT) catheters 2, 100 and 110, as described hereinabove and illustrated in FIGS. 1-9, with the exception that while in use and operation of the catheters 2, 100 and 110 the guide wire 14 is inserted into the lumen of the inner conduit 6 through the guide wire port 12A disposed at the proximal end of the catheters, when using the rapid exchange catheter 202, the guide wire 14 is inserted through the opening 15 of the shaft 201 into the lumen 205 of the inner conduit 206. However, other steps of the operation of the catheter 202, including inserting the catheter into the body or bodily vasculature while the balloon 10 is in the folded configuration (as illustrated in FIGS. 2 and 4), moving the catheter within the vasculature to reach a region to be treated, inflating the balloon 10 to expand the balloon 10 and the sleeve 8 for treating a constriction or atheromatous plaque 32 within the vessel (as illustrated in FIGS. 6 and 9) with or without deployment of an (optional) stent disposed on the sleeve 8, deflating the inflated balloon 10 to form a cavity 40 defined between the deflated balloon 10 and the sleeve 8 for collecting and trapping debris 34 in the cavity 40 (as illustrated in FIG. 6) and withdrawing of the catheter and the debris 34 trapped therein outside of the body, are similar to the corresponding operating steps as described in detail hereinabove for the catheters 2, 100 and 110.

Figure 11:
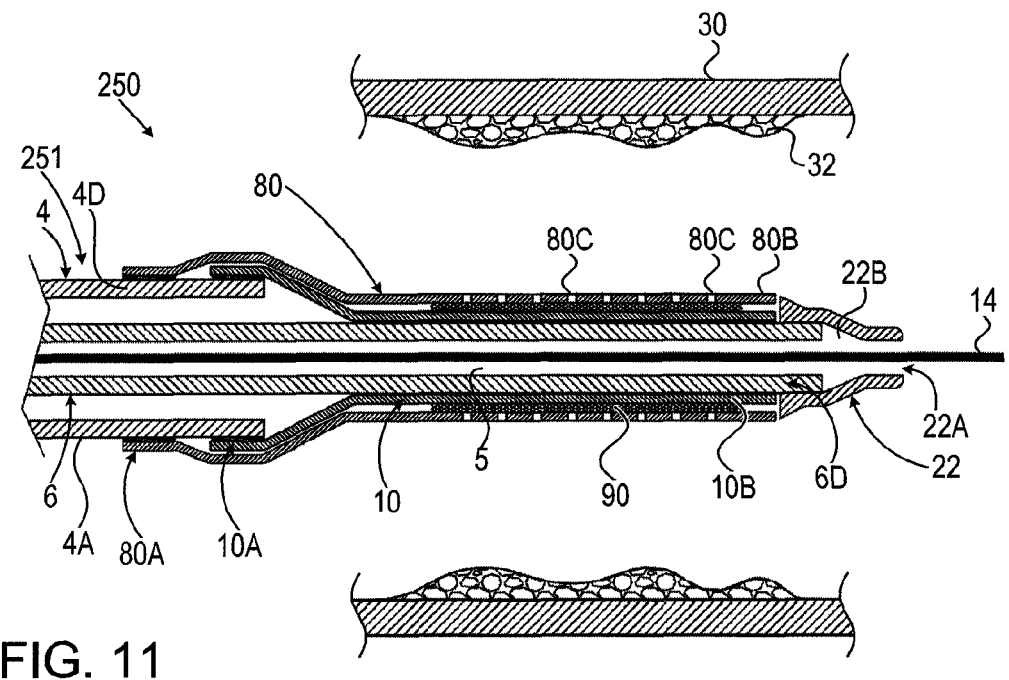
FIGS. 11 and 12 are schematic cross-sectional diagrams of part of an over the wire catheter having a balloon with drug/medicine disposed between the balloon and a sleeve, illustrated at two different steps of operating the catheter.
Figure 12:
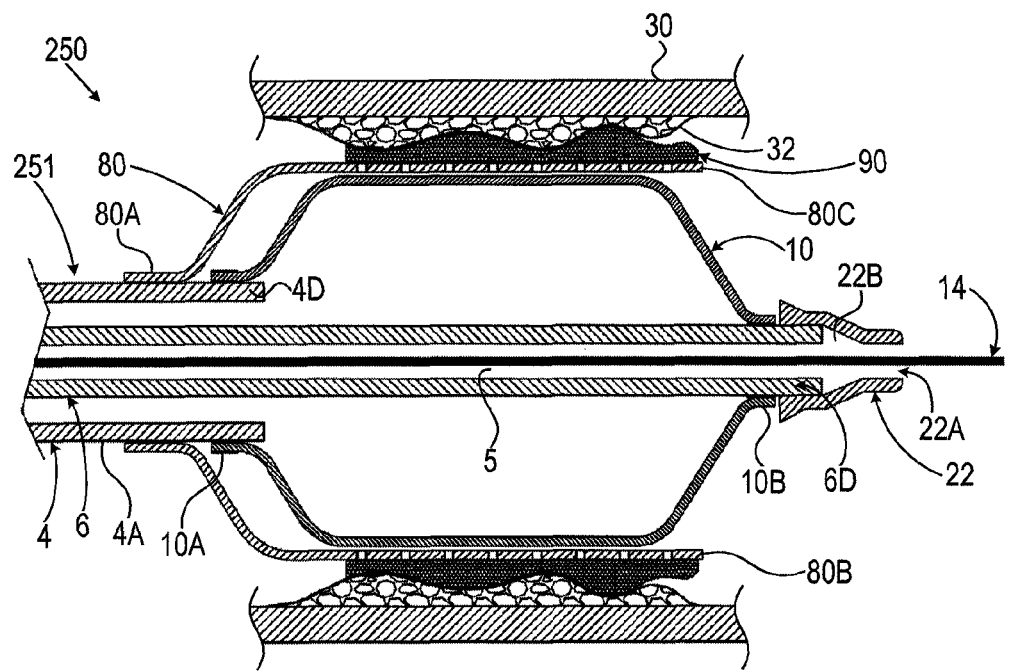

Reference is now made to FIGS. 11 and 12 which are schematic cross-sectional diagrams illustrating part of an over the wire catheter having a balloon and a sleeve with a substance (such as, for example, a drug or a medicinal or therapeutic composition) disposed between the balloon and the sleeve, shown during two different steps of operating the catheter, in accordance with yet another embodiment of the catheters of the present application.

Turning to FIG. 11, the catheter 250 includes a shaft 251 having an inner conduit 6 and an outer conduit 4. The catheter also includes a balloon 10 and a sleeve 80 attached to the shaft. The sleeve 80 has multiple perforations 80C therein and a drug or a medicinal composition or therapeutic or diagnostic substance 90 disposed between the balloon 10 and the sleeve 80. The proximal end 10A of the balloon 10 is sealingly attached to the distal end 4D of the outer conduit 4 as disclosed in detail hereinabove with respect to FIG. 1. The proximal end 80A of the perforated sleeve 80 is sealingly attached to the proximal end 10A of the balloon 10. The distal end 80B of the perforated sleeve 80 is an open end which overlies the distal end 10B of the balloon 10. The perforated sleeve 80 may be made of or may include a porous material or may be a perforated sleeve that has perforations (or openings) 80C therein. The perforated sleeve 80 may comprise a material having a sponge-like structure with open cavities allowing extrusion of the substance to the outer surface of the sleeve when the balloon is inflated.

A typical (but not obligatory) range for such perforations (or openings) 80C includes perforations or openings with diameters between 0.001-0.5 millimeter (however, other smaller or larger perforation diameters may also be used, depending, inter alia on the type and chemical and physical characteristics (including but not limited to viscosity) of drug or medicinal composition being deployed by the catheter. The perforations 80 may be perforations having a circular cross section and perforations having non-circular cross sections of any desired cross-sectional shape, In sleeves having perforations with a non circular cross-section, the average cross sectional area of the perforations may be in the range of the cross sectional area of perforations having a circular cross section having diameters in the range of 0.001-0.5 mm, but higher or lower values of the cross-sectional area may be used depending, among others, on the viscosity and extrudability and/or other flow characteristics of the particular substance 90 being used.

Turning to FIG. 12, when the balloon 10 and the sleeve 80 are in the initial state configuration (prior to using the catheter or inflating of the balloon 10), the drug or medicinal composition or therapeutic substance 90 is securely held between the balloon 10 and the sleeve 80, as long as the balloon is in pre-inflation configuration, due to relatively small diameter of the perforations 80C in the sleeve 80 and the tightly folded disposition of the balloon 10 and sleeve 80. This arrangement prevents accidental movements of the drug or medicinal composition or therapeutic substance 90 and reduces the probability of release of the drug or medicinal composition or therapeutic substance 90 before or during the inserting of the catheter 250 into the body as well as when the catheter 250 is being moved within the vasculature or another bodily passage. This allows the inserting of the balloon 10, the sleeve 80 and the drug or medicinal composition or the therapeutic substance 90 between them into the vasculature and the passing of the catheter 250 within the vasculature in the proper tightly folded (wrapped) state which has a low crossing profile until the catheter's distal end reaches the site to be treated and the balloon 10 is properly positioned in the region to be treated.

Returning to FIG. 11, when the catheter 250 has been properly navigated into the region to be treated (such as, for example, an atheromatous arterial region or arterial constriction) and the balloon 10 is properly positioned, the balloon 10 is inflated as disclosed hereinabove with respect to the catheter 100 of in FIG. 6. When the balloon 10 is inflated, the substance 90 is subjected to the force exerted by the inflating of the balloon 10 on the substance 90 disposed between the balloon 10 and the sleeve 80 and is extruded through the perforations 80C of the sleeve 80 and applied to the vessel 30 and/or to any lesion and/or plaque and/or atheroma adjacent to the outer surface of the perforated sleeve 80. As the balloon 10 expands to its nominal inflated diameter, the sleeve 80 is expanded by the inflated balloon 10 and may come into contact or at least in close proximity to the pathological lesion such as for example the plaque 32 of the vessel wall 30 and the substance 90 may be either extruded onto the region to be treated or released into or may diffuse to come in contact with the region to be treated of the vessel, as seen in FIG. 12.

It is noted that the use of a perforated sleeve 80 in combination with a drug or medicinal composition or therapeutic substance 90 may be used in any of the different types of catheters disclosed in the present application, including any of the over the wire catheters, rapid exchange catheters and multi-lumen and/or multi-conduit catheters of the present application by substituting the non-perforated sleeve of a catheter with a suitable perforated sleeve and by adding any desired substance and/or drug and/or therapeutic composition and/or diagnostic composition or any other suitable substance or composition between the balloon 10 of the catheter and the perforated sleeve 80 of the catheter being used.

Figure 13:
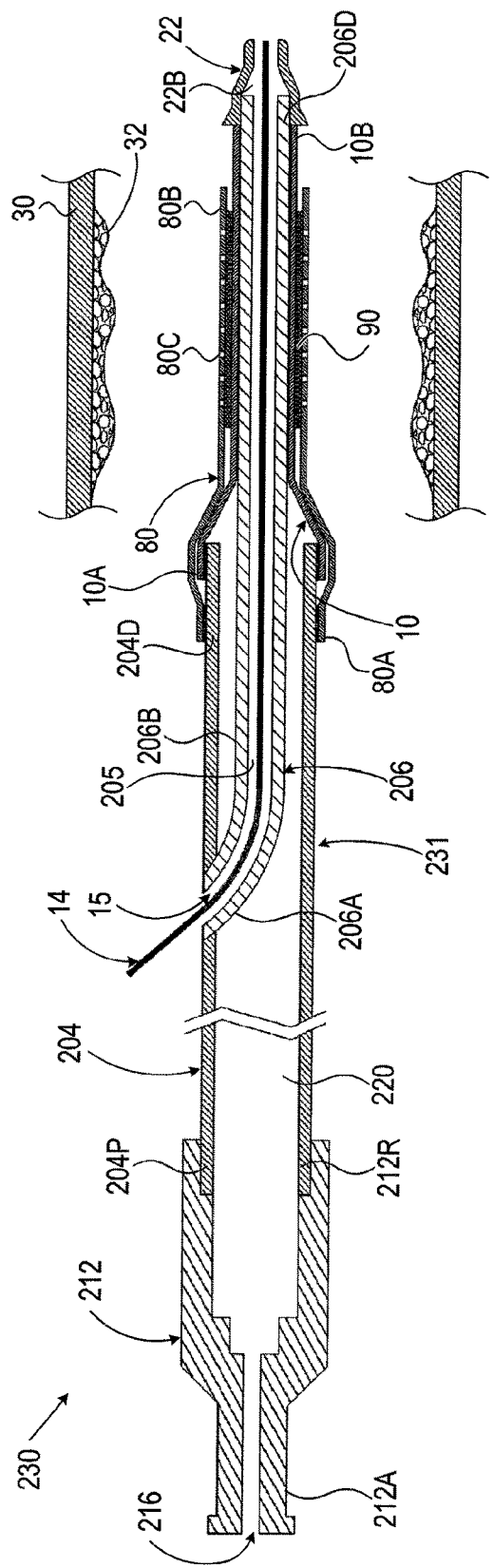
FIG. 13 is a schematic cross-sectional diagram illustrating a rapid exchange catheter having a balloon with drug/medicine/substance/composition disposed between a balloon and a perforated sleeve.

For Example, FIG. 13 is a schematic cross-sectional diagram illustrating a rapid exchange catheter having a balloon with drug/medicine/substance disposed between a balloon and a perforated sleeve.

Figure 36:
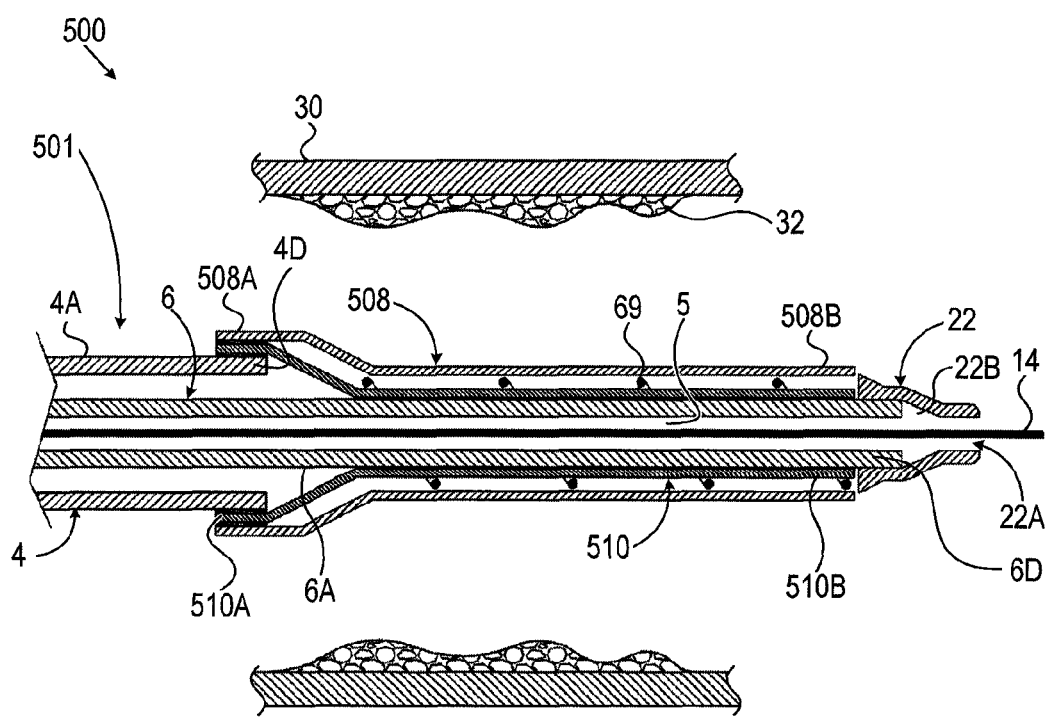
FIG. 36 is a schematic cross-sectional diagram illustrating part of a catheter with a shaft, a balloon, a sleeve having an expandable or spring-like coil wound over the balloon and under the sleeve, in which the sleeve is attached to the balloon and the balloon is sealingly attached to the shaft of the catheter, in accordance with yet another embodiment of the catheters of the present application.

The catheter 230 of FIG. 13 is a rapid exchange catheter including the connector member 212, a catheter shaft 231 including the outer conduit 204 and the angled inner conduit 206 as disclosed in detail hereinabove with respect to the catheter 202 of FIG. 10. The catheter 230 also includes a balloon 10 having a proximal end sealingly attached to the distal end 204D of the outer conduit 204 and a distal end 10B sealingly attached to the distal end 206D of the inner conduit 206. The catheter 230 also includes a perforated sleeve 80 having multiple perforations 80C therein. In accordance with the embodiment of the catheter 230 illustrated in FIG. 13, the proximal end 80A of the perforated sleeve 80 is attached to the distal end 204D of the outer conduit 204 at an attachment region which is disposed proximally to the attachment region of the proximal end 10A of the balloon 10 to the distal end 204D of the outer conduit 204. However, in accordance with another embodiment of the catheter 230, the proximal end 80A of the perforated sleeve 80 may be attached (by gluing, welding, ultrasonic welding or any other suitable attaching method known in the art) to the proximal end 10A of the balloon 10 at the region where the balloon 10 is sealingly attached to the outer conduit 204 (This alternative configuration is not shown in FIG. 13, but see the catheter 500 of FIG. 36 illustrating such an arrangement of the attachment regions). The catheter 230 also includes a substance or composition 90 disposed between the balloon 10 and the perforated sleeve 80 as shown in FIG. 13.

It is noted that, as is the case for all the embodiments of the drug/substance containing catheters of the present application, the substance (or composition) 90 may include any desired substance or combination of substances, including but not limited to, one or more drugs, one or more therapeutic substances, one or more diagnostic substances, one or more pharmaceutically acceptable carrier substance, one or more delayed release compositions, and any combinations thereof. Some non-limiting examples of components which may be included in the substance 90 are, a therapeutic substance, a diagnostic substance, a drug, a therapeutic composition, a medicament, a diagnostic composition, a physiologically active agent, a biochemically active agent, one or more living cells, DNA, RNA, a nucleic acid, a vector for delivering genetic material to cells in the treated site, anti-inflammatory agents, anti-restenosis agents, cell proliferation inhibitory agents, smooth muscle proliferation inhibiting agents (such as, Paclitaxel and sirolimus (rapamycin), everolimus, and the like), vaso-active agents, vaso dilating agents, vaso constricting agents, antibiotic agents, anti-coagulative agents, platelet aggregation inhibiting agents, anti-fibrosis agents, a pharmaceutically acceptable vehicle, a lipid based vehicle and any combinations thereof.

It is also noted that the substance (or composition) 90 may include any pharmaceutically acceptable vehicles including but not limited to hydrophilic vehicle and hydrophobic vehicles, in a viscous liquid form or in a gel form which caries any of the additional pharmacologically active ingredients or agents in solution or in a suspension. The viscosity and extrudability of the substance or composition 90 is such that the substance or composition will not excessively leak out of the perforations 80C during storage of the catheter (prior to use) and/or at the stages of operating the catheter which precede the inflation step of the balloon 10. However, the flow properties, extrudability and viscosity of the substance 90 are such that the forces exerted by the inflation of the balloon 10 when the balloon 10 is inflated under the nominal inflation pressure will be sufficient to extrude at least some of the substance 90 through the perforations 80C. The viscosity, extrudability and other flow properties of the substance 90 may be controlled by the selection of the type of vehicle used to dissolve and/or suspend the pharmaceutically active ingredients in the substance 90 and by suitably adjusting the ratio of the amount of dissolved and/or suspended active ingredient and the amount of vehicle used. Further adjustments of the flow properties, viscosity and extrudability of the substance 90 may be possible by the addition of pharmaceutically acceptable flow and viscosity modifiers, as is known in the art.

In operation, the methods of use of the catheter 230 are similar to the methods of use described hereinabove for the catheters 202 and 250. The steps of insertion into the body and navigation of the catheter through the vasculature to the treatment site, the inflation of the balloon 10 and treatment of the atheroma or lesion and the balloon deflation and capturing of debris 34 within the cavity formed between the deflated balloon 10 and the sleeve 80 and the withdrawing of the catheter from the body are as explained hereinabove in detail for the rapid exchange catheter 202 of FIG. 10. The steps of the method of applying the substance (or composition) 90 through the perforations 80C onto the lesion or treated vessel region or atheroma 32 are as disclosed hereinabove in detail for the catheter 250 of FIGS. 11-12.

After the steps of inflating the balloon 10 for compacting the atheroma or plaque or constricted region of the vessel 30 and application of the substance 90 to the plaque 32, the operator may proceed with steps of deflating of the balloon 10 (of the catheters 230 or 250) to form a cavity between the deflated balloon 10 and the perforated sleeve 80 and to trap debris 34 in the cavity as disclosed hereinabove in detail for the catheter 250 of FIGS. 11-12. The entire catheter 250 with the debris 34 trapped therein may be then withdrawn from the vasculature (or body cavity) as disclosed in detail hereinabove.

Figure 15:
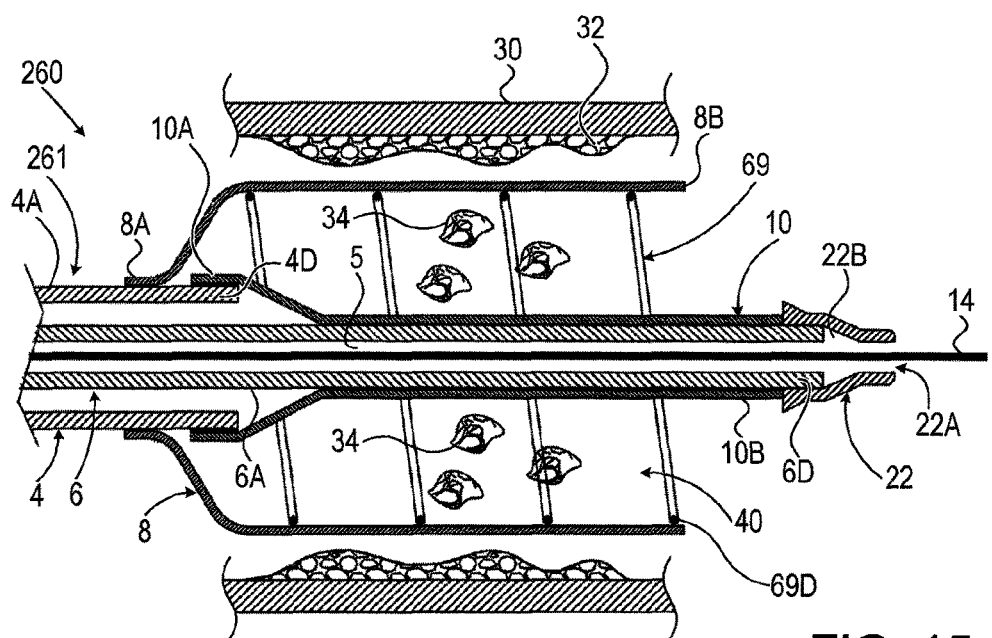

Reference is now made to FIGS. 14 and 15 which are schematic cross-sectional diagrams of part of a catheter with a balloon and a sleeve having an expandable sleeve supporting member disposed over the balloon and under the sleeve, illustrated at two different steps of operating the catheter, in accordance with another embodiment of the catheters of the present application.

In the embodiment of the catheter 260 illustrated in FIGS. 14-15, the catheter 260 includes a catheter shaft 261. The catheter shaft 261 includes an inner conduit 6 and an outer conduit 4. The catheter 260 also includes a balloon 10 which is sealingly attached to the distal end 4D of the outer conduit 4. The proximal end 8A of the sleeve 8 is attached to the outer surface 4A of the distal end 4D of the outer conduit 4. However, in an alternative embodiment of the catheter, the proximal end 8A of the sleeve 8 may be sealingly attached to the region 10A of the balloon 10 at the position at which the region 10A is attached to the outer surface 4A of the distal end 4D of the outer conduit 4 (see FIG. 36 disclosing a similar arrangement of the sleeve and balloon attachments).

A sleeve supporting member 69 (implemented as an expandable or spring-like coil in the embodiment of the catheter 260) is disposed around the balloon 10 and is disposed between the balloon 10 and the sleeve 8. The proximal end of the sleeve supporting member 69 is attached or bonded to the proximal end 10A of the balloon 10 (the attachment point is not shown for the sake of clarity of illustration). The sleeve supporting member 69 may be made from materials such as Nitinol, stainless steel, a polymer based material and the like. The sleeve supporting member 69 may shaped be a helically wound coil but may also be shaped like any other expandable framework which may be expanded by inflating the balloon 10, or which may be initially in a compressed state which is capable of expanding to a relaxed state for supporting the sleeve 8 when the sleeve 8 is in the expanded state.

Turning to FIG. 14, when the balloon 10, the sleeve 8 and the sleeve supporting member 69 are in the initial state configuration (prior to using the catheter), the balloon 10 may be folded around the inner conduit 6 (as disclosed in detail hereinabove and illustrated in FIG. 2). In the initial state configuration the sleeve 8 may be either in a non folded configuration (as shown in FIG. 2) or in a folded configuration (as shown for the sleeve 17 of in FIG. 4 hereinabove). This initial state facilitates the insertion of the balloon 10, the sleeve 8 and the sleeve supporting member 69 disposed therebetween into the vasculature or body cavity and the passing the catheter within the vasculature or body cavity until the catheter's distal end reaches the site to be treated and the balloon 10 is properly positioned in the region to be treated.

Turning to FIG. 15, when the catheter 260 has been properly navigated into the region to be treated (such as, for example, an atheromatous arterial region or arterial constriction) and the balloon 10 is properly positioned at the treatment site, the balloon 10 is inflated as disclosed hereinabove with respect to the catheter illustrated in FIG. 5. When the balloon 10 is inflated, the sleeve supporting member 69 is expanded and opened between the balloon 10 and the sleeve 8. The balloon 10 expands to its inflated state. The sleeve supporting member 69 and the sleeve 8 expand as they are being pushed radially by the expanding balloon 10, to reach their fully expanded state (or fully opened state) as best seen in FIG. 15. Once the sleeve supporting member 69 is fully expanded, it assists in keeping of the sleeve 8 open once the balloon 10 is deflated in the step of deflation of the balloon 10 to form a cavity 40 between the deflated balloon 10 and the opened sleeve 8. The use of the expandable sleeve supporting member 69 advantageously keeps the volume of cavity 40 from being reduced due to its supporting action which holds the sleeve 8 fully radially extended (or expanded).

It is noted that the use of an expandable sleeve supporting member 69 for supporting the sleeve 8 may be implemented and used in any of the types of catheters described in the present application, including but not limited to the catheters 2, 52 100, 110, 120, 130, 140, 150, 160, 170, 202, 230, 250, 352 and 400 disclosed in the present application by adding a suitable sleeve supporting member to any of these catheters. If the shape of the balloon of a catheter is different than a cylindrical shape, the shape of the sleeve supporting member may be adapted to conform to the shape of the balloon of the catheter. For example a sleeve supporting member usable with the catheter 400 having a conically tapering balloon 410 may be a conically tapering coil (not shown) and a sleeve supporting member usable with the catheter 170 having a stepped balloon 210 may be a stepped coil matching the stepped form of the balloon 210 (not shown). Such shape adaptations of the sleeve supporting members to conform to the shape of the balloon and/or sleeve shapes being used in such catheters will be clearly understandable to the person skilled in the art and are therefore not described further hereinafter.

It will be appreciated that while the shape of the sleeve supported members disclosed herein may be adapted to conform to the shape of the balloon and/or the sleeve being used in the catheter, this is by no means obligatory. For example, if the catheter 400 of FIG. 36 is modified to also include a sleeve supporting member shaped similar to the sleeve supporting member 69 (and having a uniform diameter in the non expanded state). As the expandable sleeve supporting member is pushed by the conically shaped balloon 410, the sleeve supporting member 69 will be expanding to accommodate the fully inflated shape of the conical balloon 410, such that in the fully expanded state the expanded sleeve supporting member will also have a conical shape (not shown) because different parts of the sleeve supporting member will be expanded to differing diameter in accordance with the varying diameter of the fully expanded balloon 410 along the length of the balloon 410.

Reference is now made to FIGS. 16-17. FIG. 16 is a schematic cross-sectional diagram illustrating a multi-conduit, multi-lumen balloon catheter with a catheter shaft having three conduits and three hollow passages, in accordance with an additional embodiment of the catheter of the present application. FIG. 17 is a schematic cross-section of the catheter of FIG. 16 taken along the lines XVII-XVII;

The catheter 52 includes a catheter shaft 51 including three co-axially arranged conduits as follows: an outer conduit 54, an intermediate conduit 59 and an inner conduit 56. The catheter 52 also includes a balloon 10 attached to the distal part of the catheter shaft 51, a sleeve 8 attached to the distal part of the catheter shaft 51 and a connector member 60 attached at the proximal part of the shaft 51.

The inner conduit 56 has a first hollow passage 55 therein which forms the lumen of the conduit 56. The intermediate conduit 59 is disposed within the lumen of the outer conduit 54 and the inner conduit 56 is disposed within the lumen of the intermediate conduit 59. The outer conduit 54 is preferably (but not obligatorily) a cylindrical flexible hollow tube having a lumen therein. The intermediate conduit 59 is preferably (but not obligatorily) a flexible hollow cylindrical tube having a lumen therein. The inner conduit 56 is preferably (but not obligatorily) a flexible hollow cylindrical tube having a lumen therein. The outer diameter of the intermediate conduit 59 is smaller than the diameter of the lumen of the outer conduit 54. The outer diameter of the inner conduit 56 is smaller than the inner diameter of the intermediate conduit 59. The lumen of the inner conduit 56 comprises a first hollow passage 55 extending throughout the catheter 52 for inserting and moving a guide wire 14 therethrough. A second hollow passage 61 is defined between the outer surface of the inner conduit 56 and the inner surface of the intermediate conduit 59. The second hollow passage 61 may be used for inserting and withdrawing inflation fluid into and from the balloon 10. The intermediate conduit 59 is disposed within the lumen of the outer conduit 54, forming a second hollow passage 57 defined between the inner surface of the outer conduit 54 and the outer surface of the intermediate conduit 59. The third hollow passage 57 is fluidically connected to the cavity 50 between the balloon 10 and the sleeve 8, such that suction from an external suction source (not shown) may be applied to the cavity 50 through the third hollow passage 57 to assist the capturing and or retaining of the debris 34 within the cavity 50 and/or within the third hollow passage 57.

The connector member 60 is a hollow multi-port connector having three ports, a suction port 60A, a guide wire port 60B and an inflation port 60C. The distal part of the connector member 60 is recessed to accept the proximal parts of the inner conduit 56, the outer conduit 54 and the intermediate conduit 59 therein. The proximal part of the outer conduit 54 is sealingly attached to the recessed distal end of the connector member 60 by bonding or gluing or a suitable adhesive or the like, as disclosed in detail hereinabove with respect to the outer conduit 4 and the connecting member 12 of the catheter 2. Similarly, the proximal parts of the intermediate conduit 59 and of the inner conduit 56 are sealingly attached to suitable recesses formed in the distal end of the connector member 60 by bonding or gluing or a suitable adhesive or the like, as disclosed in detail hereinabove with respect to the outer conduit 4 and the connecting member 12 of the catheter 2. The manner of attachment of the proximal parts of the inner conduit 56, the outer conduit 54 and the intermediate conduit 59 is best seen in FIG. 16.

Due to the fixed attachment of the inner conduit 56, the outer conduit 54 and the intermediate conduit 59 to the connector member 60, the inner conduit 56, the outer conduit 54 and the intermediate conduit 59 are fixed and cannot be axially or longitudinally moved with respect to each other.

The balloon 10 is disposed within the sleeve 8. The balloon 10 has a proximal balloon end 10A and a distal balloon end 10B. The proximal balloon end 10A is sealingly attached to the outer surface of the distal end of the intermediate conduit 59 and the distal balloon end 10B is sealingly attached to the outer surface of the distal end 56D of the inner conduit 56 as best seen in FIG. 16. Inflation fluid may be introduced into the lumen of the balloon 10 through an opening 62 in the inflation port 60C of the connector member 60 which fluidically communicates with the hollow passage 61. The inflation port 60C may be used for inflating and for deflating the balloon 10. An indeflator (not shown) or a syringe (not shown) filled with a suitable inflation fluid may be connected to the inflation port 60C and operated as is known in the art to inflate and/or deflate the balloon 10. The inflation fluid may enters (or exit) the hollow passage 61, through an opening 72 formed in the wall of the proximal end 59P of the intermediate conduit 59.

The sleeve 8 has a proximal end 8A and a distal end 8B. The proximal end 8A of the sleeve 8 is sealingly attached to the outer surface of the distal end of the outer conduit 54. The distal end 8B of the sleeve 8 is an open distal end which may be opened to the vascular space 77 (or to the bodily cavity into which the catheter is inserted) during certain steps of operation of the catheter 52.

The catheter 52 also includes a soft tip 22 attached at the distal end of the inner conduit 56. The structure and operation of the soft tip 22 has been described in detail hereinabove. The proximal part of the soft tip 22 may be sealingly attached (by bonding or gluing or the like) to the distal end 56D of the inner conduit 56.

In operation, the guide wire port 60B of the connector member 60 may be used for inserting a guide wire (such as, for example the guide wire 14 of FIG. 16) or a medical device 15 or a diagnostic device (such as, for example, the medical device 15 of FIGS. 34-35) through the opening 63 formed within the guide wire port 60B and through the first hollow passage 55 of the inner conduit 56. The distal end 14D of the guide wire 14 may exit through the orifice 22A at the distal end of the soft tip 22 as is best seen in FIG. 16 and the guide wire 14 may be pushed distally to reach a desired treatment site and then the catheter 52 may be advanced distally over the guide wire to reach the region to be treated, as is well known in the art.

The distal end of the outer conduit 54 has an annular opening 70. When the catheter 52 is operated, the opening 70 allows fluidic communication between the third hollow passage 57 and the vascular space 77 (such as, for example the lumen of the blood vessel, when the distal end of the catheter 52 is disposed within the vasculature). The hollow passage 57 may be used for at least two purposes. First, during the insertion of the catheter 52 into the vasculature and the advancing of the catheter 52 through a blood vessel towards a region to be treated, a contrast enhancing fluid (not shown in FIG. 16) may be injected into the bloodstream through the opening 64 formed in the suction port 60A and the third hollow passage 57 and enter the blood stream through the opening 70 and the space formed between the balloon 10 and the sleeve 8 to facilitate imaging by angiography, as is well known in the angiographic art. The contrast enhancing fluid injected through the opening 64 flows through the hollow passage 57 and may exit into the vascular space 77 and the bloodstream through the annular openings 70 of the distal end of the outer conduit 54. However, it may also be possible to inject a contrast enhancing fluid through the opening 63 of the guide wire port 60B by withdrawing the guide wire out of the catheter or by injecting the contrast enhancing fluid through the guide wire port 60B while the guide wire 14 is still disposed within the catheter by using an injecting device (not shown) that is configured to access the hollow passage 55 while sealing the opening 63 while the guide wire is disposed within the opening 63. This may be done, for example, by using an injecting needle (not shown) sealingly attached to and passing through a suitable annular gasket (not shown) configured to seal the opening 63).

The hollow passage 57 may also be used for improving, enhancing and assisting the collection of any debris 34 resulting from the treatment of the plaque 32 or atheroma of the blood vessel during the operation of the catheter 52. Suction may be applied to the suction port 60A, through the opening 64 by suitably connecting the suction port 60A to a vacuum pump or to any source of reduced pressure as is known in the art. When the balloon 10 is in the state illustrated in FIG. 16 (after the balloon 10 was first inflated to treat the plaque 32 and then deflated), a cavity 50 is formed between the outer surface of the balloon 10 and the inner surface of the opened sleeve 8 as best seen in FIG. 16. The forming of the cavity 50 is similar the forming of the cavity 40 between the balloon 10 and the sleeve 8 of the catheter 100, as disclosed in detail hereinabove and illustrated in FIGS. 5 and 6 hereinabove. During the formation of the cavity 50, a sucking action (or suction) occurs due to the deflating of the balloon 10. It is noted that this sucking action results from the formation of the cavity 50 due to the deflation of the balloon 10, without the need to apply suction from an external suction source.

Some of the debris 34 released to the blood in the vascular space 77 during the opening of the lesion, atheroma, obstruction or plaque is then withdrawn into the cavity 50 and is trapped within the cavity 50. However, not all of the debris 34 which is released during angioplasty treatment is always trapped within the cavity 50 and some of the debris 34 may remain within the bloodstream. If suction is applies to the suction port 60A during and/or after the deflation of the balloon 10, additional debris 34 may be sucked into the cavity 50 and become trapped therein due to the additional suction of additional blood carrying suspended debris 34 therein. Thus, the application of external suction (from an external suction source) through the suction port 60A may augment and increase the amount of debris 34 collected and trapped in the cavity 50 during the operation of the catheter 52. The application of suction as described herein is advantageous since the more debris 34 collected within the cavity 50 the less is the amount of debris 34 remaining in the bloodstream after treatment and the lower the risk of embolism to the patient.

Thus, the implementation of a multi-passage catheter, such as, for example, the multi-lumen catheter 52 having three hollow passages within the catheter shaft 51 enables the inflation/deflation of the balloon through the hollow passage 61 within the shaft of the catheter 52 and the introduction of any desired fluid into the bloodstream (including, but not limited to, contrast enhancing fluid, a drug, an anti-coagulant, and the like) through another hollow passage 57 or through the hollow passage 55 of the catheter 52, as well as allowing the application of suction from an external source to the hollow passage 57 of the multi-lumen catheter 52 in order to assist and increase the trapping and retaining of the debris 34 within the cavity 50. Furthermore, when suction from an external suction source (not shown) is applied to the suction port 60A, some of the debris 34 entering the cavity 50 may be further proximally sucked into and retained within the hollow passage 57. This trapping of some of the debris 34 within the passage 57 may be advantageous for several reasons. First, the capacity of the catheter 52 to trap and retain the debris 34 may be substantially increased (as compared to the capacity to trap and retain the debris 34 only within the cavity 50 formed by the deflation of the balloon 10) because the entire volume of the hollow passage 57 becomes available for retaining and containing the debris 34 (in addition to the volume of the cavity 50) when external suction is applied through the suction port 60A. This increase in volume augments and increases the capacity of the catheter 52 to trap and retain debris 34, such that more debris 34 is removed from the blood in the vascular space 77, substantially reducing the risk of embolism to the patient.

Furthermore, when external suction is applied to the suction port 60A, some of the debris 34 which was sucked into and retained within in the cavity 50 during the step of deflating of the inflated balloon 10 is further sucked proximally into the hollow passage 57 within the shaft of the catheter 52, which vacates at least some of the debris 34 from the cavity 50 into the hollow passage 57. The advantage of such proximal moving of debris 34 from the cavity 50 into the hollow passage 57 is that may reduce the possibility of releasing some of the trapped debris 34 back into the vascular space 77 and the bloodstream during the step of withdrawal of the catheter 52 out of the vasculature, thereby even further reducing the risk of patient embolism. The further proximally within the passage 57 the trapped debris 34 is disposed, the lower is the likelihood of it being released back into the blood stream during bending and/or squeezing of the shaft of the catheter 52 and of the sleeve 8, which may be caused by the step of withdrawal of the catheter from the vasculature and the proximal movements of the catheter 52 and the open sleeve 8 through the vasculature.

It is noted that while the balloon 10 of FIG. 16 is illustrated in the deflated state after it has been in the inflated state, this is done for the purpose of clarity of illustration in order to better view the structure of the distal end of outer conduit 54 and of the annular opening 70 in the distal portion of the outer conduit 54. When the catheter 52 is assembled, the balloon 10 and the sleeve 8 are in a folded or wrapped configuration (not shown in FIG. 16) which may be similar to the pre-folded configuration of the balloon 10 and the sleeve 8 of the catheter 2 of FIGS. 1-2 and the catheter 100 of FIGS. 3-4. After the catheter 52 is inserted into the vasculature and the balloon 10 is disposed within the region to be treated, the balloon 10 may be inflated by introducing inflation fluid under pressure into the inflation port 60C and fully inflating the balloon 10 and expanding the sleeve 8 to treat the lesion or atheroma as disclosed hereinabove in detail for the balloon 10 of FIG. 6.

In operation, after the insertion of the catheter 52 into the vasculature and advancing the distal catheter's end to position the balloon 10 in the region of the blood vessel to be treated, and after the step of inflating the balloon 10 of the catheter 52 (without or with deploying a stent in the vasculature as disclosed in detail hereinabove for the catheter 2 of FIG. 1 and for the catheter 160 of FIGS. 28-30, respectively), the balloon 10 may be deflated to form the cavity 50 as described in detail above. Optionally, but not obligatorily, suction from an external source such as a vacuum pump (not shown) or the like may be applied to the suction port 60A during and/or after the deflation of the balloon 10 to assist and augment the trapping and collection of debris 34 within the cavity 50. After the collection and trapping of debris 34 is performed, the catheter 52 may be withdrawn out of the vasculature and out of the body by suitably pulling the catheter 52 proximally until the catheter exits the patient's body.

Figure 18:
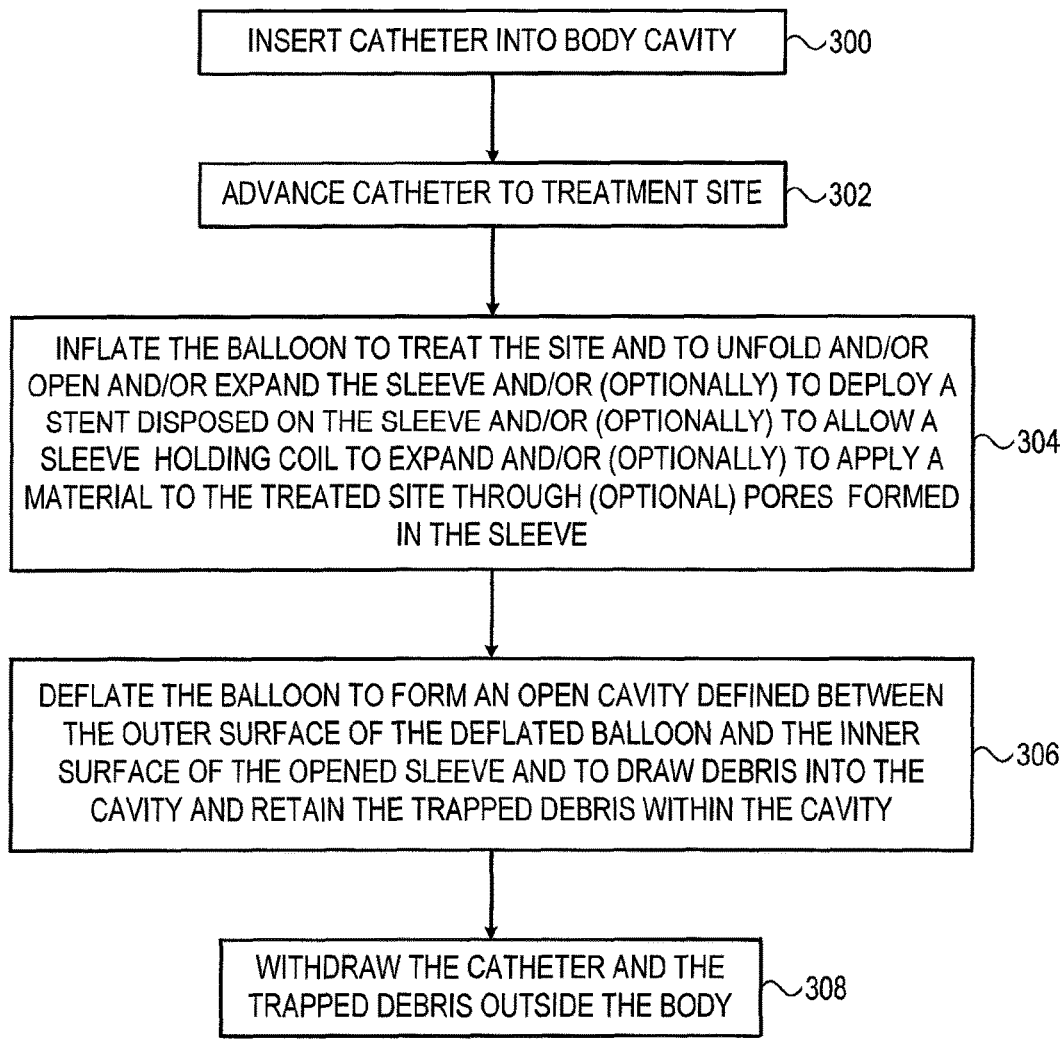
FIG. 18 is a schematic block diagram illustrating steps of a method for using the catheters of the present application in a medical procedure.

Reference is now made to FIG. 18 which is a schematic block diagram illustrating steps of a method for using the catheters of the present application in a medical procedure. In operation of the catheters disclosed hereinabove and illustrated in any of the drawing figures, the catheter is first inserted into the body and positioned within a body cavity (Step 300). Typically, the catheters disclosed in the present application may be used to open an obstruction or treat a lesion such as an atheroma in a blood vessel. However, it is noted that the catheters of the present application may be used to treat other bodily cavities, such as, but not limited to a cavity within a kidney, a ureter, a bile duct and the like. Furthermore, the bodily cavity may be a body cavity of any mammal and the catheters are definitely not limited to the treatment of bodily cavities in human patients. Nevertheless, for the sake of simplicity the following steps will be described with respect to treating a human blood vessel (such as a vein or an artery).

Before and during the step of insertion of the catheter, the balloon 10 may be folded around the innermost conduit as illustrated in any of the examples illustrated in FIGS. 1-5, 8, 11, 13, 14 and 16) The sleeve of the catheter (such as the sleeve 8 and the sleeve 80 of FIGS. 1 and 11, respectively), may also be folded around the folded balloon in one of the folded configurations illustrated in FIGS. 1, 2, 3, 4, 5, 8, 11, 13 and 14. This folded configuration of the balloon and the sleeve of the catheter reduces the crossing profile of the catheter and facilitates insertion and navigation of the distal catheter's end within the vasculature towards the site to be treated (treatment site).

After insertion of the catheter into the vasculature, (using a femoral artery approach or any other insertion method as is well known in the art), the operator advances the catheter towards the treatment site (Step 302). The pushing of the catheter may be performed over a guide wire 14 which may be inserted into the catheter prior to or after the insertion of the catheter distal end into the vasculature. The guide wire 14 may then be pushed and navigated within the vasculature to reach the treatment site (such as, for example, an arterial or venous lesion or obstruction) as is well known in the art. It is noted that the catheter may be configured as any of the over the wire (OVT) catheter (such as but not limited to the catheters 2 and 52 of FIGS. 1 and 16, respectively) or as a rapid exchange (RE) catheter (such as, but not limited to, the catheters 202 and 205 of FIGS. 10, 13, respectively). However, any of the catheters of the present application may also be inserted into the vasculature and advanced towards the treatment site without the use of a guide wire, if the specific application requires or enables this, in other words, the use of the guide wire 14 is optional and is by no means obligatory to practicing the use of the catheters disclosed in the application.

Once the distal catheters end is properly positioned within the desired treatment site (for example, by using standard angiography procedures with or without the use of contrast enhancing agents, as is known in the art), the balloon is inflated to treat the lesion (Step 304). In this step, the balloon is typically inflated to its nominal diameter in order to treat the obstruction or lesion at the treatment site. When the balloon is inflated it opens the sleeve (such as, for example the sleeve 8 or 80) to it's fully opened state (as is shown for example in FIGS. 6 and 9) by expanding and thereby unfolding the folded sleeve (in the case of folded sleeves, such as, for example the sleeve 8 of FIG. 4) and opening the sleeve to its fully open state. Alternatively, if the sleeve is of the non-folded type (such as for example, the sleeve 8 of FIG. 2), the force exerted by the radially expanding walls of the balloon 10 may also stretch and distend the sleeve from its initial small diameter state into a distended stretched state having a larger diameter by stretching and distending the material of the sleeve such that it has a final internal diameter similar to the external diameter of the balloon 10 at its nominal expanded diameter. (it is noted that during this stretching of the sleeve's wall material the length of the sleeve (along the longitudinal axis of the catheter) shortens by a certain amount while the thickness of the wall of the sleeve diminishes as a result of the stretching (as disclosed in detail hereinabove).

In Step 304, if the sleeve is folded as shown in FIG. 4, but it's fully opened internal diameter is equal to or substantially similar to the external nominal diameter of the fully inflated balloon 10, the inflating of the balloon 10 to its nominal fully inflated diameter will essentially unfold and open the sleeve with no or almost no stretching of the sleeve (in this type of catheter the sleeve is made of a substantially non-stretchable material as disclosed in detail hereinabove).

Typically, irrespective of the type of sleeve being used, once the sleeve is fully opened (either by stretching only or by unfolding only or by both unfolding and stretching), the sleeve will remain in the opened state whether the balloon is fully inflated or is later deflated).

In step 304, if the catheter initially also includes a stent (not shown) disposed on the folded or non-folded sleeve, the expansion of the balloon being inflated and the opening (and/or the stretching) of the sleeve by the expanding balloon will radially expand the stent and push it towards the vessel wall and the lesion resulting in the deployment of the stent within the lesion as is well know in the art). Such a stent may be any type of stent known in the art.

Furthermore, in step 304, if the catheter is one of the drug delivering catheters disclosed herein (such as, but not limited to the catheters 250 or 205 of FIGS. 11 and 13, respectively), when the balloon is expanded to its nominal inflation pressure it expands and pushes against the layer of material (such as the drug or therapeutic composition or diagnostic composition disposed between the balloon 10 and the sleeve 80) and will thereby extrude some of the drug or material, through the pores 80C formed within the wall of the sleeve 80, resulting in the application of the extruded material to the lesion or treated site on the blood vessel wall.

Furthermore, in step 304, if the catheter includes a sleeve supporting member 69 as disclosed in catheter 260 of FIGS. 14 and 15, the inflation of the balloon 10 to its nominal inflated diameter will plastically expand the sleeve supporting member 96 from an initial small diameter state (as illustrated in FIG. 14) to an open (expanded) state (as illustrated in detail in FIG. 15) when the sleeve supporting member 96 is made from a plastically expandable material as disclosed. Alternatively, if the sleeve supporting member 96 is made from a material which strives to expand (due to its being pre-wound tightly between the sleeve and the balloon such that it is held by the friction of the sleeve and balloon and prevented from expanding radially to an open state, the inflating of the balloon will assist the spring-like wound coil of the sleeve supporting member 69 to expand by pushing it radially while simultaneously opening and expanding the sleeve 8 into the open state thereby enabling the sleeve supporting member 96 to expand into its opened expanded state (as seen in FIG. 15). Once the sleeve supporting member 96 is fully expanded, it will stay expanded and assist and support the opened sleeve 8 to retain its open state, irrespective of the coil type being used.

After the inflation of the balloon 10 to its nominal inflated diameter and treatment of the lesion by any of the treatment types disclosed hereinabove or by any combination of these treatment means, the operator deflates the balloon 10 to form an open cavity (such as but not limited to the cavity 40 of FIG. 7) between the outer surface of the deflated balloon 10 and the inner surface of the opened sleeve 8 (step 306). As the sleeve 8 remains open and the balloon 10 shrinks in diameter during the deflating thereof the volume of the cavity increases thereby creating a suction which may draw debris 34 into the cavity and retain the trapped debris within the cavity. The debris 34 may be in the form of any particulate matter or particles or mucus or any other material released during the treatment of the lesion into the fluid in the cavity (a blood vessel in the exemplary, non-limiting case described herein for treating the atheroma), the debris may be sucked into the cavity 40 mixed with an amount of blood (or any other biological fluid present in another type of bodily cavity being treated) and may be retained and trapped within the cavity.

After the balloon is deflated and the debris is trapped within the cavity as described above, the catheter including the debris trapped within the catheter are withdrawn outside of the body (Step 308). This is achieved by gently pulling the entire catheter proximally until it exits the vasculature (or other bodily cavity). If a guide wire has been used, during this step the catheter may be withdrawn out of the body first, followed by the guide wire 14 which may be withdrawn out of the body after the withdrawal of the catheter. Alternatively, the guide wire 14 may first be withdrawn out of the body followed by withdrawing of the catheter. Alternatively, both the catheter and the guide wire may be withdrawn out of the body together. In a fourth alternative, the guide wire (if used) may be withdrawn out of the body at any step following the placement of the catheters distal end at the treatment site.

It is noted that the catheters of the present application may include any combination of the components and features of the different catheters disclosed herein and illustrated in the drawing figures. For Example, in accordance with one possible embodiment of the catheters, a rapid exchange catheter may be constructed which includes a perforated or porous sleeve 80 and a medical composition in addition to a coil (such as the coil 96 of FIG. 14), and a deployable stent (not shown) disposed on the external surface of the sleeve 80.

For example, in accordance with another possible embodiment of the catheter, an over the wire catheter (see FIG. 1) may be constructed which includes a perforated or porous sleeve 80 and a medical composition in addition to a sleeve supporting member (such as the sleeve supporting member 96 of FIG. 14, and a deployable stent (not shown) disposed on the external surface of the sleeve 80. Both of the above described embodiments may or may not include the soft tip 22 with or without the sleeve retaining member 27D. Therefore, the person skilled in the art will appreciate that different various components may be mixed and matched such that any possible catheter types (RE and OVT) may or may not include any combination of sleeve type (such as, folded sleeve, non-folded sleeve, stretchable sleeve and non-stretchable sleeve, small diameter stretchable non folded sleeve, and large diameter non-stretchable folded sleeve), sleeve supporting member type (an expandable helical coil made of plastically expandable material and a preformed pre-coiled elastic coil), any type of known stent disposed on the sleeve, and the like. Any number of these features may be combined or mixed and matched by suitable adaptation of the catheter to include or exclude any of these features and components at will.

Therefore, the different steps disclosed hereinabove in FIG. 18 may or may not include certain actions depending on the specific embodiment of the catheter being used. For example, if the embodiment of the catheter being used does not include a perforated sleeve 80 and drug, but instead includes a non-perforated sleeve 8, Step 304 will not include the application of a drug to the lesion or the treated region. In another example, if the catheter does not include the sleeve supporting member 96 then step 304 will not include the expanding of the sleeve supporting member 96. In another example, if the sleeve 8 is of the small diameter stretchable sleeve 8 as illustrated in FIG. 2, then step 304 will include the stretching of the sleeve 8 by the balloon 10 but will not include the unfolding of the sleeve as the sleeve 8 in this embodiment is not initially folded (see FIG. 2). Similarly, other added or omitted components from the catheter structure may result in certain actions occurring or not-occurring, respectively, depending on the specific components included or excluded from the particular catheter embodiment.

It is noted that while the multi-conduit catheter 52 of FIG. 16 is implemented as an over the wire (OVT) catheter. The multi-conduit catheters disclosed herein may also be implemented as rapid exchange catheters.

Reference is now made to FIGS. 19, 20 and 21. FIG. 19 is a cross-sectional diagram illustrating a rapid exchange multi-lumen catheter having a three conduit shaft, a sleeve and a balloon with three hollow passages formed within the catheter shaft, in accordance with another embodiment of the catheter of the present application. FIG. 20 is a schematic cross-section of the catheter of FIG. 19 taken along the lines XX-XX, and FIG. 21 is a schematic cross-section of the catheter of FIG. 19 taken along the lines XXI-XXI.

The catheter 352 includes a catheter shaft 351 including three conduits as follows: an outer conduit 354, an intermediate conduit 359 and an inner conduit 356. The catheter 352 also includes a balloon 10 attached to the distal part of the catheter shaft 351, a sleeve 8 attached to the distal part of the catheter shaft 351 and a connector member 360 attached at the proximal part of the shaft 351.

The inner conduit 356 is disposed within the intermediate conduit 359 and the intermediate conduit 359 is disposed within the outer conduit 354 such that the distal end 356D of the inner conduit 356 extends distally beyond the distal end 359D of the intermediate conduit 359, the inner conduit 356 has a straight part 356S that protrudes distally beyond the distal end 359D of the intermediate conduit 359 and an angled proximal part 356A that sealingly pierces through the wall of the intermediate conduit 359 and also sealingly pierces through the wall of the outer conduit 354 to form an opening 315 in the outer conduit 354. The opening 315 may be used for inserting a guide-wire 14 (or a medical device, such as the medical device 15 of FIG. 34) therethrough. The lumen of the inner conduit 356 forms a first hollow passage 355. The space between the inner conduit 356 and the intermediate conduit 359 defines a second hollow passage 320. The intermediate conduit 359 is disposed within the lumen of the outer conduit 354 such that the space defined between the intermediate conduit 359 and outer conduit 354 comprises the third hollow passage 357. The proximal end 8B of the sleeve 8 is sealingly attached to the distal end 354D of the outer conduit 354, the proximal end 10A of the balloon 10 is sealingly attached to the distal end 359D of the intermediate conduit 359 and the distal end 10B of the balloon 10 is sealingly attached to the distal end 356D of the inner conduit 356 that protrudes beyond the distal end 359D of the intermediate conduit 359.

The outer conduit 354 is preferably (but not obligatorily) a cylindrical flexible hollow tube having a lumen therein. The intermediate conduit 359 is preferably (but not obligatorily) a flexible hollow cylindrical tube having a lumen therein. The inner conduit 356 is preferably (but not obligatorily) a flexible hollow cylindrical tube having a lumen therein. The outer diameter of the intermediate conduit 359 is smaller than the diameter of the lumen of the outer conduit 354. The outer diameter of the inner conduit 356 is smaller than the inner diameter of the intermediate conduit 359. The second hollow passage 320 may be used for inserting and withdrawing inflation fluid into and from the balloon 10. The intermediate conduit 359 is disposed within the lumen of the outer conduit 354, forming the second hollow passage 357 defined between the inner surface of the outer conduit 354 and the outer surface of the intermediate conduit 359. The third hollow passage 357 is fluidically connected to the cavity 340 defined between the balloon 10 and the sleeve 8 when the sleeve 8 is in the expanded state and the balloon 10 is in a deflated state (as illustrated in FIG. 19), such that suction from an external suction source (not shown) may be applied to the cavity 340 through the third hollow passage 357 to assist the capturing and or retaining of the debris 34 within the cavity 3500 and/or within the third hollow passage 357.

The connector member 360 is a hollow multi-port connector having two ports, a suction port 360A, and an inflation port 360C. The distal part of the connector member 360 is recessed to accept the proximal parts of the outer conduit 354 and the intermediate conduit 359 therein. The proximal end 354P of the outer conduit 354 is sealingly attached to the recessed distal end of the connector member 360 by bonding or gluing or a suitable adhesive or the like, as disclosed in detail hereinabove with respect to the outer conduit 4 and the connecting member 12 of the catheter 2. Similarly, the proximal end 359P of the intermediate conduit 359 is sealingly attached to a suitable recess formed in the distal end of the connector member 360 by bonding or gluing or a suitable adhesive or the like, as disclosed in detail hereinabove with respect to the outer conduit 4 and the connecting member 12 of the catheter 2. The manner of attachment of the proximal parts of the outer conduit 354 and the intermediate conduit 359 is best seen in FIG. 19.

Due to the fixed attachment of the inner conduit 56 to the walls of the intermediate conduit 359 and the outer conduit 354, and to the fixed attachment of the outer conduit 354 and the intermediate conduit 359 to the connector member 360, the inner conduit 356, the outer conduit 354 and the intermediate conduit 359 are fixed in place and cannot be axially (longitudinally) moved with respect to each other. However, since the inner conduit 356, the intermediate conduit 359 and the outer conduit 354 of the shaft 351 are made from flexible and bendable materials, the shaft 351 may be bent and flexed sideways during insertion into the body to accommodate bends and turns and/or bifurcations in the body cavities or in the vasculature into which the catheter 352 is inserted The balloon 10 is disposed within the sleeve 8. The balloon 10 has a proximal balloon end 10A and a distal balloon end 10B. The proximal balloon end 10A is sealingly attached to the outer surface of the distal end 359D of the intermediate conduit 359 and the distal balloon end 10B is sealingly attached to the outer surface of the distal end 356D of the inner conduit 356 as best seen in FIG. 19. Inflation fluid may be introduced into the lumen of the balloon 10 through an opening 362 in the inflation port 360C of the connector member 360 which fluidically communicates with the hollow passage 320. The inflation port 360C may be used for inflating and for deflating the balloon 10. An indeflator (not shown) or a syringe (not shown) filled with a suitable inflation fluid may be connected to the inflation port 360C and operated as is known in the art to inflate and/or deflate the balloon 10. The inflation fluid may enter (or exit) the hollow passage 320, through an opening 372 at the proximal end 359P of the intermediate conduit 359.

The sleeve 8 has a proximal end 8A and a distal end 8B. The proximal end 8A of the sleeve 8 is sealingly attached to the outer surface of the distal end 354D of the outer conduit 354. The distal end 8B of the sleeve 8 is an open distal end which may be opened to the vascular space 77 (or to the bodily cavity into which the catheter is inserted) during certain steps of operation of the catheter 352.

The catheter 352 also includes a soft tip 22 attached at the distal end of the inner conduit 356. The structure and operation of the soft tip 22 has been described in detail hereinabove. The proximal part of the soft tip 22 may be sealingly attached (by bonding or gluing or the like) to the distal end 356D of the inner conduit 356.

In operation, the opening 315 in outer surface of the outer conduit 354 may be used for inserting a guide wire (such as, for example the guide wire 14 of FIG. 19) or a medical device 15 or a diagnostic device (such as, for example, the medical device 15 of FIGS. 34-35) and into the first hollow passage 355 of the inner conduit 356. The distal end 14D of the guide wire 14 may exit through the orifice 22A at the distal end of the soft tip 22 9 and the guide wire 14 may be pushed distally to reach a desired treatment site and then the catheter 352 may be advanced distally over the guide wire 14 to reach the region to be treated, as is well known in the art of RE catheters.

When the catheter 352 is operated, the opening 70 allows fluidic communication between the hollow passage 357 and the vascular space 77 (such as, for example the lumen of the blood vessel when the distal end of the catheter 52 is disposed within the vasculature). The hollow passage 357 may be used for at least two purposes. First, during the insertion of the catheter 52 into the vasculature and the advancing of the catheter 52 through a blood vessel towards a region to be treated, a contrast enhancing fluid (not shown) may be injected into the bloodstream through the opening 364 formed in the suction port 360A and through the third hollow passage 357 and enter the blood stream through the opening 70 and through the space formed between the balloon 10 and the sleeve 8 to facilitate imaging by angiography, as is well known in the angiographic art. The contrast enhancing fluid injected through the opening 364 flows through the hollow passage 57 and may exit into the vascular space 77 and the bloodstream through the 70 of the distal end of the outer conduit 454. However, it may also be possible to inject a contrast enhancing fluid through the opening 315 by withdrawing the guide wire 14 out of the catheter shaft 351 or by injecting the contrast enhancing fluid through the opening 315 while the guide wire 14 is still disposed within the catheter 352 by using an injecting device (not shown) that is configured to access the hollow passage 55 while sealing the opening 63 while the guide wire is disposed within the opening 63. This may be done, for example, by using an injecting needle (not shown) sealingly attached to and passing through a suitable annular gasket (not shown) configured to seal the opening 63).

The hollow passage 357 may also be used for improving, enhancing and assisting the collection of any debris 34 resulting from the treatment of the plaque 32 or atheroma of the blood vessel during the operation of the catheter 352. Suction may be applied to the suction port 360A, through the opening 364 by suitably connecting the suction port 360A to a vacuum pump or to any source of reduced pressure (suction source) as is known in the art. When the balloon 10 is in the state illustrated in FIG. 19 (after the balloon 10 was first inflated to treat the plaque 32 and then deflated), a cavity 340 is formed between the outer surface of the balloon 10 and the inner surface of the opened sleeve 8 as best seen in FIG. 19. The forming of the cavity 340 is similar the forming of the cavity 40 between the balloon 10 and the sleeve 8 of the catheter 100, as disclosed in detail hereinabove and illustrated in FIGS. 5 and 6 hereinabove. During the formation of the cavity 340, a sucking action occurs due to the deflating of the balloon 10 while the sleeve 8 is in an expanded state. It is noted that this sucking action results from the formation of the cavity 340 due to the deflation of the balloon 10, without the need to apply suction from an external suction source.

Some of the debris 34 released to the blood in the vascular space 77 during the opening and/or other treatment of the lesion, atheroma, obstruction or plaque is then withdrawn into the cavity 340 and is trapped within the cavity 340. However, not all of the debris 34 which is released during angioplasty treatment is always trapped within the cavity 340 and some of the debris 34 may remain within the bloodstream. If suction is applies to the suction port 360A during and/or after the deflation of the balloon 10, additional debris 34 may be sucked into the cavity 340 and become trapped therein due to the additional suction of additional blood carrying suspended debris 34 therein. Thus, the application of external suction (from an external suction source) through the suction port 360A may augment and increase the amount of debris 34 collected and trapped in the cavity 340 during the operation of the catheter 352. The application of suction as described herein is advantageous since the more debris 34 collected within the cavity 340 the less is the amount of debris 34 remaining in the bloodstream after treatment and the lower the risk of embolism to the patient.

Thus, the implementation of a rapid exchange multi-passage catheter, such as, for example, the multi-conduit catheter 352 enables the inflation/deflation of the balloon through the hollow passage 361 within the shaft of the catheter 352 and the introduction of any desired fluid into the bloodstream (including, but not limited to, contrast enhancing fluid, a drug, an anti-coagulant, and the like) through another hollow passage 357 or through the hollow passage 355 of the catheter 352, as well as allowing the application of suction from an external source to the hollow passage 357 of the catheter 352 in order to assist and increase the trapping and retaining of the debris 34 within the cavity 340. Furthermore, when suction from an external suction source (not shown) is applied to the suction port 360A, some of the debris 34 entering the cavity 340 may be further proximally sucked into and retained within the hollow passage 357. This trapping of some of the debris 34 within the passage 357 may be advantageous for several reasons. First, the capacity of the catheter 352 to trap and retain the debris 34 may be substantially increased (as compared to the capacity to trap and retain the debris 34 only within the cavity 340 formed by the deflation of the balloon 10) because the entire volume of the hollow passage 357 becomes available for retaining and containing the debris 34 (in addition to the volume of the cavity 340) when external suction is applied through the suction port 360A. This increase in volume augments and increases the capacity of the catheter 352 to trap and retain debris 34, such that more debris 34 is removed from the blood in the vascular space 77 after treatment, substantially reducing the risk of embolism to the patient.

Furthermore, when external suction is applied to the suction port 360A, some of the debris 34 which was sucked into and retained within in the cavity 340 during the step of deflating of the inflated balloon 10 and the formation of the cavity 340 is further sucked proximally into the hollow passage 357 within the shaft of the catheter 352, which vacates at least some of the debris 34 from the cavity 340 into the hollow passage 357. The advantage of such proximal moving of debris 34 from the cavity 340 into the hollow passage 357 is that such vacating may reduce the possibility of releasing some of the trapped debris 34 back into the vascular space 77 and into the bloodstream during the step of withdrawal of the catheter 352 out of the vasculature, thereby even further reducing the risk of patient embolism. The further proximally within the passage 357 the trapped debris 34 is disposed, the lower is the likelihood of it being released back into the blood stream during bending and/or squeezing of the shaft 351 and the sleeve 8 of the catheter 352, which may be caused by the step of withdrawal of the catheter from the vasculature and the proximal movements of the shaft 351 and the open sleeve 8 through the vasculature.

It is noted that while the balloon 10 of FIG. 19 is illustrated in the deflated state (after it has been in the inflated state and then deflated), this is done for the purpose of clarity of illustration in order to better view the structure of the distal end of outer conduit 354 and of the annular opening 70 in the distal portion of the outer conduit 354. When the catheter 352 is assembled, the balloon 10 and the sleeve 8 are in a folded or wrapped configuration (not shown in FIG. 19) which may be similar to the pre-folded configuration of the balloon 10 and the sleeve 8 of the catheter 2 of FIGS. 1-2 and the catheter 100 of FIGS. 3-4. After the catheter 352 is inserted into the vasculature and the balloon 10 is disposed within the region to be treated, the balloon 10 may be inflated by introducing inflation fluid under pressure into the inflation port 360C for fully inflating the balloon 10 and expanding the sleeve 8 to treat the lesion or atheroma as disclosed hereinabove in detail for the balloon 10 of FIG. 6.

In operation, after the insertion of the catheter 352 into the vasculature and advancing the distal catheter's end to position the balloon 10 in the region of the blood vessel to be treated, and after the step of inflating the balloon 10 of the catheter 352 (without or with deploying a stent in the vasculature as disclosed in detail hereinafter for the catheter 160 of FIGS. 28-30, respectively), the balloon 10 may be deflated to form the cavity 340 as described in detail above. Optionally, but not obligatorily, suction from an external source such as a vacuum pump (not shown) or the like may be applied to the suction port 360A during and/or after the deflation of the balloon 10 to assist and augment the trapping and collection of debris 34 within the cavity 340 (and also possibly within the hollow passage 357). After the collection and trapping of debris 34 is performed, the catheter 352 may be withdrawn out of the vasculature and out of the body by suitably pulling the catheter 352 proximally until the catheter exits the patient's body.

It is also noted that while the catheters 2 and 100 of FIGS. 1 and 3, respectively, disclose a balloon 10 having a distal end 10B extending distally beyond the distal end of the sleeve 8 of the catheters, this is by no means obligatory, and the catheters of the present application may also be constructed such that the distal end of the sleeve of the catheter extends distally beyond the distal end of the balloon, or alternatively, the distal ends of the balloon and the sleeve may extend to the same distance along longitudinal dimension of the catheter when the balloon is in the non-inflated state (prior to inflating the balloon). Similarly, when the balloon is in the inflated state or when the balloon is in the deflated state (after the balloon is inflated and then deflated to form the cavity), the distal end of the open sleeve may either extend distally beyond the distal end of the balloon or may extend distally to the same distance of the distal end of the balloon along the longitudinal dimension of the catheter, or alternatively, the distal end of the balloon may extend distally beyond the distal end of the sleeve along the longitudinal dimension of the catheter.

Practically, the length (longitudinal dimension) of the balloon and/or the sleeve of the catheter may be selected such that a desired one of the above alternative configurations is achieved. Alternatively, the position of the attachment regions of the balloon and/or the sleeve to the distal end of the shaft may be arranged such that a desired one of the above alternative configurations is achieved. Additionally and/or alternatively, both the longitudinal dimensions of the balloon and/or sleeve and the position of the attachment regions of the balloon and/or the sleeve to the distal end of the catheter shaft may be selected to achieve any of the above described configurations. Thus, the catheters of the present invention may be constructed by using any and all combinations of different dimensions of the sleeve and/or the balloon and any suitable combinations of arrangement of the attachment regions of the proximal ends of the balloon and the sleeve to the distal end of the catheter shaft. Some non-limiting examples of such sleeve and balloon arrangements are illustrated in the following FIGS. 22-25

Reference is now made to FIG. 22 which is a cross-sectional diagram illustrating, part of a catheter 120 including a double conduit shaft, a balloon and a sleeve having a distal end that extends distally along the catheter shaft to the same longitudinal position of the distal end of the balloon when the balloon is in the deflated state, in accordance with another embodiment of the catheter of the present application.

The catheter 120 (only the distal part of the catheter 120 is illustrated in FIG. 22) may be similar to any of the catheters 2 and 100, except that while in the catheters 2 and 100 the distal end 10B of the balloon 10 extends distally beyond the distal end 8B of the sleeve 8 when the balloon is in the deflated state, in the catheter 120 the distal end 28B of the sleeve 28 extends distally along the shaft 121 of the catheter 120 to the same longitudinal position of the distal end 10B of the balloon 10 when the balloon 10 is in the deflated state. It is noted that the catheter 120 may be configured as a OVT catheter (similar to the configuration of the OVT catheters 2 and 100) or as a rapid exchange catheter (similar to the configuration of the RE catheter 202).

Figure 23:
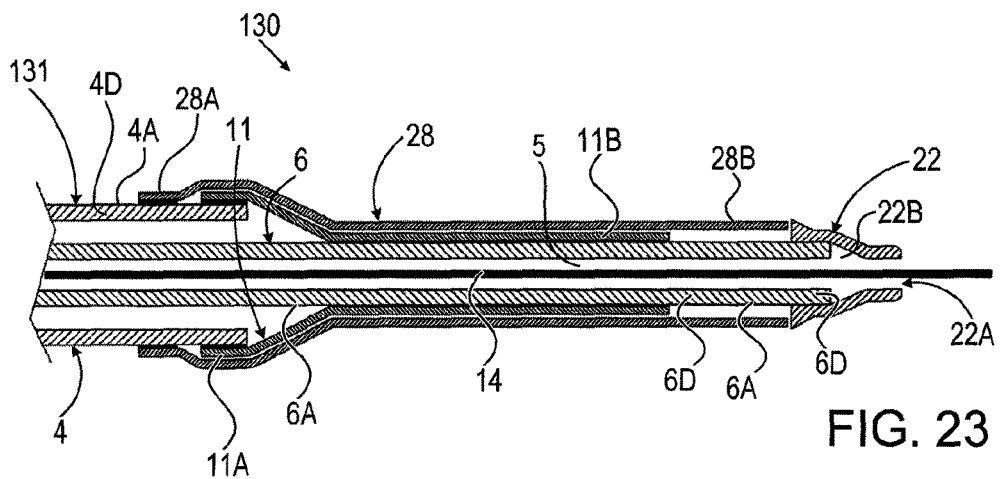
FIG. 23 is a schematic cross-section illustrating part of a catheter having a double conduit shaft, a balloon and a sleeve having a distal end such that the distal end of the balloon extends distally beyond the distal end of the sleeve when the balloon is in the deflated state, in accordance with another embodiment of the catheter of the present application.

Reference is now made to FIG. 23 which is a schematic cross-section illustrating part of a catheter 130 having a double conduit shaft, a balloon and a sleeve having a distal end such that the distal end of the balloon extends distally beyond the distal end of the sleeve when the balloon is in the deflated state, in accordance with another embodiment of the catheter of the present application.

The catheter 130 (only the distal part of the catheter 130 is illustrated in FIG. 23) may be similar to the catheter 120, except that the catheter 130 includes a balloon 11 (different than the balloon 10 of the catheter 120). While in the catheter 120 the distal end 28B of the sleeve 28 extends distally along the shaft 121 of the catheter 120 to the same longitudinal position of the distal end 10B of the balloon 10 when the balloon 10 is in the deflated state, in the catheter 130 the distal end 28B of the sleeve 28 extends distally beyond the distal end 11B of the balloon 11 when the balloon 11 is in the deflated state. It is noted that the catheter 130 may be configured as an OVT catheter (similar to the configuration of the OVT catheters 2 and 100) or as a rapid exchange catheter (similar to the configuration of the RE catheter 202).

Figure 24:
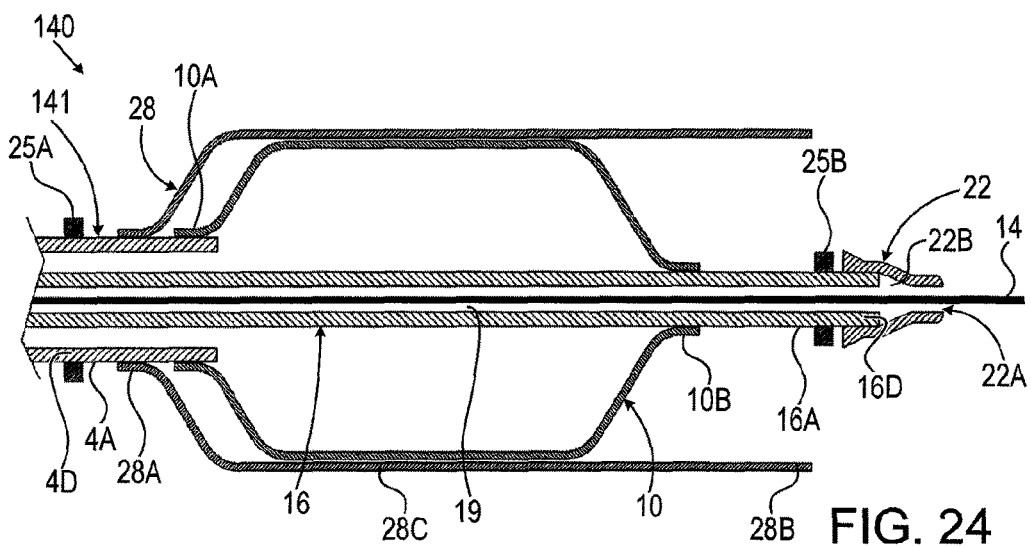
FIG. 24 is a schematic cross-section illustrating part of a catheter having a double conduit shaft, a balloon and a sleeve having a distal end that extends distally beyond the distal end of the balloon when the balloon is in the inflated state, in accordance with another embodiment of the catheter of the present application.

Reference is now made to FIG. 24 which is a schematic cross-section illustrating part of a catheter 140 having a double conduit shaft, a balloon and a sleeve having a distal end that extends distally beyond the distal end of the balloon when the balloon is in the inflated state, in accordance with another embodiment of the catheter of the present application.

The catheter 140 includes a shaft 141 having an outer conduit 4 and an inner conduit 16 disposed within the lumen of the outer conduit 4. The catheter 140 also has an inflatable balloon 10 having a proximal end 10A sealingly attached to the outer surface 4A of the distal end 4D of the outer conduit 4 and a distal end 10B sealingly attached to the outer surface 16A of the distal end 16D of the inner conduit 16. The length of the sleeve 28 and/or the length of the balloon 10 and/or the positions of attachment of the balloon 10 and of the sleeve 28 to the inner conduit 16 and/or to the outer conduit 4 may be arranged such that the distal end 28B of the sleeve 28 extends distally beyond the distal end 10B of the balloon 10 when the balloon 10 is in the inflated state.

It is noted that the catheter 140 (only the distal part thereof is illustrated in FIG. 24) may be configured as a OVT catheter (similar to the configuration of the OVT catheters 2 and 100) or as a rapid exchange catheter (similar to the configuration of the RE catheter 202).

The catheter 140 also includes (optional) radio-opaque markers, as is known in the art of angioplasty. Preferably (but not obligatorily), a radio-opaque marker 25A is attached to the inner conduit 16 near the point of attachment between the proximal end 10A of the balloon 10 and the distal end 4D of the outer conduit 4 and another radio-opaque marker 25B is attached to the outer surface 16A of the distal end 16D of the inner conduit 16 near the distal end 10B of the balloon 10 (possibly, but not obligatorily, adjacent to the proximal end of the soft tip 22). In this way, the radio-opaque markers 25A and 25B assist in the positioning of the balloon 10 within the blood vessel, during the angioplasty procedure by enabling the detection and visualization of the ends of the balloon 10 on the angiogram when positioning of the catheter. While the radio-opaque markers 25A and 25B may be shaped as annular or ring-like structures surrounding the outer conduit 4 and the inner conduit 16, respectively, any other shape or configuration of the radio-opaque markers known in the art may be used.

Figure 25:
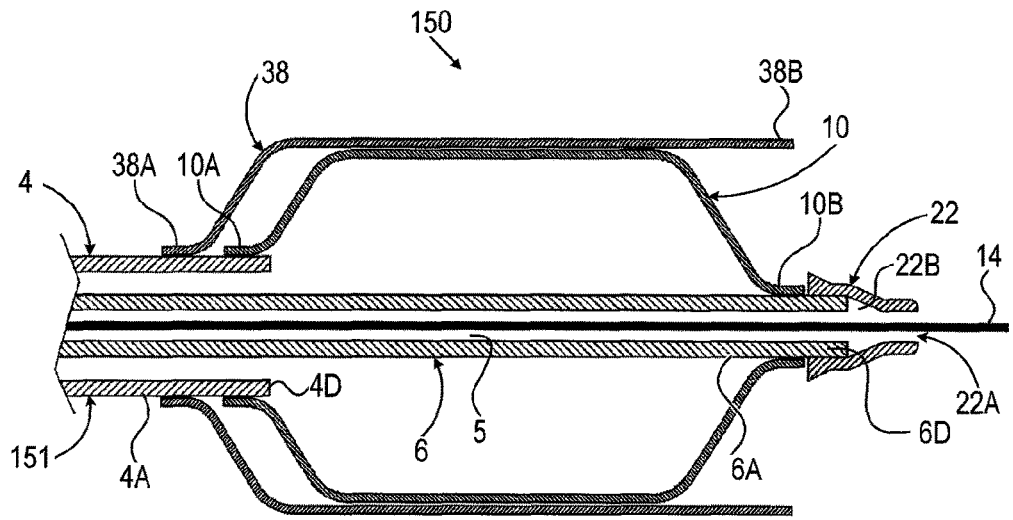
FIG. 25 is a schematic cross-section illustrating part of a catheter having a double conduit shaft a balloon and a sleeve having a distal end that extends distally to the same longitudinal position of the distal end of the balloon when the balloon is in the inflated state, in accordance with another embodiment of the multi-lumen catheters of the present application.

Reference is now made to FIG. 25 which is a schematic cross-section illustrating part of a catheter 150 having a double conduit shaft a balloon and a sleeve having a distal end that extends distally to the same longitudinal position of the distal end of the balloon when the balloon is in the inflated state, in accordance with another embodiment of the catheters of the present application.

The catheter 150 includes a shaft 151 having an outer conduit 4 and an inner conduit 6 disposed within the lumen of the outer conduit 4. The catheter 150 also has an inflatable balloon 10 having a proximal end 10A sealingly attached to the outer surface 4A of the distal end 4D of the outer conduit 4 and a distal end 10B sealingly attached to the outer surface 6A of the distal end 6D of the inner conduit 6. The catheter 150 also includes a sleeve 38 surrounding the balloon 10. The proximal end 38A of the sleeve 38 is sealingly attached to the surface 4A of the distal end 4D of the outer conduit 4. The distal end 38B of the sleeve 38 is an open end. The length of the sleeve 38 and/or the length of the balloon 10 and/or the positions of attachment of the balloon 10 and of the sleeve 38 to the inner conduit 6 and/or to the outer conduit 4 may be arranged such that the distal end 38B of the sleeve 38 extends distally to the same longitudinal position of the distal end 10B of the balloon 10 when the balloon 10 is in the inflated state.

It is noted that the catheter 150 (only the distal part thereof is illustrated in FIG. 25) may be configured as a OVT catheter (similar to the configuration of the OVT catheters 2 and 100) or as a rapid exchange catheter (similar to the configuration of the RE catheter 202).

It will be appreciated that while in the catheter 260 (of FIG. 15) the most distal part 69D of the distal end of the sleeve supporting member 69 co-extends to the same distance of the distal end 8B of the sleeve 8 when the sleeve is in the expanded state, this is by no means obligatory and that other, different arrangements of the sleeve supporting member and the sleeve may also be used in constructing the catheters of the present application.

Figure 26:
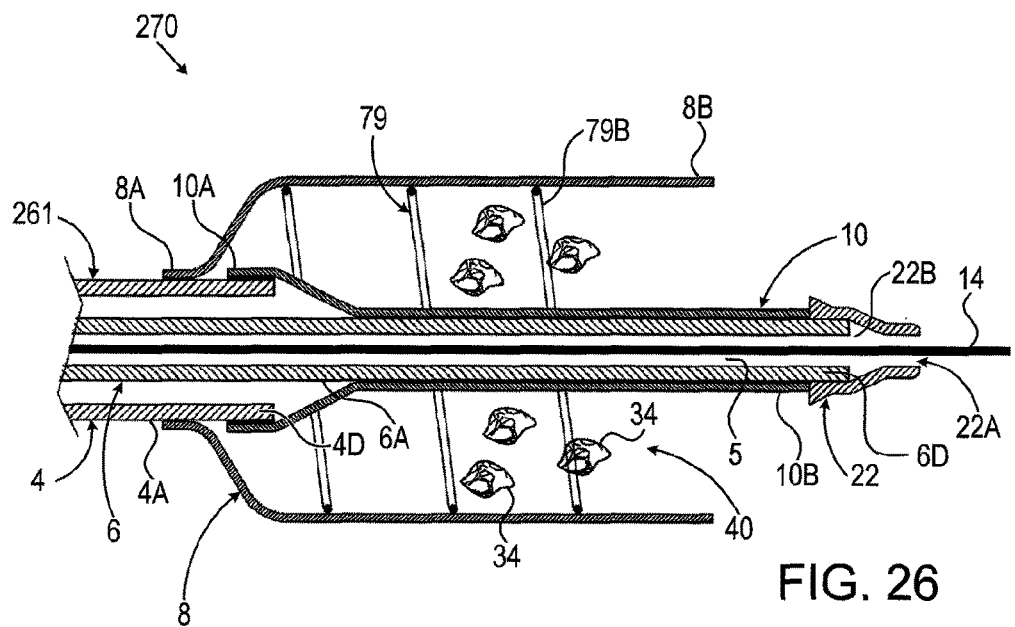
FIG. 26 is a schematic cross-section illustrating part of a catheter having a double conduit shaft, a balloon, a sleeve and a sleeve supporting member arranged such that the distal end of the sleeve extends distally beyond the distal end of the sleeve supporting member when the sleeve is in the expanded state.

Reference is now made to FIG. 26 which is a schematic cross-section illustrating part of a catheter having a double conduit shaft, a balloon, a sleeve and a sleeve supporting member arranged such that the distal end of the sleeve extends distally beyond the distal end of the sleeve supporting member when the sleeve is in the expanded state, in accordance with another embodiment of the catheters of the present application.

The catheter 270 is similar in construction and operation to the catheter 260 of FIG. 15, except that the sleeve supporting member 79 is shorter in length than the sleeve supporting member 69 of the catheter 260. Therefore, in the catheter 270, the distal end 8B of the sleeve 8 extends distally beyond the distal end 79B of the sleeve supporting member 79 when the sleeve 8 is in the expanded state. It is noted that the catheter 270 (only the distal part thereof is illustrated in FIG. 26) may be configured as a OVT catheter (similar to the configuration of the OVT catheters 2 and 100) or as a rapid exchange catheter (similar to the configuration of the RE catheter 202).

Figure 27:
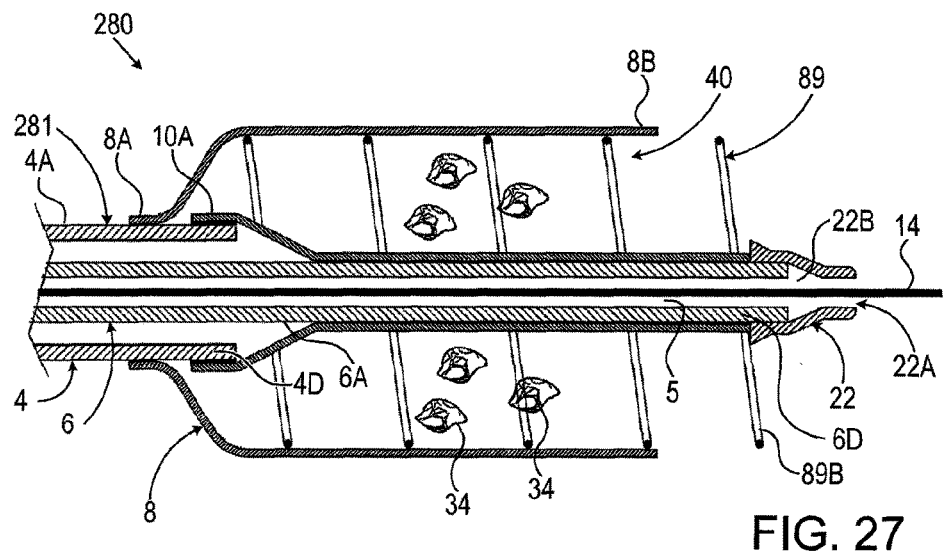
FIG. 27 is a schematic cross-section illustrating part of a catheter having a double conduit shaft, a balloon, a sleeve and a sleeve supporting member arranged such that the distal end of the sleeve supporting member extends distally beyond the distal end of the sleeve when the sleeve is in the expanded state.

Reference is now made to FIG. 27 which is a schematic cross-section illustrating part of a catheter 280 having a double conduit shaft, a balloon, a sleeve and a sleeve supporting member arranged such that the distal end of the sleeve supporting member extends distally beyond the distal end of the sleeve when the sleeve is in the expanded state in accordance with another embodiment of the catheters of the present application.

The catheter 280 is similar in construction and operation to the catheter 260 of FIG. 15, except that the sleeve supporting member 89 is longer than the sleeve supporting member 69 of the catheter 260. Therefore, in the catheter 270, the distal end 89B of the sleeve supporting member 89 extends distally beyond the distal end 8B of the sleeve 8 when the sleeve 8 is in the expanded state. It is noted that the catheter 280 (only the distal part thereof is illustrated in FIG. 27) may be configured as a OVT catheter (similar to the configuration of the OVT catheters 2 and 100) or as a rapid exchange catheter (similar to the configuration of the RE catheter 202).

Thus, in the sleeved catheters having sleeve supporting members, when the balloon is in the inflated state or when the balloon is in the deflated state (after the balloon is inflated and then deflated to form the cavity), the distal end of the open sleeve may either extend distally beyond the distal end of the sleeve supporting member or may extend distally to the same distance of the distal end of the sleeve supporting member along the longitudinal dimension of the catheter, or alternatively, the distal end of the sleeve supporting member may extend distally beyond the distal end of the sleeve along the longitudinal dimension of the catheter. Practically, the length (longitudinal dimension) of the sleeve and/or the sleeve supporting member of the catheter may be selected such that a desired one of the above alternative configurations is easily achieved. Alternatively, the sleeve supporting member may be disposed relative to the sleeve to such that a desired one of the above alternative configurations of the positions of the distal ends of the sleeve and of the distal end of the sleeve supporting member is easily achieved. Additionally and/or alternatively, both the longitudinal dimensions (length) of the sleeve and/or the sleeve supporting member and the position of the placement of the sleeve supporting member relative to the sleeve may be selected to achieve any of the above described configurations. Thus, the catheters of the present invention may be constructed by using any and all suitable combinations of different dimensions and/or positioning and/or placement of the sleeve supporting member relative to the sleeve.

It is noted that all the catheters disclosed in the present application may be used not only for dilating or opening up a constriction a body cavity or a blood vessel (such as, for example in an angioplasty medical procedure) but may also be effectively used to deploy a stent within the body cavity (such as, but not limited to, an arterial stent, a coronary stent, or any other type of stent known in the art).

Figure 28:
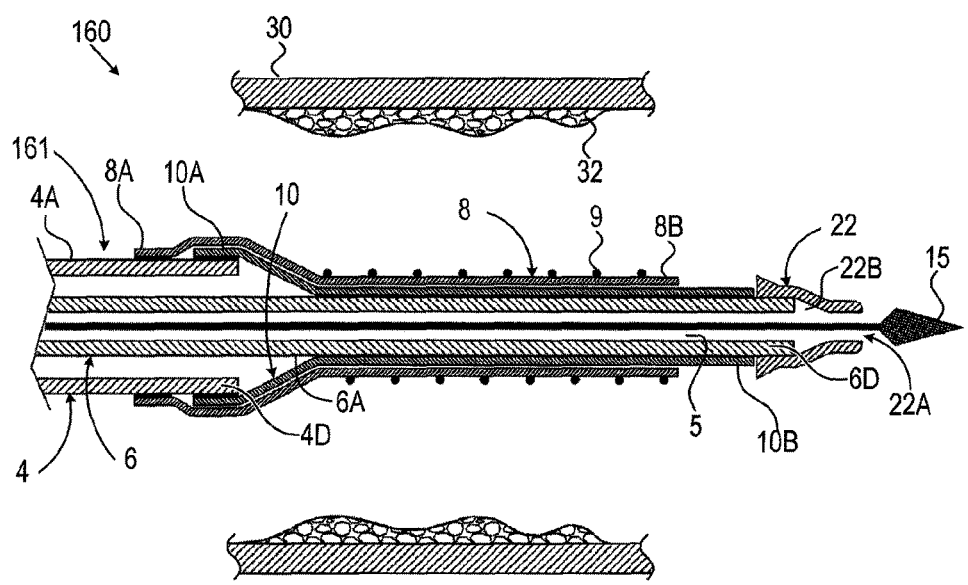
FIGS. 28-30 are schematic cross-sectional diagrams of part of a catheter including a balloon, a sleeve and a deployable stent, illustrated at three different steps of operating the catheter, in accordance with yet another embodiment of the catheter of the present application.
Figure 29:
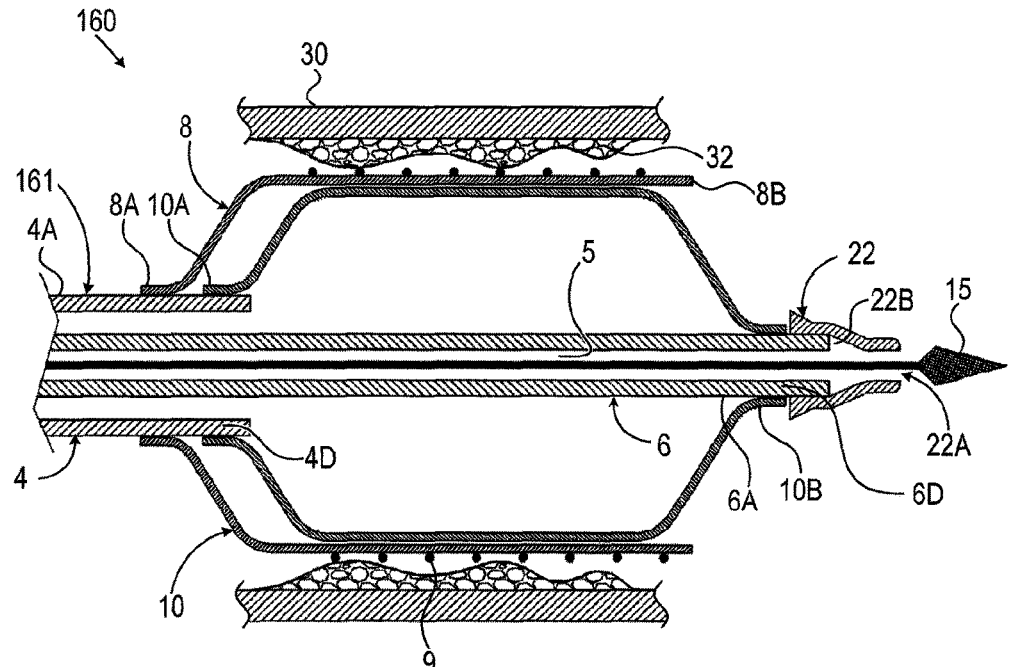
Figure 30:
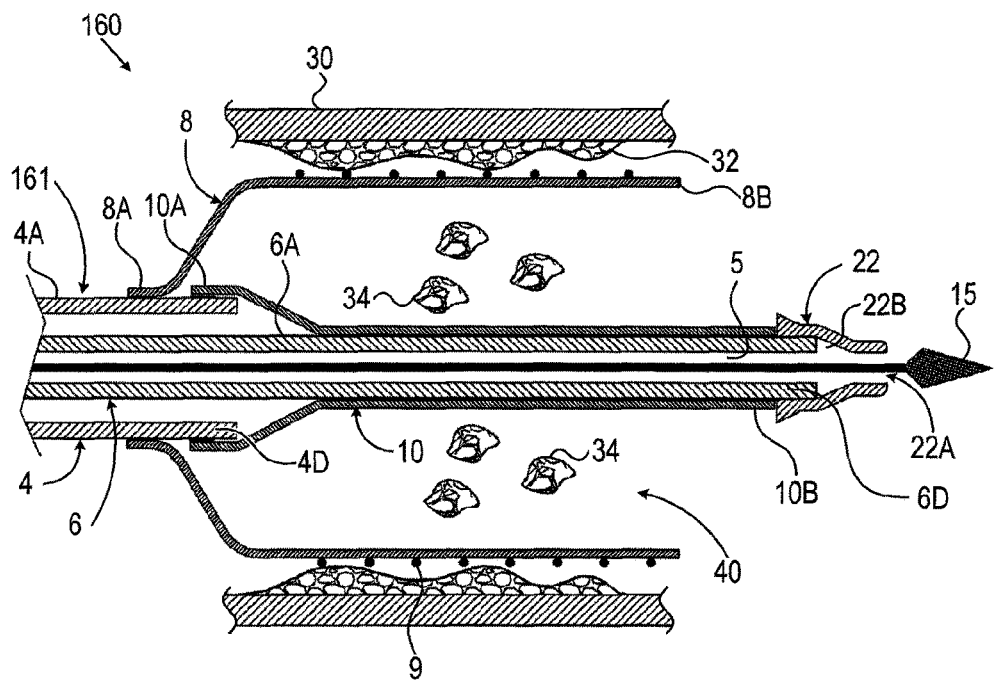

Reference is now made to FIGS. 28-30 which are schematic cross-sectional diagrams of part of a catheter including a shaft, a balloon and a sleeve attached to the shaft and a deployable stent, illustrated at three different steps of operating the catheter, in accordance with another embodiment of the catheters of the present application.

The catheter 160 of FIGS. 28-30 is similar in construction and operation to the catheter 2 of FIGS. 5-7, except that the catheter 160 also includes a deployable stent 9 which is disposed on the sleeve 8 and surrounds the sleeve 8. FIG. 28 illustrates the state of the catheter 160 before the balloon 10 is inflated. In this state, the stent 9 is in the non-expanded state and the catheter including the stent 9 has a small crossing profile (as illustrated in FIG. 28).

FIG. 29 illustrates the state of the catheter 160 after the balloon 10 is positioned in the blood vessel 30 at the region to be treated and the balloon 10 has been inflated using inflation fluid at the nominal inflation pressure. As the balloon 10 expands, it expands the sleeve 8 (or unfolds, or opens the sleeve 8, depending on the type of folding and arrangement of the sleeve 8 and the balloon 10, as disclosed hereinabove with respect to FIGS. 2 and 4). The expanding sleeve 8 exerts a force on the stent 9 which expands and opens the stent 9 such that the stent 9 or parts thereof come in contact with at least part of the treated (opened or dilated) region of the lesion (such as a constricted blood vessel lumen or obstruction due to plaque, and the like) as is know in the art of stent deployment.

As illustrated in FIG. 30, after expansion of the stent 9, the balloon 10 is deflated to form the cavity 40 and to capture and retain debris 34 formed during the treatment as disclosed in detail hereinabove (with respect to the catheters 2 and 100 and FIGS. 1-7). FIG. 30 illustrates the state of the catheter with the sleeve 8 and the stent 9 both in the fully expanded state and with the balloon 10 in the deflated state. Some debris 34 resulting from the treatment of the blood vessel and the deployment of the stent 9 has been sucked into and retained within the cavity 40.

It is noted that the shaft 171 of the catheter 170 (only the distal part thereof is illustrated in FIGS. 28-30) may be configured as a OVT catheter shaft (similar to the configuration of the OVT catheter shafts 1 and 101) or as a rapid exchange catheter shaft (similar to the configuration of the catheter shaft 201 of the RE catheter 202).

It is further noted, that FIGS. 28-30 illustrate a medical device 15, disposed within the lumen 5 of the inner conduit 6. Such a medical device may be any type of therapeutic device or diagnostic device known in the art, such as but not limited to, a surgical instrument, a surgical blade, a rotablator, an optical fiber (or optical fiber bundle) optically coupled to a laser, a tissue ablating device, a diagnostic optical fiber (or optical fiber bundle) optically coupled to a slight source and/or a diagnostic spectrometer, an intravascular ultrasound (IVUS) device, an ultrasonic probe, a sensor for receiving diagnostic signals, a temperature sensor, a chemical sensor, a pH sensor, or any other therapeutic devices and/or diagnostic devices known in the art.

Any such therapeutic or diagnostic or imaging devices may be inserted into the catheter shaft 1 through the same hollow passage of the lumen 5 of the catheter 2 or through any other hollow passage usable for inserting a guide wire into the catheter shaft, by withdrawing the guide wire (such as the guide wire 14) which was used to guide the catheter during insertion and moving of the catheter within the vasculature and inserting the desired device (such as the medical device 15) into the same hollow passage. For example, if the catheter 160 was inserted into the blood vessel 30 using a guide wire 14 (not shown in FIGS. 28-30), the guide wire 14 may be then withdrawn from the lumen 5 and a rotablator may be inserted through the lumen 5 to reach an obstruction at the treated region. The rotablator may then be used to open the obstruction in the treated region as is known in the art and then withdrawn. Some of the debris 34 released by the action of the rotablator may then be captured by inflating and then deflating of the balloon 10 to form of the cavity 40 and the associated suction as disclosed in detail hereinabove. If desired, the guide wire 145 may be reinserted into the lumen 5 after withdrawal of the medical device 15 (such as the exemplary rotablator) from the lumen and the catheter 160 together with any captured debris 34 may be withdrawn from the vasculature as disclosed hereinabove. After the withdrawal of the catheter 160 from the vasculature, the stent 9 remains deployed within the treated site.

It will be appreciated by those skilled in the art that the catheters of the present application are not limited to using only balloons having a cylindrical cross sectional shape with tapering or conical proximal and distal balloon ends. Rather, any type of suitable balloon having any suitable shape, size and cross-sectional profile (either a longitudinal cross-sectional profile and/or a radial cross sectional profile) may be used in implementing any of the catheters disclosed herein. Some non-limiting examples of balloon shapes useable in the catheters disclosed in the present application may include cylindrical balloons having conical or tapering ends, stepped balloons having two or more cylindrical portions having different diameters of at least some of the cylindrical portions, balloons having a conical or tapering longitudinal cross-sectional shape, balloons having at least one corrugated portion, balloons having a uniform wall thickness, balloons having a non-uniform wall thickness Other types of balloons which may be used in the catheters of the present application may also include compliant balloons made of latex or other flexible elastic materials which typically do not have a nominal inflated diameter due to their flexibility. Such balloons may be used together with sleeves made of either non-stretchable non-compliant material(s) or with sleeves made from a stretchable material(s) which are semi-compliant, provided that the sleeve in the open state (either unfolded or stretched, respectively) has sufficient mechanical strength and/or resistance to further expanding beyond a certain predetermined diameter to confine the compliant balloon within the nominal diameter of the fully open and/or fully unfolded and/or fully stretched sleeve. When using such highly flexible balloons (such as, for example, latex balloons), the sleeves mat be constructed and have dimensions and compositions which are suitable for achieving a desired radial dimension needed for the therapeutic procedure and are configured not to exceed the nominal sleeve diameter within practical manufacturing tolerances acceptable for medical use.

Figure 31:
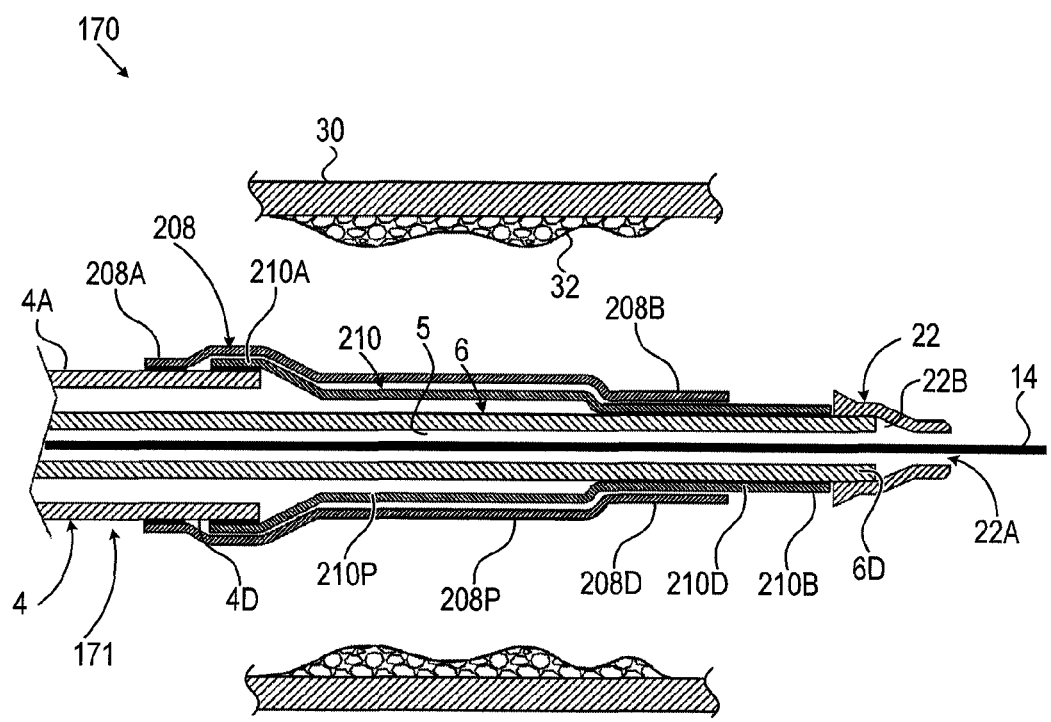
FIGS. 31-33 are schematic cross-sectional diagrams of part of a double conduit catheter having a stepped balloon and a sleeve, illustrated at three different stages of operating the catheter, in accordance with another embodiment of the catheter of the present application.
Figure 32:
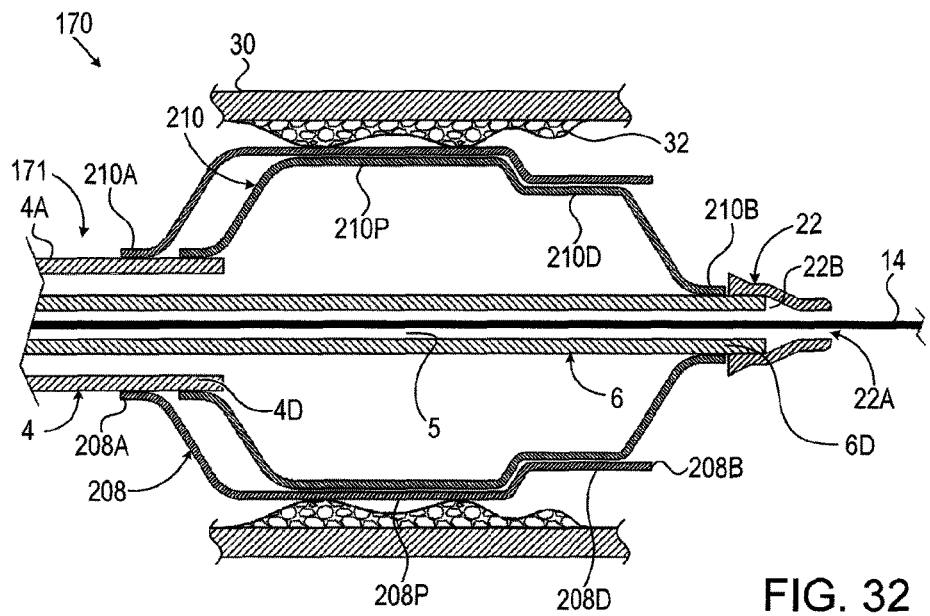
Figure 33:
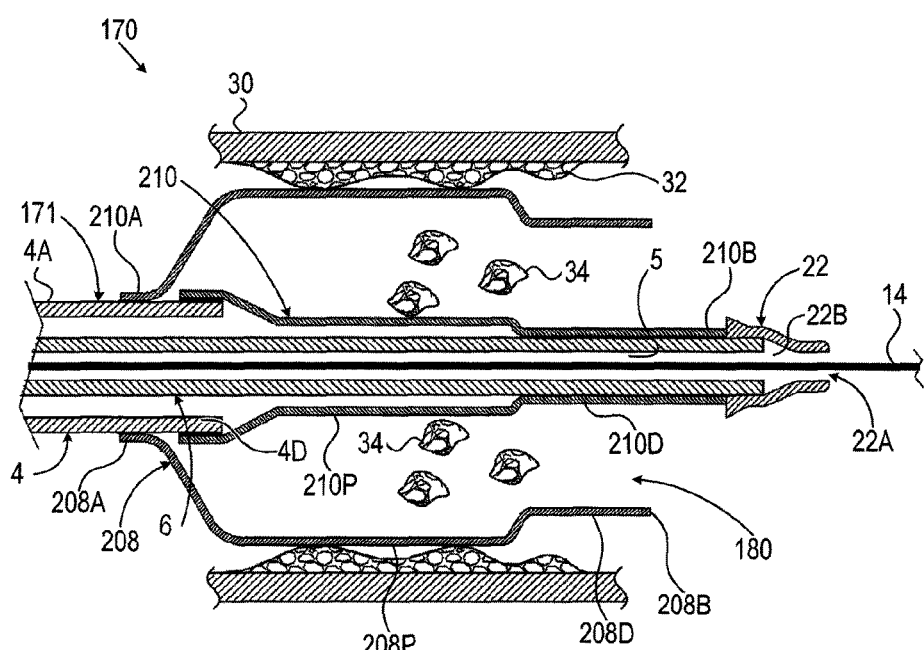

Reference is now made to FIGS. 31-33, which are schematic cross-sectional diagrams of part of a double conduit catheter 170 having a shaft, a stepped balloon and a sleeve attached to the shaft, illustrating three different stages of operating the catheter, in accordance with another embodiment of the catheters of the present application.

The catheter 170 is similar in structure to the catheter 2 of FIG. 1, except that instead of the balloon 10 and the sleeve 8, the catheter 170 includes a balloon 210 and a sleeve 208 which are different than the balloon 10 and the sleeve 8 of the catheter 2. The inner conduit 6, the outer conduit 4 and the (optional) soft tip 22 included in the catheter 170 are as described in detail hereinabove for the catheter 2 (of FIG. 1). The balloon 210 is a stepped balloon having a cylindrical proximal balloon part 210P and a cylindrical distal balloon part 210D. The diameter of the cylindrical proximal balloon part 210P is larger than the diameter of the distal cylindrical balloon part 210D. The distal end 210B of the balloon 210 is sealingly attached to the surface of the distal end 6D of the inner conduit 6 and the proximal end 210A of the balloon 210 is sealingly attached to the outer surface 4A of the distal end 4D of the outer conduit 4 as disclosed hereinabove in detail with respect to the balloon 10 of the catheter 2.

The sleeve 208 is a stepped sleeve having a cylindrical proximal sleeve part 210P and a cylindrical distal sleeve part 208D. The diameter of the cylindrical proximal sleeve part 208P is larger than the diameter of the distal cylindrical sleeve part 208D. The distal end 210B of the sleeve 208 is an open end. The proximal end 208A of the sleeve 208 is sealingly attached to the outer surface 4A of the distal end 4D of the outer conduit 4 as disclosed hereinabove in detail with respect to the sleeve 8 of the catheter 2.

FIG. 31 illustrates a state of the catheter in which the balloon 210 is deflated and the sleeve 208 is in a non opened state. In this state, the balloon 210 may be folded or wrapped around the inner conduit 6 while the sleeve 208 is in a non-expanded (non-stretched) state and has a circular cross section (in a way similar to the way illustrated in FIG. 2 in). Alternatively, the balloon 210 may be folded around the inner conduit 6 and the sleeve 208 may be folded over the balloon 210 as is illustrated in FIG. 4.

FIG. 32 illustrates the state of the catheter 170 after the balloon 210 has been inflated by a suitable inflation fluid at the nominal inflation pressure of the balloon 210. During the inflation of the balloon 210, the balloon unfolds and expands to exert on outward force which radially expands the sleeve 208. If the sleeve 208 is made from a stretchable, semi-compliant or compliant material, the distal part 210D of the balloon 210 expands the distal part 208D of the sleeve 208 such that when the balloon is fully expanded at the nominal inflation pressure, the diameter of the expanded (stretched) proximal part 208P of the sleeve 208 is larger than the diameter of the expanded distal part 208D of the sleeve 208 as is illustrated in FIG. 32.

If the sleeve 208 is made from a non-stretchable, non-compliant material and is folded over the balloon 210 in a way similar to the folding shown in FIG. 4, the distal part 210D and the proximal part 210P of the balloon 210 expand and pushes the sleeve 208 such that the sleeve 208 unfolds and opens to its fully opened state as is illustrated in FIG. 32 when the sleeve 208 is fully opened (fully unfolded), the diameter of the fully opened proximal part 208P of the sleeve 208 is larger than the diameter of the fully opened (fully unfolded) distal part 208D of the sleeve 208 as is illustrated in FIG. 32.

If the balloon 210 is made from a semi-compliant material and the sleeve 208 is made from semi-compliant stretchable material and is folded over the balloon 210 in a way similar to the folding shown in FIG. 4, the distal part 210D and the proximal part 210P of the balloon 210 expand and also stretches and pushes the sleeve 208 such that the sleeve 208 unfolds and opens to its fully opened state as is illustrated in FIG. 32. However, since in this type of arrangement (semi-compliant balloon 210 with semi-compliant stretchable sleeve 208) the balloon 210 also stretches, the sleeve 208 first unfolds and then stretches to accommodate the additional increase in the diameter (and circumference) of the balloon 210 resulting from the stretching of the balloon 210. In this arrangement when the sleeve 208 is fully opened (fully unfolded and somewhat stretched), the diameter of the fully opened proximal part 208P of the sleeve 208 is larger than the diameter of the fully opened (fully unfolded) distal part 208D of the sleeve 208 as is illustrated in FIG. 32.

Thus, in any of the catheters of the present application any of the following combinations are usable:

a) A stretchable (semi-compliant or compliant) sleeve with a non-compliant, non-stretchable balloon.

b) A stretchable (semi-compliant or compliant) sleeve with a semi-compliant, stretchable balloon.

c) A non-stretchable (non-compliant) sleeve with a semi-compliant, stretchable balloon.

d) A non-stretchable (non-compliant) sleeve with a highly-compliant balloon.

e) A stretchable (semi-compliant) sleeve with a highly-compliant balloon (such as, for example a Latex® balloon).

In such combinations a-e, the balloon and/or the sleeve may be folded or not folded, as required by the application and by the circumference of the balloon and/or the sleeve when they are in the non-inflated state or in the non opened and/or non-unfolded state, respectively.

FIG. 33 illustrates the catheter 170 in the state after the balloon 210 has been inflated to expand (and/or stretch and/or open and/or unfold) the sleeve 208 (depending on which one of the above described balloon and sleeve combinations a-e is being used in the catheter) and then deflated. During (and after) the deflation of the inflated balloon 210, a cavity 180 is formed between the opened sleeve 208 and the deflated balloon 210 and the resulting suction during the formation of the cavity 180 withdraws fluid (such as, for example, blood within a treated blood vessel or any other fluid present in a bodily cavity being treated) and causes some of the debris 34 present in the fluid to be captured and retained in the cavity 180 as is explained in detail hereinabove with respect to the cavity 40 of the catheter 2. After the capturing of the debris 34, the catheter 170 together with the captured debris may be withdrawn and removed from the body as disclosed hereinabove.

It is noted that the smaller diameter of the distal part 208D of the sleeve 208 may be advantageous because it may assist the retaining of the debris 34 within the cavity 180 during withdrawal of the catheter 170 from the body. However, it will be appreciated that such a narrower diameter of the distal part 208D of the sleeve 208 (as compared to the diameter of the proximal part 208P of the sleeve 208) is not obligatory to the operation of the catheter 170 and that the sleeve 208 of the catheter 170 may also be substituted with other suitable types of sleeves (such as, for example, the sleeves 8, 28, 38 and 80) resulting in a catheter having a stepped balloon 210 with a non-stepped sleeve or a non-stepped perforated sleeve 80. Alternatively, the sleeve 208 may be also be a stepped and perforated sleeve (not shown in FIGS. 31-33) and the catheter may also include the substance 90 to be applied to the treated region as disclosed hereinabove in detail with respect to the catheters 230 and 250.

It is noted that the shaft 171 of the catheter 170 (only the distal part thereof is illustrated in FIGS. 31-33) may be configured as a OVT catheter shaft (similar to the configuration of the OVT catheter shafts 1 and 101) or as a rapid exchange catheter shaft (similar to the configuration of the catheter shaft 201 of the RE catheter 202).

Figure 34:
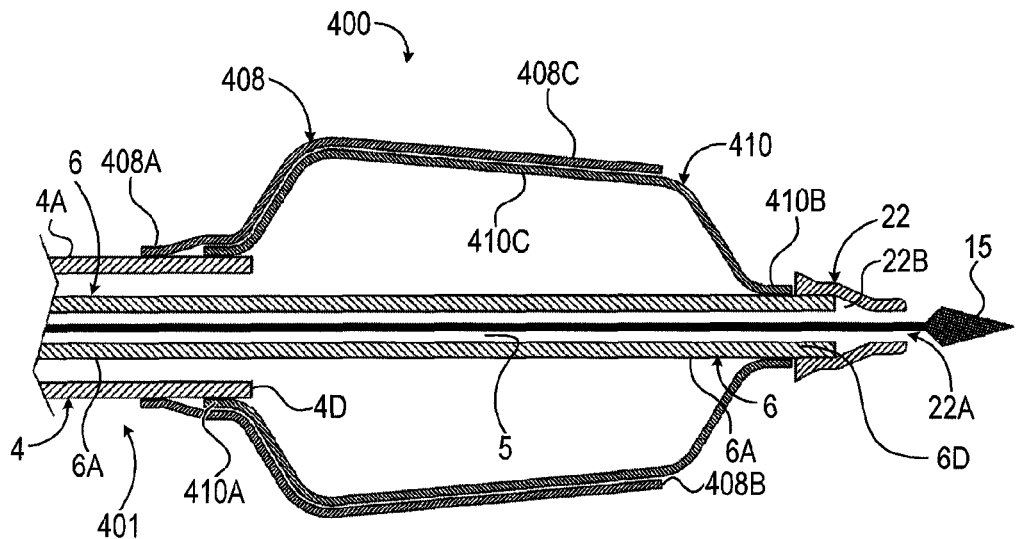
FIGS. 34-35 are schematic cross-sectional diagrams of part of a double conduit catheter having a conically tapering balloon and a sleeve, illustrated at two different stages of operating the catheter, in accordance with yet another embodiment of the catheter of the present application.
Figure 35:
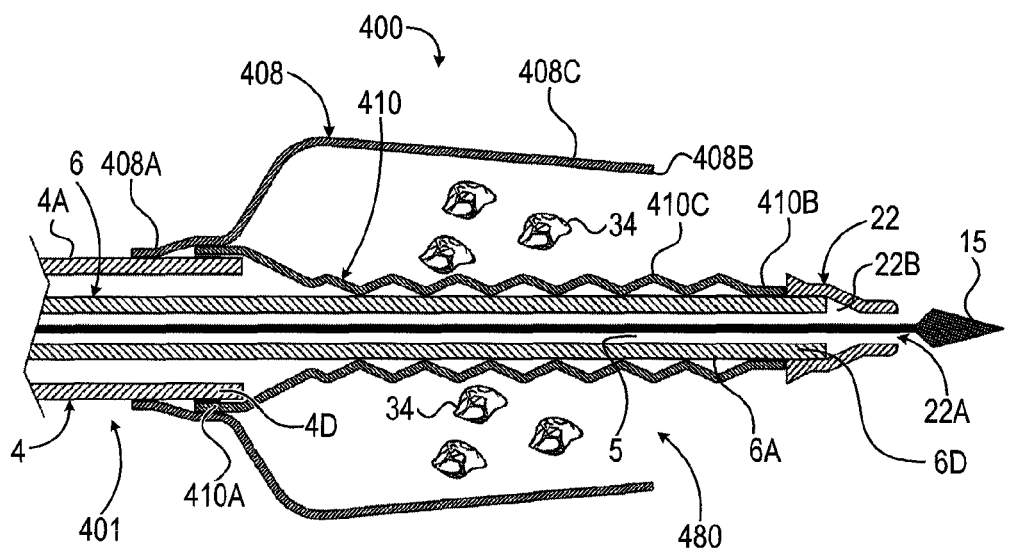

Reference is now made to FIGS. 34-35, which are schematic cross-sectional diagrams of part of a double conduit catheter 400 having a conically or tapering balloon and a sleeve, illustrating two different stages of operating the catheter, in accordance with another embodiment of the catheters of the present application.

The catheter 400 includes a shaft 401 a conical balloon 410 a sleeve 408 and a soft tip 22. The shaft 401 includes an inner conduit 6 and an outer conduit 4 as disclosed in detail for the catheter 2 of FIG. 1. The balloon 410 has a truncated conical portion 410C, a distal end 410B and a proximal end 410A. The sleeve 408 has a proximal end 408A distal end 408B.

The distal end 410B of the balloon 410 is sealingly attached to the outer surface 6A of the distal end 6D of the inner conduit 6 and the proximal end 410A of the balloon 410 is sealingly attached to the outer surface 4A of the distal end 4D of the outer conduit 4 as disclosed in detail hereinabove. The proximal end 408A of the sleeve 408 is sealingly attached to the outer surface 4A of the distal end 4D of the outer conduit 4.

In a closed state (not shown in FIGS. 34-35) of the catheter 400, the deflated balloon 410 may be arranged in a folded (wrapped) arrangement over the outer surface 6A of the inner conduit 6 (as disclosed with respect to the balloon 10 in FIG. 2) and the sleeve 408 may be arranged over the folded balloon as is disclosed in detail in FIG. 2. Alternatively, both the balloon 410 and the sleeve 408 may be folded such that the balloon 410 is folded (wrapped) over the inner conduit 6 and the sleeve 408 is folded (wrapped) over the balloon 410, in a way similar to the folding illustrated in FIG. 4.

When the balloon 410 is inflated (with the nominal inflation pressure), the balloon 410 unfolds and expands exerting a force on the sleeve 408 which may open and/or unfold and/or expand and/or stretch the sleeve 408 (depending on which type of the combinations a-e of balloon and sleeve type is implemented in the catheter 400, as disclosed in detail hereinabove with respect to the catheter 170 and other catheters).

FIG. 35 illustrates the state of part of the catheter 400 after the balloon 410 has been inflated using the nominal inflation pressure of the balloon 410. In this state the sleeve 408 has a portion 408C having a truncated conical shape which may be preformed in the sleeve before the balloon is expanded (in an embodiment in which the sleeve is a non-compliant sleeve or a semi-compliant sleeve). Alternatively, the truncated conical portion 408C may be formed as a result of the stretching of the sleeve 408 (in an embodiment in which the sleeve 408 is a stretchable sleeve made from a semi-compliant or highly compliant material).

FIG. 36 illustrates the catheter 400 in the state after the balloon 410 has been inflated to expand (and/or stretch and/or open and/or unfold) the sleeve 408 (depending on which one of the above described balloon and sleeve combinations a-e is being used in the catheter) and then deflated. During (and after) the deflation of the inflated balloon 410, a cavity 480 is formed between the opened sleeve 408 and the deflated balloon 410 and the resulting suction during the formation of the cavity 480 withdraws fluid (such as, for example, blood within a treated blood vessel or any other fluid present in a bodily cavity being treated) and causes some of the debris 34 present in the fluid to be captured and retained in the cavity 480 as is explained in detail hereinabove with respect to the cavity 40 of the catheter 2. After the capturing of the debris 34, the catheter 400 together with the captured debris 34 may be withdrawn and removed from the body as disclosed hereinabove.

It is noted that the smaller diameter of the distal part 408B of the sleeve 408 may be advantageous because it may assist the retaining of the debris 34 within the cavity 480 during withdrawal of the catheter 400 from the body. A further advantage of the conical (or tapering) shape of the balloon 410 (such as, for example, the truncated conical portion 410C illustrated in FIGS. 34-35) is that it may facilitate the insertion of the catheter 410 into large peripheral veins which may often have a substantially conical longitudinal cross section. This advantage may be especially pertinent when treating an extended lesion or several lesions in a long portion of such a peripheral artery or peripheral vein where the conical shaping of the balloon or part of the balloon may more efficiently dilate the artery or vein or the cavity and treat the lesion(s) due to a better match of the geometry of the balloon 410 to the longitudinal conical-like cross-sectional shape of the treated vessel or vein or cavity. Examples of blood vessels which may benefit from treatment with catheters of the present application having conically shaped balloons and/or tapering or balloons with non-linearly varying longitudinal cross-sectional shapes and/or conically shaped sleeves and/or tapering sleeves and/or sleeves with non-linearly varying longitudinal cross-sectional shapes may include the femoral artery, the femoral vein, the iliac artery, the iliac vein, the renal artery, the renal vein, the carotid artery, the left main coronary artery, the cardiac sinus vein and other arteries and veins having a varying cross sectional longitudinal profile.

Additionally, balloons and sleeves having conical portions or tapering portions or portions having a non-linearly varying longitudinal cross-sectional profiles may be advantageously used to deploy stents having a varying longitudinal cross-sectional profiles, such as, for example the Sinus-Carotid-Conical-RX stents, commercially available from OptiMed Medizinische Instrumente GmbH, of Ettlingen, Germany.

Alternatively, the sleeve 408 may be also be perforated sleeve (not shown in FIGS. 34-35) and the catheter may also include the substance 90 to be applied to the treated region as disclosed hereinabove in detail with respect to the catheters 230 and 250.

It is noted that the shaft 401 of the catheter 400 (only the distal part thereof is illustrated in FIGS. 34-35) may be configured as an OVT catheter shaft (similar to the configuration of the OVT catheter shafts 1 and 101) or as a rapid exchange catheter shaft (similar to the configuration of the catheter shaft 201 of the RE catheter 202).

It will be appreciated that the methods of attachment of the balloons and sleeves to the shafts of the catheters of the present application is not obligatorily limited to the methods disclose hereinabove. For example, the catheter 500 of FIG. 36 below discloses an alternative arrangement for the attachment of the sleeve and the balloon to the shaft of the catheter.

Reference is now made to FIG. 36, which is a schematic cross-sectional diagram illustrating part of a catheter having a shaft, a balloon, a sleeve and an expandable or spring-like coil wound over the balloon and under the sleeve, in which the sleeve is attached to the balloon and the balloon is sealingly attached to the shaft of the catheter, in accordance with yet another embodiment of the catheters of the present application.

The catheter 500 (only part thereof is shown in FIG. 36) includes a catheter shaft 501, a balloon 510, a sleeve 508, a sleeve retaining member 69 and a soft tip 22. The shaft 501 includes an inner conduit 6 disposed within an outer conduit 4 (as disclosed hereinabove and illustrated in FIG. 1). The balloon 510 has a proximal end 510A sealingly attached to the surface 4A of the distal end 4D of the outer conduit 4 using any of the attachment methods described hereinabove. However, in contrast to the catheter 2 (of FIG. 1) in which the region of attachment of the proximal end of the sleeve 8 to the surface 4A of the outer conduit 4 is positioned proximal to the region of attachment of the proximal end 10A of the balloon 10 to the surface 4A of the conduit 4, In the catheter 500, the proximal end 508A of the sleeve 508 is sealingly attached (by gluing thermal welding, ultrasonic welding, and the like) to the distal end 410A of the balloon 410 as best seen in FIG. 36. Apart from the different attachment configuration of the proximal end of the sleeve 508, the operation of the catheter 500 is similar to the operation of the catheter 260 of FIGS. 14-15 as disclosed in detail hereinabove.

It is noted that the shaft 501 of the catheter 500 (only the distal part thereof is illustrated in FIG. 36) may be configured as a OVT catheter shaft (similar to the configuration of the OVT catheter shafts 1 and 101) or as a rapid exchange catheter shaft (similar to the configuration of the catheter shaft 201 of the RE catheter 202).

Figure 37:
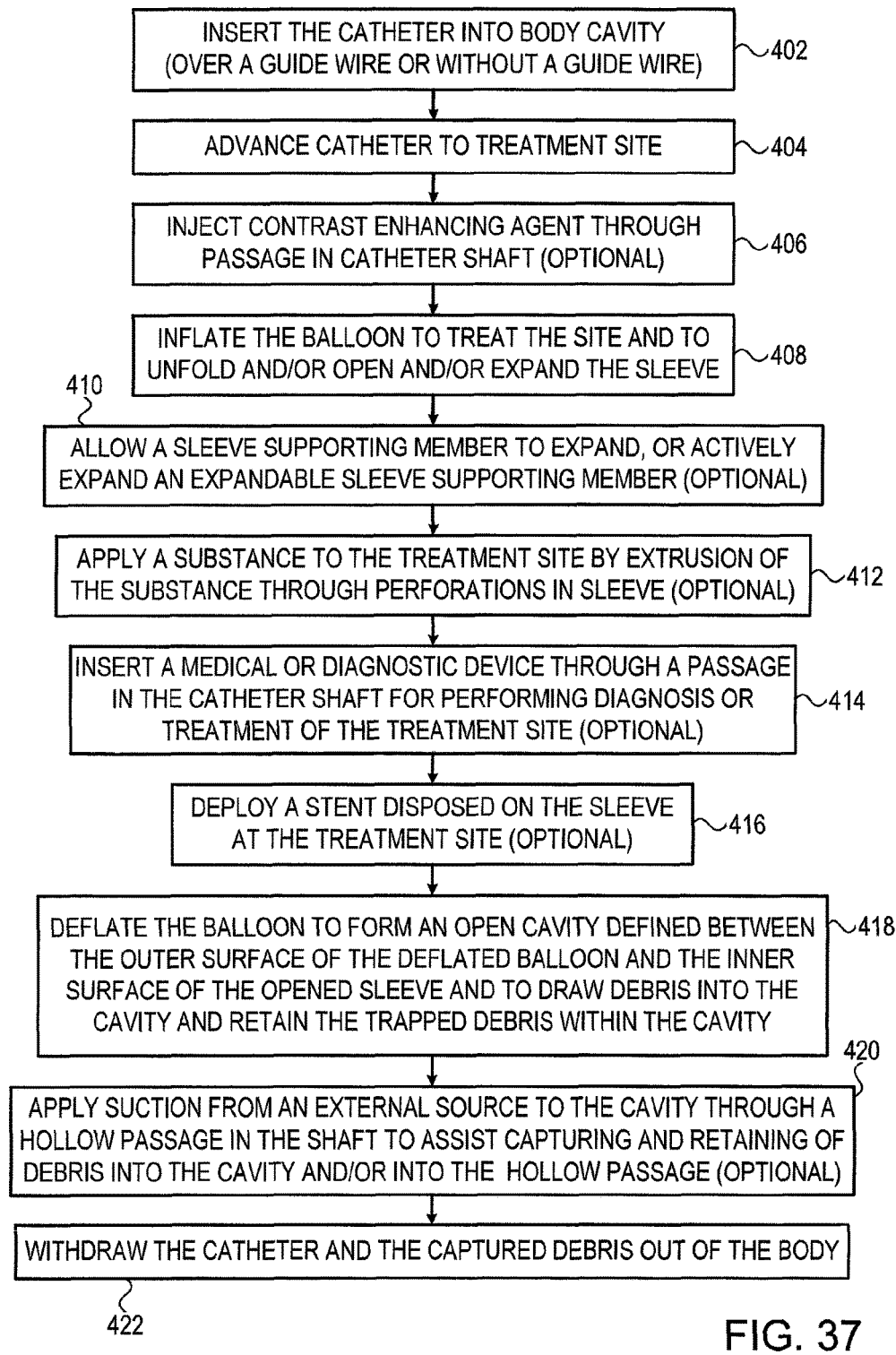
FIG. 37 is a schematic block diagram illustrating steps of an additional method for using the catheters of the present application in a medical procedure.

Reference is now made to FIG. 37 which is a schematic block diagram illustrating the steps of a method for using the catheters of the present application in a medical procedure, in accordance with yet another embodiment of the methods of using the catheters of the present application.

The method includes inserting the catheter (such as any of catheters disclosed herein) into a body cavity either over a guide wire or without using a guide wire (step 402). The method also includes advancing the catheter within the cavity to reach the treatment site (step 404), optionally injecting a contrast enhancing agent (or fluid) through a passage in the catheter shaft (step 406). The method also includes inflating the balloon to treat the site and to unfold and/or open and/or expand catheter the sleeve. In this step the sleeve may be stretched if it is a stretchable sleeve (step 408). The method also includes (optionally) allowing a sleeve supporting member to expand or allowing a sleeve supporting member to actively expand (step 410). It is noted that in step 410, if the (optional) sleeve supporting member is a passively expandable member, it is expanded by the expanding balloon. However, if the sleeve supporting member is an actively expanding sleeve supporting member (such as, for example, a compressed helical coil or a compressed sleeve supporting member which is capable of expanding because of its compressed state, the opening of the sleeve supporting member is assisted by the expansion of the balloon and the expansion or unfolding or opening of the sleeve by the balloon which allows active expansion of the sleeve supporting member to its non-compressed form.

The method may (optionally) also include the applying of a substance (such as the substance 90) to the treatment site by extrusion of the substance through perforations (such as the perforations 80C of the sleeve 80) in the sleeve (step 412). It is noted that the substance 90 may comprise any of the ingredients or components or any combination of ingredients or components as disclosed in detail hereinabove with respect to the catheter 250 (of FIGS. 11-12).

The method also includes the (optional) inserting of a medical device and/or a diagnostic device through a passage in the catheter shaft for performing diagnosis or treatment of the treatment site (step 414). In the optional step 414, any of the medical and/or diagnostic and/or imaging devices described in the present application and/or known in the art may be used. The method may also (optionally) include the deploying of a stent disposed on the sleeve at the treatment site (such as a blood vessel or any other body cavity as disclosed in detail in the present application (step 416), any suitable type of stent known in the art may be used in step 416.

The method also includes deflating the balloon to form an open cavity defined between the outer surface of the deflated balloon and the inner surface of the opened sleeve and drawing debris into the cavity and retaining the trapped debris within the cavity (step 418).

The method may also (optionally) include the applying of suction from an external source to the cavity through a hollow passage in the shaft of the catheter to assist the capturing and retaining of the debris into the cavity and/or into the hollow passage (step 420. It is noted that the (optional) step 420 may be used in catheters in which the cavity is fluidically connected to a passage within the catheter shaft which may be suitably connected to an external suction (or vacuum) source, such as, for example, any of the catheters 52 of FIG. 16 and the catheter 352 of FIG. 19.

The method also includes the withdrawing of the catheter and the captured debris out of the body (step 422). Step 422 may be achieved by pulling the catheter proximally until it exits the body.

It will be appreciated by those skilled in the art that not all the steps disclosed in FIG. 37 are performed in the order that is shown bin FIG. 37. Rather, some of the steps (such as, for example the steps 406, 412, 414, 416, and 420) may be performed (if they are performed at all) in an order which may be different than the order illustrated in FIG. 37.

Furthermore, some of the steps illustrated in FIG. 37 may only be performed by specific types or embodiments of the catheters disclosed herein. For example, step 410 may be performed only by catheter embodiments including a sleeve supporting member (such as, for example, the catheter 260 of FIG. 14, the catheter 270 of FIG. 26, the catheter 280 of FIG. 27 and the catheter 500 of FIG. 36), or by any other catheter embodiments disclosed herein that are modified or adapted by adding an appropriate sleeve supporting member thereto.

It is noted that any of the catheters disclosed in the present application may also include one or more position detection assisting devices attached to one or more parts of the shaft for enabling a three dimensional catheter positioning system to determine the position (in a defined three dimensional coordinate system) of at least part of the catheter in a reference frame defined in three dimensional space, as is well known in the art. The position detection assisting devices may be magnetic or electromagnetic or ultrasonic (such as magnetic and electrical coils or electrical coil combinations or the ultrasonic devices or any other position sensing device or probe or tag (wired or wireless) adapted for inclusion in a catheter or other invasive medical device, as is disclosed in detail in U.S. Pat. Nos. 8,473,032, 8,218,847, 7,998,062, 7,969,143, 7,555,330, 7,233,820, 7,924,000, 7,848,789, 7,816,915, 7,729,742, 7,590,441, 7,397,364, 7,301,332, 6,992,477, 6,690,963, 6,427,314, 6,161,032 and 5,833,608 which are all incorporated herein by reference in their entirety for all purposes.

It is noted that any such sensors, electrically conducting coils, electrically conducting coil assemblies, ultrasonic probes and/or tags, other types of tags (including passive, active, wired and wireless forms of such devices) useful for position sensing may be either attached to or mounted on any of the sleeved catheters disclosed in the present application. Additionally and/or alternatively any of these position detecting devices, sensors, probes and tags described above may be inserted into one of the hollow passages in the shaft of any of the catheters disclosed herein before and/or during the insertion of the catheters into the body, and/or before or during the performing a medical procedure in a body cavity or blood vessel. Furthermore, the methods disclosed in FIGS. 18 and 37 may also (optionally) include a step of inserting a device including such a position detecting or position determination assisting device, sensor, probe or tag into the catheter shaft, preferably (but not obligatorily) through the same hollow passage through which a guide wire may be inserted.

Furthermore, if the position detecting or position determining assisting device is attached to the catheter (permanently or by inserting into the catheter), the method may (optionally) include an additional step of determining the position of the catheter or of a part thereof using a position determining system in conjunction with such a position detecting device, position determining assisting device, probe, sensor and tag. Such position determining systems and methods of their use are well known in the art and are therefore not described in detail hereinafter.

It is noted that in all the catheters disclosed in the application (including but not limited to the catheters 2, 52, 100, 110, 120, 130, 140, 150, 160, 170 202, 230, 250, 260, 270, 280, 352, 400 and 500), none of the components or parts of the shaft of the catheter is movable longitudinally or axially relative to other parts or components of the shaft of the catheter. Because the conduits comprising the shaft of the catheters are not movable relative to each other in the longitudinal (axial) direction, the balloon of the catheters cannot be intussuscepted (as disclosed for the intussuscepting balloons of international published applications WO 2007/004221, WO 2007/042935, WO 2008/004238 and WO 2008/004239).

However, at least some parts of the balloon and/or the sleeve of these catheters may move radially (away and towards the longitudinal axis of the catheter), such as when the balloon is expanded by inflating or contracted by deflating and such as when the sleeve of the catheter is expanded and/or unfolded and/or opened by the balloon of the catheter. Furthermore, in all the catheters disclosed in the application, suction is generated by the step of deflating the balloon of the catheter after the balloon has been inflated to expand and/or unfold and/or open the sleeve and the forming of the cavity defined between the deflated balloon and the expanded and/or opened and/or unfolded sleeve. This suction (generated solely by the deflation of the balloon without any application of externally supplied suction) captures some debris from the body cavity or the vasculature within the open cavity of the catheter.

Further yet, the types and shapes of the balloons usable in the catheters of the present application are not limited to the shapes disclosed herein and illustrated in the drawing figures. Rather, any type of suitable balloon shape and configuration known in the art may be used in the catheters of the present application, including, but not limited to, any of the balloons disclosed in international published applications WO 2007/004221, WO 2007/042935, WO 2008/004238 and WO 2008/004239, WO 2010/001404, WO 2010/001405, WO 2010/079494, WO 2011/080731 and WO 2011/080732 all of which are incorporated herein by reference in their entirety for all purposes.

It is further noted that the sleeves of any of the catheters disclosed in the present application may comprises a material (or a combination of materials) selected from a compliant material, a semi-compliant material, a non-compliant material, a stretchable material, a non-stretchable material, an annealed stretchable material, a pre-stretched non-stretchable material that has undergone molecular orienting by biaxial orienting processes, and any combinations thereof.

It is also noted that in any of the catheters of the present application the sleeve supporting member may be selected from an expandable elastic member, a compressed elastic member, an expandable spring-like member, a compressed spring-like member, a coiled member, a compressed elastic coiled member, a helically coiled member.

Furthermore, it is noted that the structure, materials and dimensions of the catheters disclosed hereinabove and illustrated in the drawing figures may be modified if desired to adapt the catheters for use in different applications performed in the vasculature (including, for example cardiac blood vessels, non-cardiac blood vessels, peripheral veins or any other body arteries or body veins) or in any other type of bodily cavities, including but not limited to a ureter lumen a seminal duct, an ejaculatory duct, a prostate duct, a bile duct, a uterine cavity, a fallopian tube lumen, a cavity within a lung, bronchial cavities, and the like.

What is claimed is:

1. A balloon catheter comprising:
   a catheter shaft;
   an inflatable balloon attached to the catheter shaft; and
   an open sleeve having a proximal end sealingly attached to the catheter shaft and an open distal end, the sleeve surrounds at least part of the balloon,
   wherein the sleeve and the balloon are arranged such that inflating the balloon expands the sleeve into an expanded state and wherein deflating the balloon when the sleeve is in the expanded state forms a single open cavity between the sleeve and the deflated balloon and creates suction to capture and retain debris within the cavity.

2. The catheter according to claim 1, wherein the single cavity is selected from an annular cavity and a non-regular annular cavity.

3. The catheter according to claim 1, wherein the catheter also includes a deployable stent disposed on the sleeve.

4. The catheter according to claim 1, wherein the catheter is an over the wire catheter and wherein the catheter shaft comprises:
   a hollow outer conduit having a distal end, a proximal end and a lumen; and
   a hollow inner conduit, suitable for passage over a guide wire, the inner conduit has a distal part, a proximal part and a lumen, the inner conduit is disposed within the lumen of the outer conduit and positioned such that the distal end of the distal part of the inner conduit extends beyond the distal end of the outer conduit at all times during the operation of the catheter within the body,
   wherein the proximal end of the balloon is sealingly attached to the distal end of the outer conduit and the distal end of the balloon is sealingly attached to the distal end of the inner conduit, wherein the proximal end of the sleeve is sealingly attached to the distal end of the outer conduit of the catheter shaft, and wherein the catheter includes a fluid port fluidically communicating with the lumen of the outer conduit for introducing and withdrawing an inflation fluid into the inflatable balloon and a guide-wire port disposed at the distal end of the catheter, the guide-wire port has an opening suitable for inserting a guide into the lumen of the inner conduit.

5. The catheter according to claim 1, wherein the catheter is a rapid exchange catheter and wherein the catheter shaft comprises:
   a hollow outer conduit having a distal end, a proximal end and a lumen; and
   a hollow inner conduit, suitable for passage over a guide wire, the inner conduit has an angled proximal part that is fixedly attached to the wall of the outer conduit and sealingly pierces the wall of the outer conduit to form an opening in the outer conduit for inserting a guide-wire therethrough, the inner conduit has a straight distal part and a lumen, the inner conduit is disposed within the lumen of the outer conduit and positioned such that the distal end of the distal part of the inner conduit extends beyond the distal end of the outer conduit,
   wherein the inflatable balloon has a proximal end and a distal end, the proximal end of the balloon is sealingly attached to the distal end of the outer conduit and the distal end of the balloon is sealingly attached to the distal end of the inner conduit, wherein the proximal end of the sleeve is sealingly attached to the distal end of the outer conduit, and wherein the catheter includes a fluid port in fluidic communication with the lumen of the outer conduit for introducing and withdrawing an inflation fluid into the inflatable balloon.

6. The catheter according to claim 1, wherein the catheter shaft comprises at least three fluidically separate hollow passages therein, the at least three hollow passages include,
   a first hollow passage for inserting a guide wire therethrough;
   a second hollow passage for inserting inflation fluid into the balloon and for withdrawing inflation fluid from the balloon; and
   a third hollow passage fluidically connected to the single cavity between the balloon and the sleeve, such that suction from an external suction source may be applied to the cavity through the third hollow passage to assist the capturing and retaining of the debris within the cavity or within the third hollow passage.

7. The catheter according to claim 6 wherein the catheter shaft comprises a first conduit, a second conduit and a third conduit, the first conduit is disposed within the second conduit such that the distal end of the third conduit extends distally beyond the distal end of the second conduit, the first hollow passage is the lumen of the first conduit, wherein the second conduit is disposed within the lumen of the third conduit such that the annular space defined between the outer side of the second conduit and the inner side of the third conduit is the third hollow passage, wherein the proximal end of the sleeve is sealingly attached to the third conduit, the proximal end of the balloon is sealingly attached to the distal end of the second conduit and the distal end of the balloon is sealingly attached to the distal end of the first conduit that protrudes beyond the distal end of the second conduit.

8. The catheter according to claim 7 wherein the proximal end of the catheter includes a fluid port fluidically communicating with the third passage for applying suction to the third passage and for injecting a contrast enhancing fluid therethrough into the body cavity, an inflation port fluidically communicating with the second passage for inflating and deflating the balloon and a guide wire port for inserting a guide wire into the first hollow passage.

9. The catheter according to claim 6, wherein the catheter shaft comprises an inner conduit, an intermediate conduit and an outer conduit, the inner conduit is disposed within the intermediate conduit and the intermediate conduit is disposed within the outer conduit such that the distal end of the inner conduit extends distally beyond the distal end of the intermediate conduit, the inner conduit has a straight distal part that protrudes distally beyond the distal end of the intermediate conduit and an angled proximal part that sealingly pierces through the wall of the intermediate conduit and sealingly pierces through the wall of the outer conduit to form an opening in the outer conduit for inserting a guide-wire therethrough, wherein the first hollow passage is the lumen of the inner conduit, the second hollow passage comprises the space between the inner conduit and the intermediate conduit, wherein the intermediate conduit is disposed within the lumen of the outer conduit such that the space defined between the intermediate conduit and the outer conduit comprises the third hollow passage, wherein the proximal end of the sleeve is sealingly attached to the distal end of the outer conduit, the proximal end of the balloon is sealingly attached to the distal end of the intermediate conduit and the distal end of the balloon is sealingly attached to the distal end of the inner conduit that protrudes beyond the distal end of the intermediate conduit.

10. The catheter according to claim 9, wherein the proximal end of catheter includes a fluid port fluidically communicating with the third passage for applying suction to the third passage and for injecting a contrast enhancing fluid therethrough into the body cavity and an inflation port fluidically communicating with the second passage for inflating and deflating the balloon, and wherein the opening in the wall of the outer conduit accessing the lumen of the inner conduit is disposed between the proximal end and the distal end of the wall of the outer conduit.

11. The catheter according to claim 1, wherein the sleeve is selected from the group consisting of,
a sleeve having a distal end that extends distally beyond the distal end of the balloon when the balloon is in the deflated state,
a sleeve having a distal end that extends distally along the catheter shaft to the same longitudinal position of the distal end of the balloon when the balloon is in the deflated state, and
a sleeve having a distal end such that the distal end of the balloon extends distally beyond the distal end of the sleeve when the balloon is in the deflated state.

12. The catheter according to claim 1, wherein the sleeve is selected from the group consisting of,
a sleeve having a distal end that extends distally beyond the distal end of the balloon when the balloon is in the inflated state,
a sleeve having a distal end that extends distally to the same longitudinal position of the distal end of the balloon when the balloon is in the inflated state, and
a sleeve having a distal end such that the distal end of the balloon extends distally beyond the distal end of the sleeve when the balloon is in the inflated state.

13. The catheter according to claim 1, wherein the catheter also includes a sleeve supporting member disposed between the balloon and the sleeve to support the sleeve in the expanded state after the balloon is deflated.

14. The catheter according to claim 13, wherein the sleeve supporting member is selected from
a sleeve supporting member having a distal end co-extending to the same distance of the distal end of the sleeve when the sleeve is in the expanded state,
a sleeve supporting member having a distal end such that the distal end of the sleeve extends distally beyond the distal end of the sleeve supporting member when the sleeve is in the expanded state, and
a sleeve supporting member having a distal end such that the distal end of the sleeve supporting member extends distally beyond the distal end of the sleeve when the sleeve is in the expanded state.

15. The catheter according to claim 13, wherein the sleeve supporting member is selected from an expandable elastic member, a compressed elastic member, an expandable spring-like member, a compressed spring-like member, a coiled member, a compressed elastic coiled member, and a helically coiled member.

16. The catheter according to claim 1, wherein the sleeve is a perforated sleeve having perforations therein and wherein the catheter also includes a substance disposed between the sleeve and the balloon, such that upon inflating the balloon at least a portion of the substance is extruded through the perforation and is applied to the wall of a body cavity within which the catheter is disposed.

17. The catheter according to claim 16, wherein the perforations have opening dimensions in the range between 0.001-0.5 millimeter.

18. The catheter according to claim 16, wherein the perforations are selected from perforations having circular cross sections and perforations having non-circular cross sections.

19. The catheter according to claim 16, wherein the substance comprises one or more materials selected from, a therapeutic substance, a diagnostic substance, a drug, a therapeutic composition, a medicament, a diagnostic composition, a physiologically active agent, a biochemically active agent, one or more living cells, DNA, RNA, a nucleic acid, a vector for delivering genetic material to cells in the treated site, an anti-inflammatory agent, an anti-restenosis agent, a cell proliferation inhibitory agent, a smooth muscle proliferation inhibiting agent, Paclitaxel, rapamycin, everolimus, a vaso-active agent, a vaso dilating agent, a vaso constricting agent, an antibiotic agent, an anti-coagulative agent, a platelet aggregation inhibiting agent, an anti-fibrosis agent, a pharmaceutically acceptable vehicle, a lipid based vehicle, and any combinations thereof.

20. The catheter according to claim 16, wherein the perforated sleeve comprises a material having a sponge-like structure with open cavities allowing extrusion of the substance to the outer surface of the sleeve when the balloon is inflated.

21. The catheter according to claim 1, wherein the catheter also includes a soft tip attached to the catheter shaft at its distal end.

22. The catheter according to claim 21, wherein the soft tip includes a retaining member for securing the distal end of one or more of the balloon and the sleeve during insertion of the catheter into a body cavity and during moving the distal end of the catheter towards the treatment site in the cavity.

23. The catheter according to claim 1, wherein prior to inflating the balloon the sleeve has a circular cross-section and the balloon is folded around a portion of the catheter shaft prior to inflating the balloon.

24. The catheter according to claim 1, wherein both the sleeve and the balloon are folded around a portion of the catheter shaft prior to inflating the balloon to reduce the crossing profile of the catheter.

25. The catheter according to claim 1, wherein the balloon is folded around a portion of the catheter shaft prior to inflating the balloon, and wherein the sleeve is folded over the balloon to reduce the crossing profile of the catheter.

26. The catheter according to claim 1, wherein the sleeve comprises a material selected from a compliant material, a semi-compliant material, a non-compliant material, a stretchable material, a non-stretchable material, an annealed stretchable material, a pre-stretched non-stretchable material that has undergone molecular orienting by biaxial orienting processes, and any combinations thereof.

27. The catheter according to claim 1, wherein the sleeve comprises a material selected from a polymer based material, Nylon® Nylon 12®, PET, a polyimide PA12, Grilamid® L25, Grilamid® L55, PA11, Polyether block amides PEBAX®7233, PEBAX®7033, PEBAX®6333), Grilflex® ELG 6260, Polyester, polyethylene, polyurethane and any combinations thereof.

28. The catheter according to claim 1, wherein the catheter also includes one or more devices selected from the group consisting of,
one or more radio-opaque markers attached to the catheter shaft, and
one or more position detection assisting devices attached to one or more parts of the catheter for enabling a three dimensional catheter positioning system to determine the position of at least part of the catheter in a reference frame defined in three dimensional space.

29. The catheter according to claim 1, wherein the balloon is selected from the group consisting of a cylindrical balloon having conical or tapering ends, a stepped balloon having two or more cylindrical portions having different diameters of at least some of the cylindrical portions, a balloon having a conical or truncated conical longitudinal cross-sectional shape, a balloon having a tapering longitudinal cross-sectional shape, a balloon having a non-linearly varying longitudinal cross sectional shape, a balloon having at least one corrugated portion, a balloon having a uniform wall thickness, and a balloon having a non-uniform wall thickness.

30. A method for treating a body cavity, the method comprising the steps of:
inserting a catheter as defined in claim 1 into the body cavity;
positioning the sleeve at a treatment site of the cavity;
inflating the balloon to expand the sleeve to an expanded state; and
deflating the balloon to form an open cavity between the expanded sleeve and the balloon such that the deflating generates suction that captures and retains debris and/or particulate matter within the cavity.

31. The method according to claim 30, wherein the step of inserting comprises inserting the catheter into the body cavity over a guide wire passing through a hollow passage formed within the catheter shaft.

32. The method according to claim 30, wherein the body cavity is a blood vessel.

33. The method according to claim 32, wherein the step of inflating the balloon also opens an occlusion in the blood vessel.

34. The method according to claim 30, wherein the catheter also includes a sleeve supporting member disposed between the balloon and the sleeve and wherein the step of inflating the balloon also includes a step selected from the steps of,
expanding the sleeve supporting member by the balloon to an expanded state for supporting the expanded state of the sleeve; and
allowing the sleeve supporting member to expand from an initially compressed state to an expanded state for supporting the expanded state of the sleeve.

35. The method according to claim 30, wherein the sleeve is a perforated sleeve and the catheter also includes a substance disposed between the balloon and the perforated sleeve, and wherein the step of inflating the balloon also includes the step of applying the substance to a site in the body cavity by extruding the substance through perforations in the perforated sleeve to apply a portion of the substance to part of the body cavity.

36. The method according to claim 30, wherein the catheter also includes a stent disposed on the outer surface of the sleeve and wherein the step of inflating the balloon also includes the step of expanding the stent to deploy the stent in the body cavity.

37. The method according to claim 30, wherein the catheter shaft includes a hollow passage fluidically connected to the cavity formed between the balloon and the sleeve and wherein the method also includes the step of applying suction to the cavity from an external suction source through the hollow passage to assist the capturing and the retaining of debris within the cavity of the catheter.

38. The method according to claim 37, wherein the step of applying suction also comprises the step of capturing and retaining at least some of the debris within the hollow passage connected to the cavity.

39. The method according to claim 30, wherein the catheter shaft comprises at least three fluidically separate hollow passages therein, the at least three hollow passages comprise a first hollow passage having a first opening disposed on the catheter shaft for inserting a guide wire there through and a second opening disposed at the distal end of the catheter shaft for allowing the guide-wire to exit through the second opening, a second hollow passage for inserting and withdrawing inflation fluid into and from the balloon, respectively, and a third hollow passage fluidically connected to the cavity between the balloon and the sleeve through the third hollow passage,
and wherein the method also includes the step of applying suction from an external suction source to the cavity through the third hollow passage to assist the capturing and the retaining of the debris within the cavity or within the third hollow passage.

40. The method according to claim 30, wherein the method also includes the step of inserting through a hollow passage of the shaft a device selected from a diagnostic device for performing a diagnostic procedure within the body cavity and a therapeutic device for performing a therapeutic procedure in the body cavity.

41. The method according to claim 40, wherein the device is inserted into the catheter through a hollow passage used for inserting a guide wire into the catheter and wherein the method also includes the step of withdrawing a guide wire from the hollow passage prior to inserting the device.

42. The method according to claim 30, wherein the method also includes the step of injecting a contrast enhancing agent through a hollow passage in the catheter shaft.

43. The method according to claim 30, wherein the step of inflating the balloon also includes a step selected from the steps of,
opening the sleeve by the balloon,
unfolding the sleeve by the balloon,
expanding the sleeve by the balloon,
stretching the sleeve by the balloon,
and any combinations thereof.

* * * * *